(12) United States Patent
Schraga

(10) Patent No.: US 9,392,968 B2
(45) Date of Patent: Jul. 19, 2016

(54) LANCET NEEDLE CARTRIDGE, CARTRIDGE LANCET DEVICE, AND METHOD OF USING AND MAKING THE SAME

(75) Inventor: Steven Schraga, Surfaide, FL (US)

(73) Assignee: STAT MEDICAL DEVICES, INC., North Miami Beach, FL (US)

( * ) Notice: Subject to any disclaimer, the term of this patent is extended or adjusted under 35 U.S.C. 154(b) by 2583 days.

(21) Appl. No.: 12/018,648

(22) Filed: Jan. 23, 2008

(65) Prior Publication Data

US 2009/0187204 A1 Jul. 23, 2009

(51) Int. Cl.
| | |
|---|---|
| A61B 17/14 | (2006.01) |
| A61B 5/15 | (2006.01) |
| A61B 5/00 | (2006.01) |
| A61B 5/151 | (2006.01) |
| A61B 5/145 | (2006.01) |

(52) U.S. Cl.
CPC ............. *A61B 5/1411* (2013.01); *A61B 5/1513* (2013.01); *A61B 5/150022* (2013.01); *A61B 5/15105* (2013.01); *A61B 5/15113* (2013.01); *A61B 5/15117* (2013.01); *A61B 5/15123* (2013.01); *A61B 5/15153* (2013.01); *A61B 5/15163* (2013.01); *A61B 5/15182* (2013.01); *A61B 5/150183* (2013.01); *A61B 5/150412* (2013.01); *A61B 5/150473* (2013.01); *A61B 5/150503* (2013.01); *A61B 5/150572* (2013.01); *A61B 5/150748* (2013.01); *A61B 5/150977* (2013.01); *A61B 5/411* (2013.01); *A61B 5/14532* (2013.01)

(58) Field of Classification Search
CPC ... A61B 5/1411; A61B 5/14532; A61B 5/411
USPC .................... 606/181, 182, 183, 186
See application file for complete search history.

(56) References Cited

U.S. PATENT DOCUMENTS

| | | | |
|---|---|---|---|
| 5,035,704 A | | 7/1991 | Lambert et al. |
| 5,201,324 A | | 4/1993 | Swierczek |
| 5,395,388 A | | 3/1995 | Schraga |
| 5,643,306 A | | 7/1997 | Schraga |
| 6,228,100 B1 | | 5/2001 | Schraga |
| 6,506,168 B1 | | 1/2003 | Fathallah et al. |
| 6,530,937 B1 | * | 3/2003 | Schraga .................. 606/182 |
| 6,616,616 B2 | * | 9/2003 | Fritz et al. .................. 600/583 |
| 2002/0169470 A1 | | 11/2002 | Kuhr et al. |
| 2003/0050573 A1 | | 3/2003 | Kuhr et al. |
| 2004/0133127 A1 | * | 7/2004 | Roe et al. .................. 600/583 |
| 2004/0230216 A1 | | 11/2004 | Levaughn et al. |
| 2004/0260325 A1 | * | 12/2004 | Kuhr et al. .................. 606/181 |
| 2005/0021066 A1 | | 1/2005 | Kuhr et al. |
| 2005/0118071 A1 | | 6/2005 | Sacherer |
| 2006/0157362 A1 | | 7/2006 | Schraga |
| 2006/0161078 A1 | | 7/2006 | Schraga |
| 2006/0224172 A1 | | 10/2006 | LeVaughn et al. |
| 2006/0241668 A1 | | 10/2006 | Schraga |

(Continued)

*Primary Examiner* — Corrine McDermott
*Assistant Examiner* — Sarah Simpson
(74) *Attorney, Agent, or Firm* — Greenblum & Bernstein, P.L.C.

(57) ABSTRACT

Assembly for use on a device includes a member comprising a plurality of lancet needles arranged generally parallel to each other and one of a cap comprising a single lancet opening structured and arranged to receive therein an end portion of a finger tip and a cap comprising a plurality of openings which are each sized to allow one of the lancet needles to pass therethrough. This Abstract is not intended to define the invention disclosed in the specification, nor intended to limit the scope of the invention in any way.

63 Claims, 51 Drawing Sheets

(56) References Cited

U.S. PATENT DOCUMENTS

| | | |
|---|---|---|
| 2006/0264996 A1 | 11/2006 | LeVaughn et al. |
| 2006/0271084 A1 | 11/2006 | Schraga |
| 2007/0088377 A1 | 4/2007 | LeVaughn et al. |
| 2007/0142854 A1 | 6/2007 | Schraga |
| 2007/0299458 A1 | 12/2007 | Epple |
| 2008/0039887 A1 | 2/2008 | Conway et al. |
| 2008/0119883 A1 | 5/2008 | Conway et al. |

\* cited by examiner

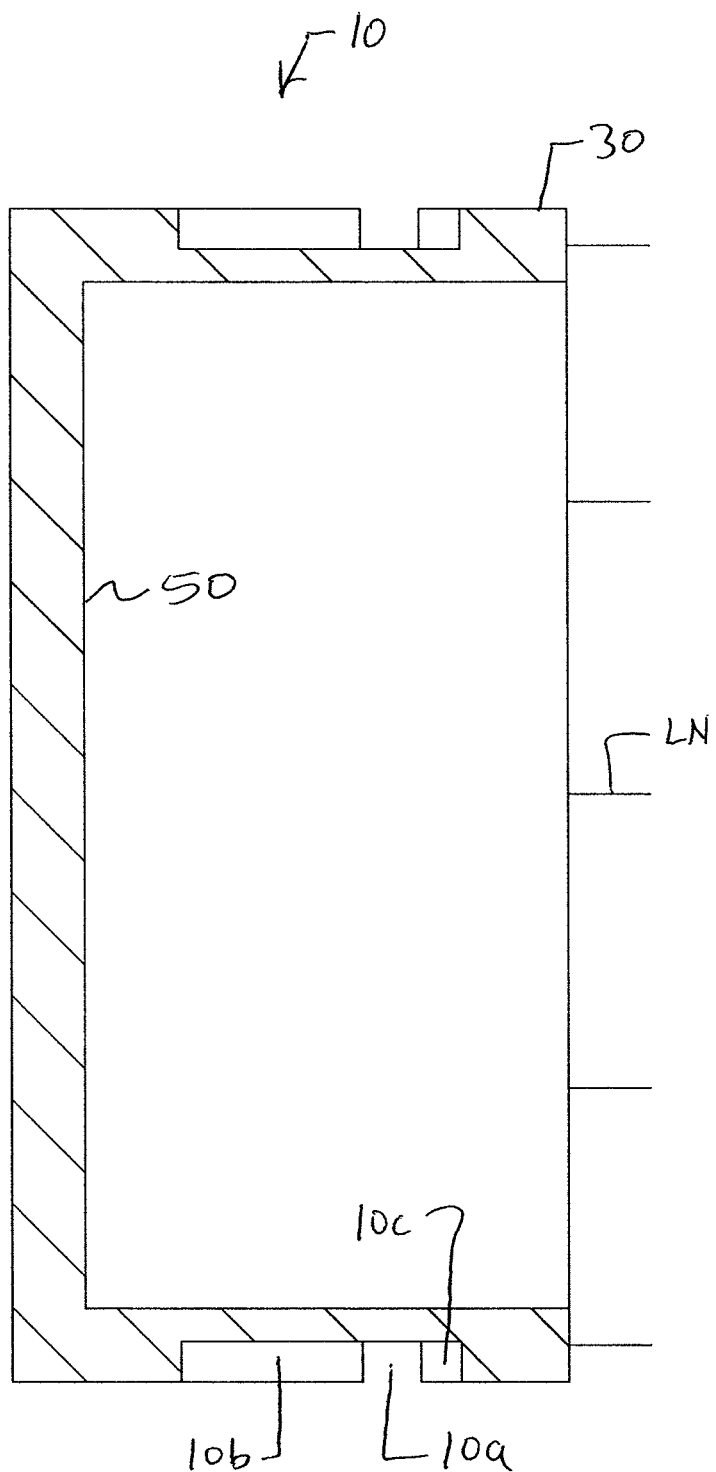

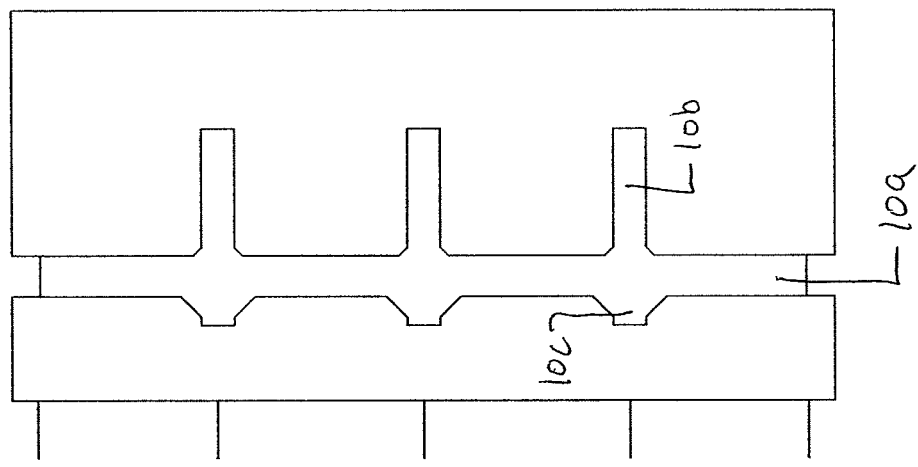
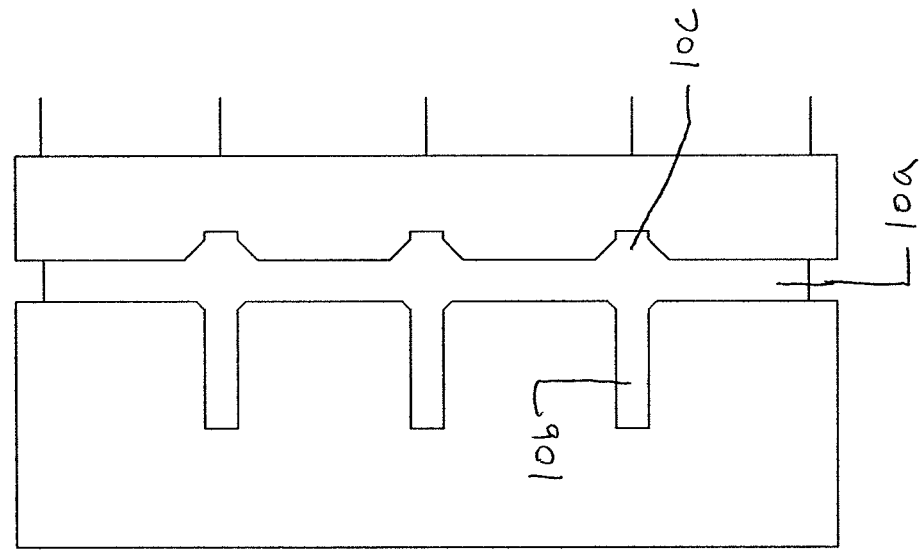

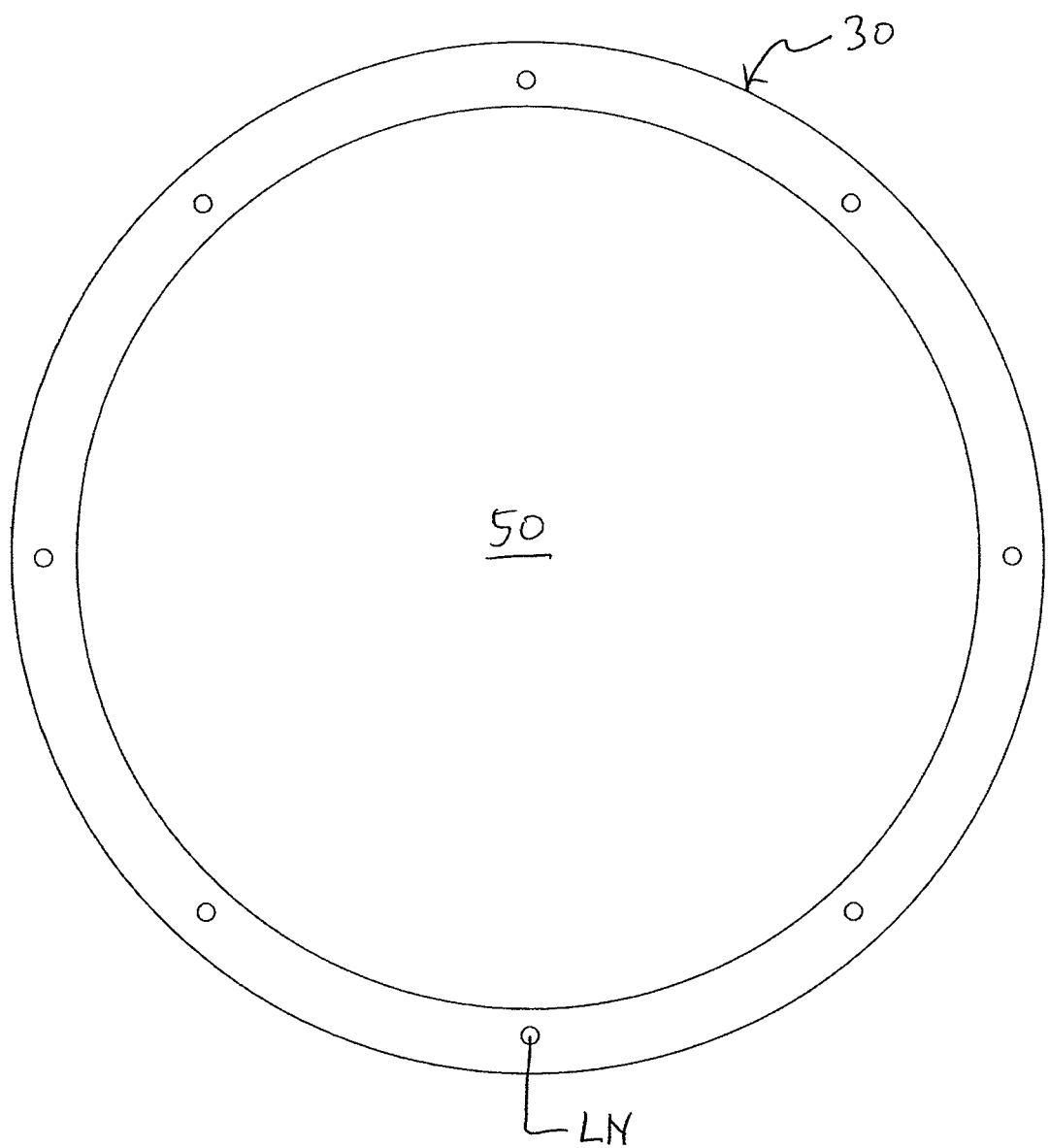

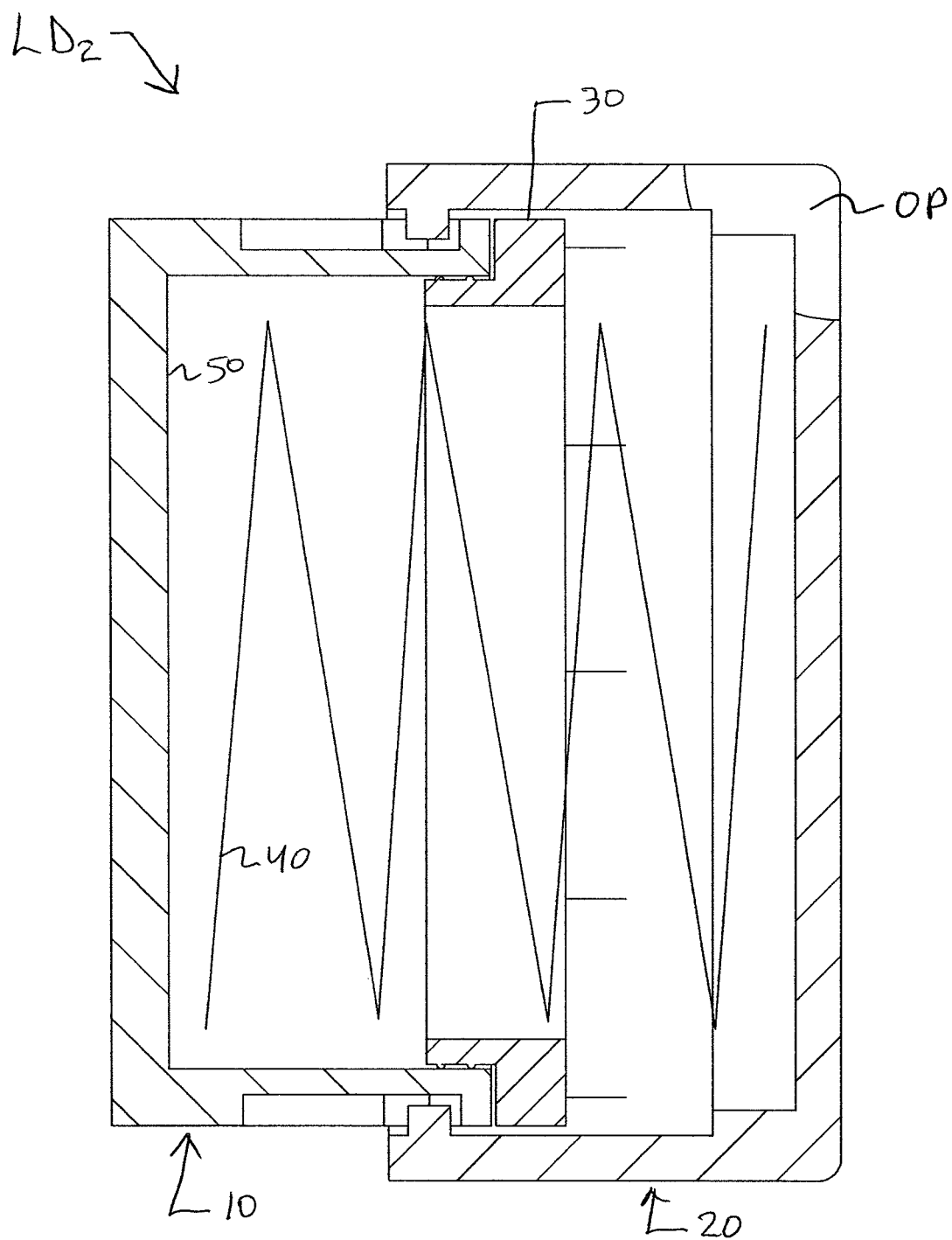

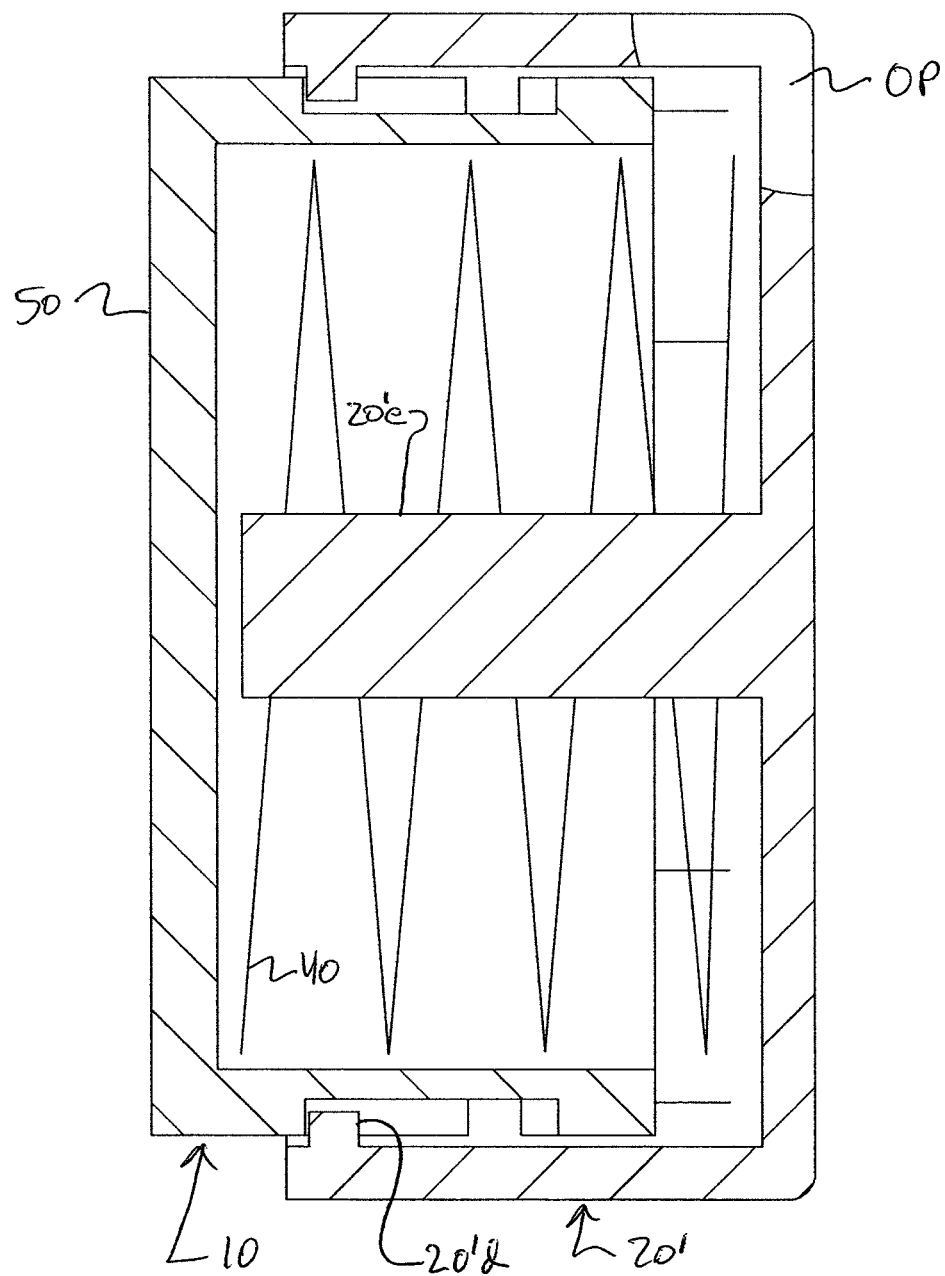

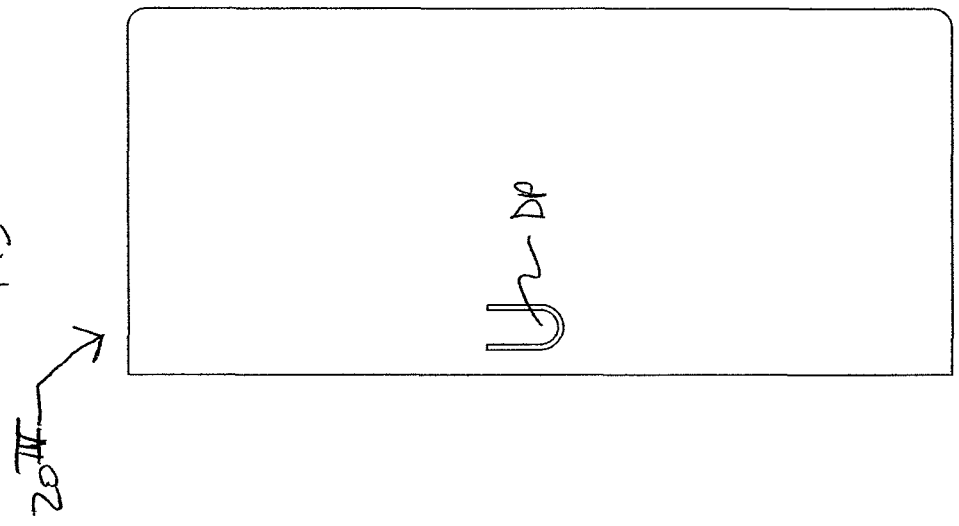
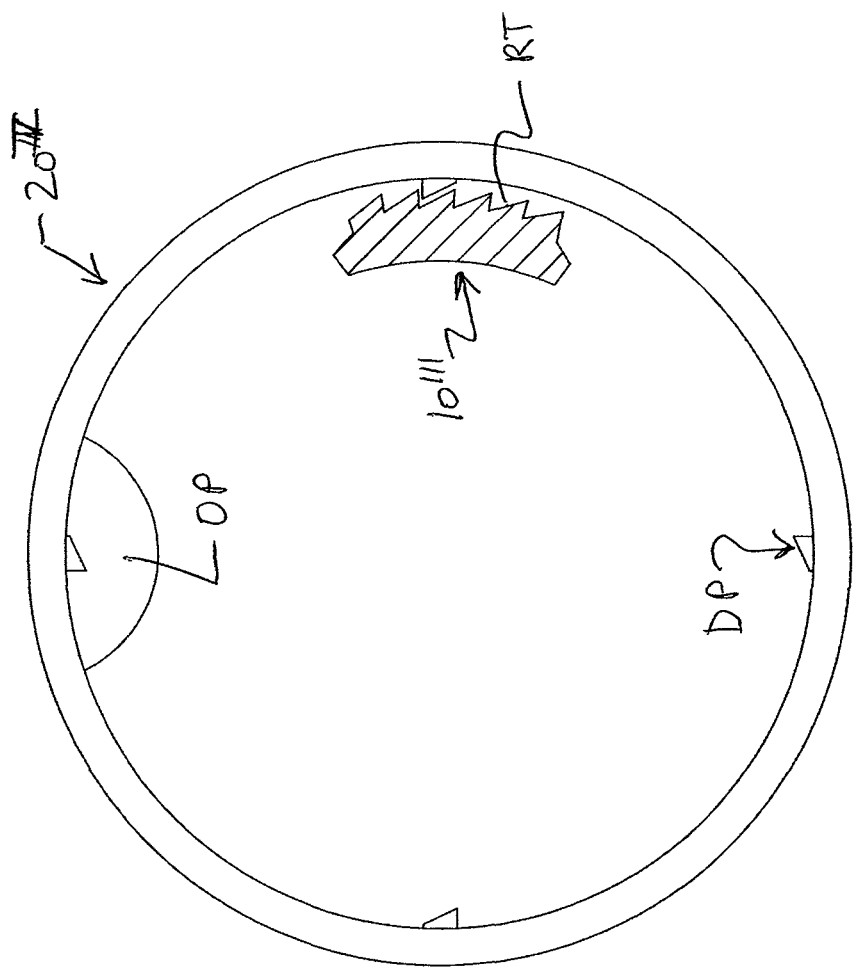

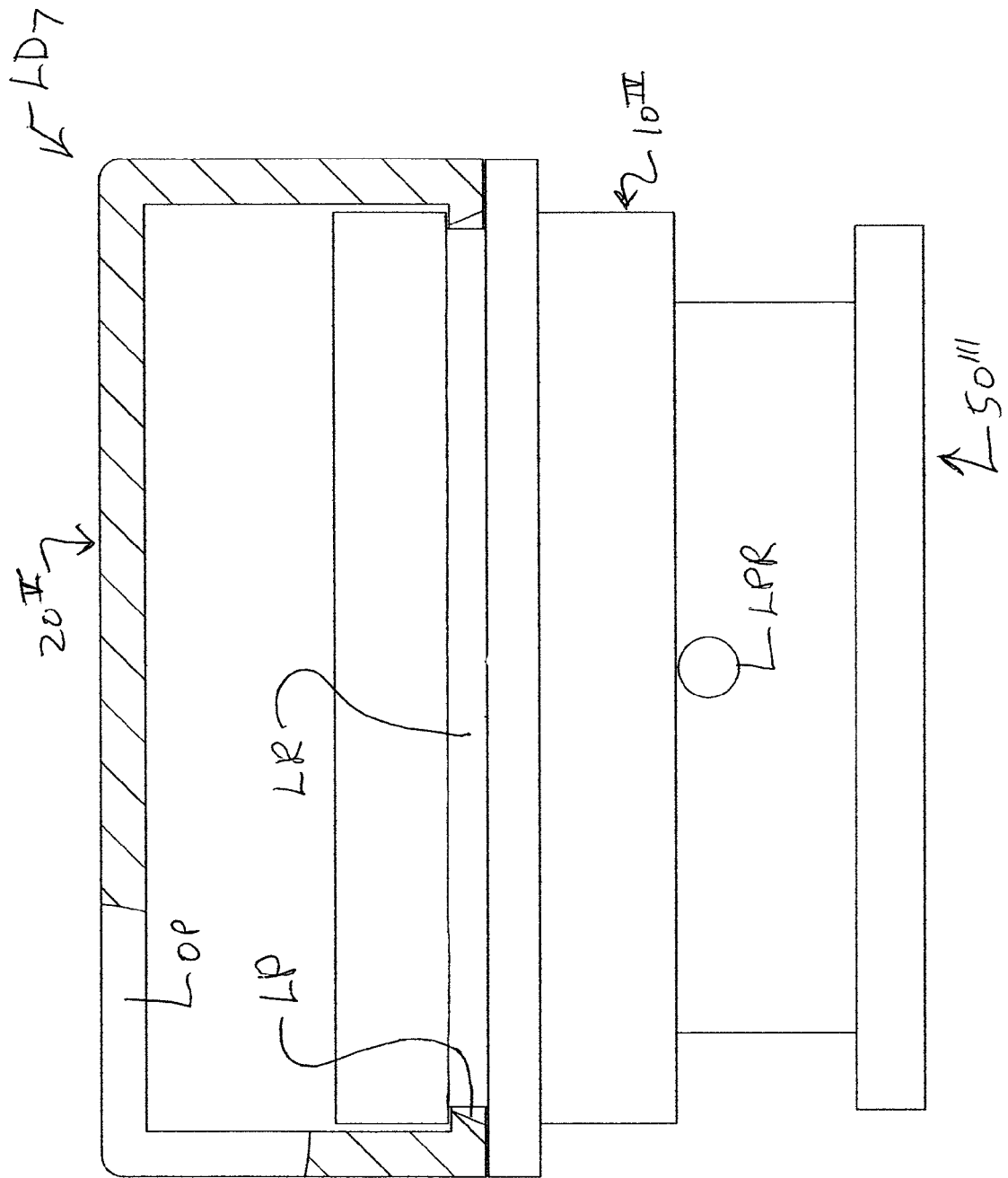

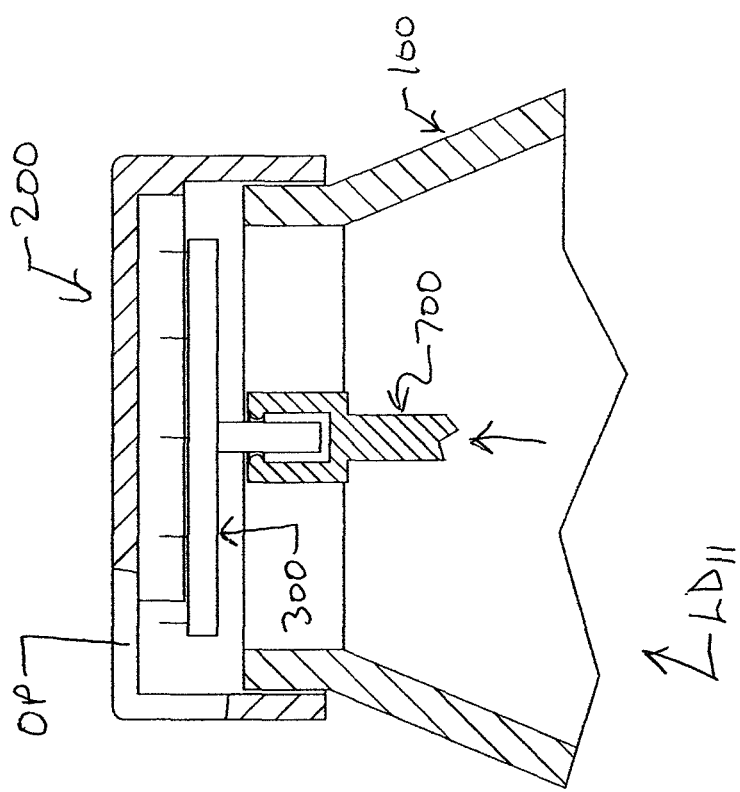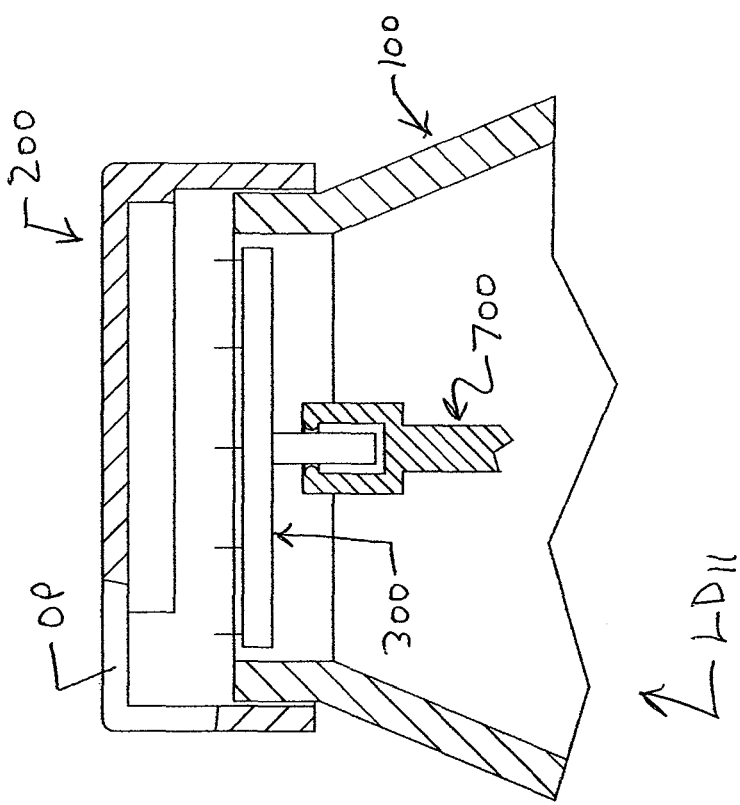

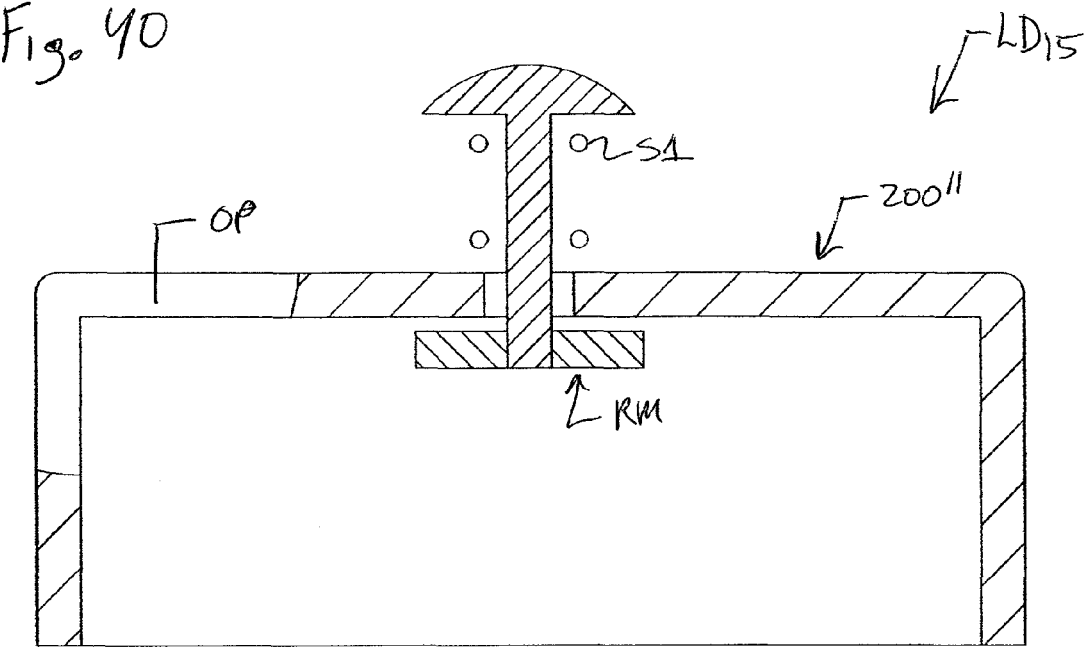
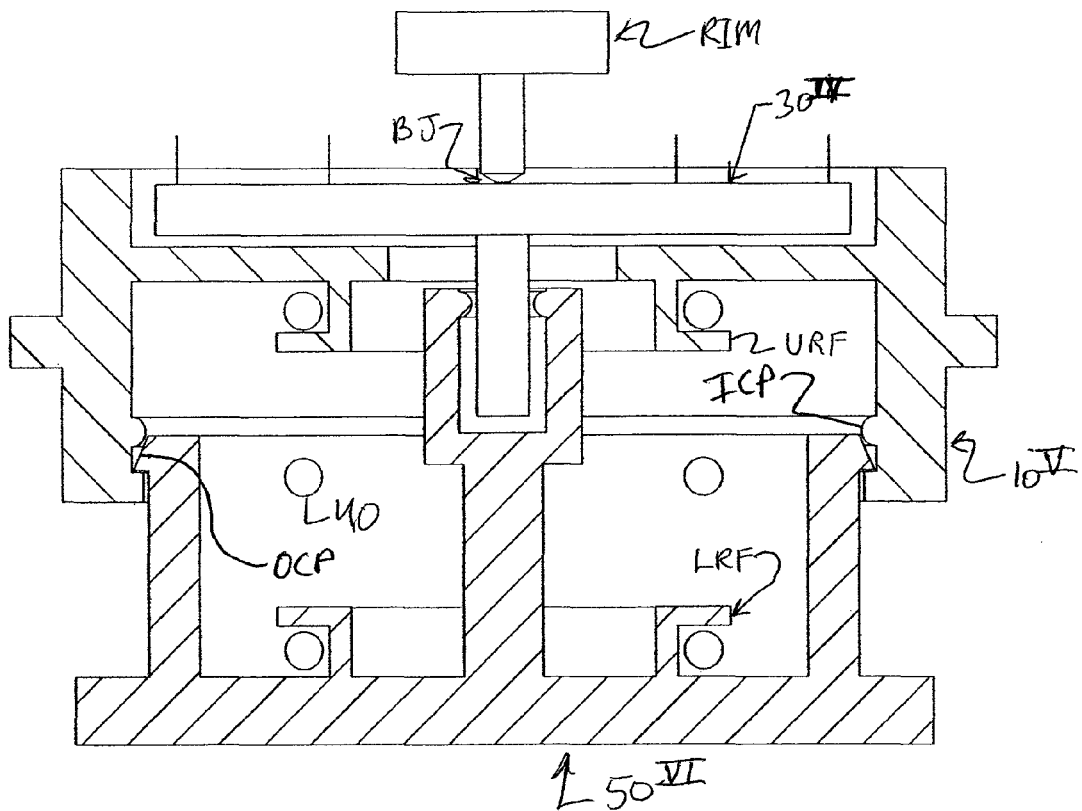
Fig. 40

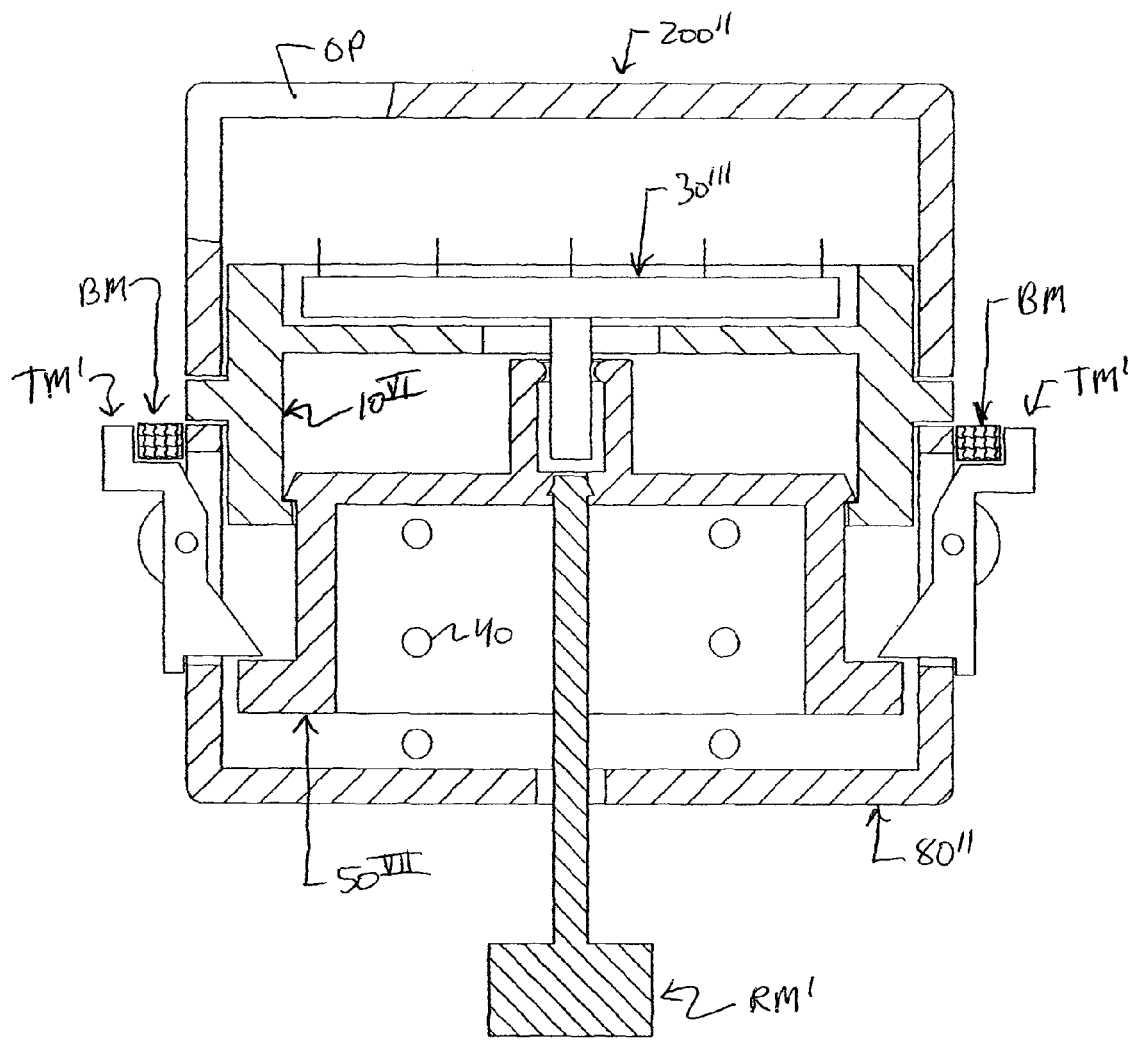

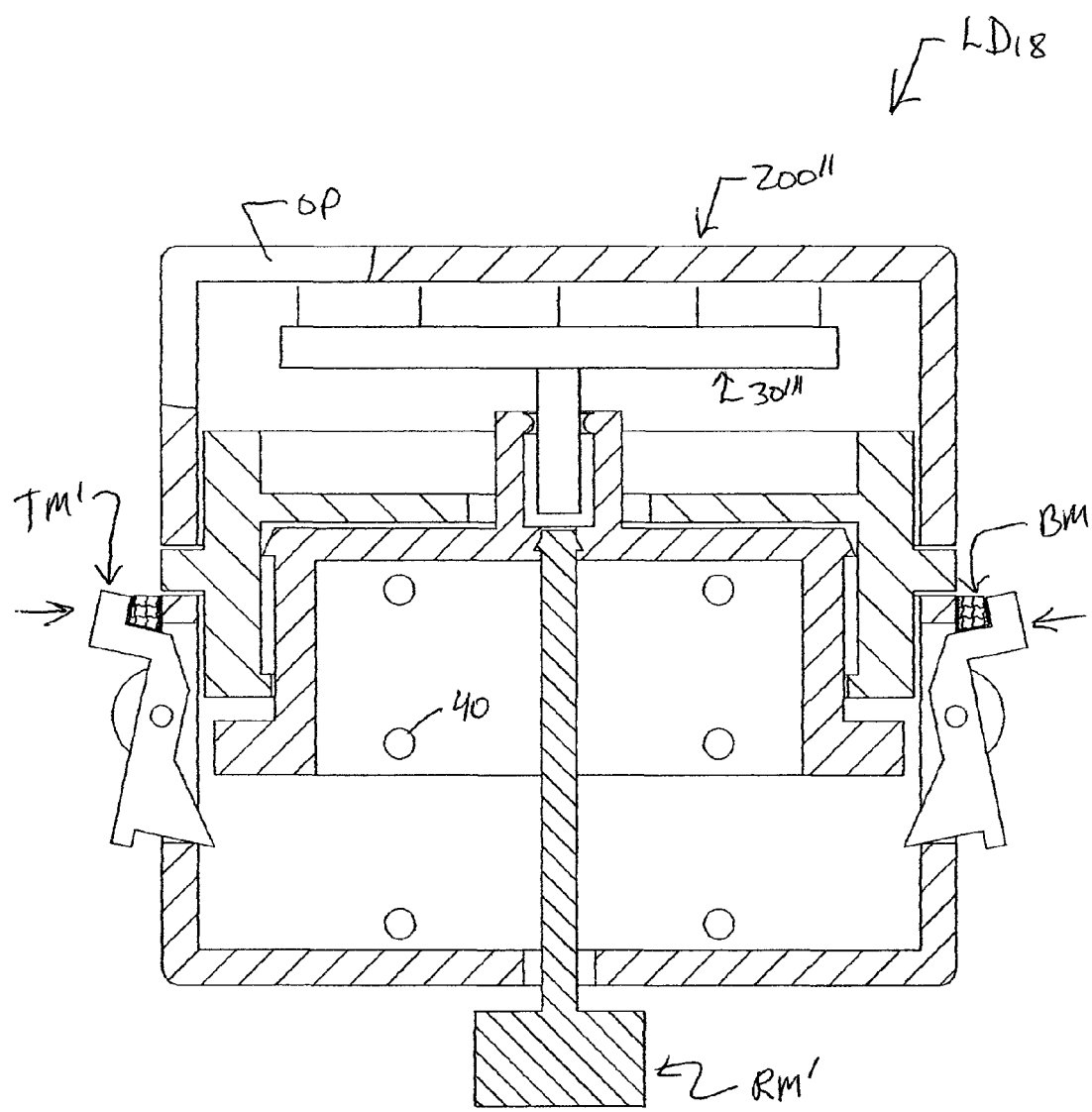

Fig. 48
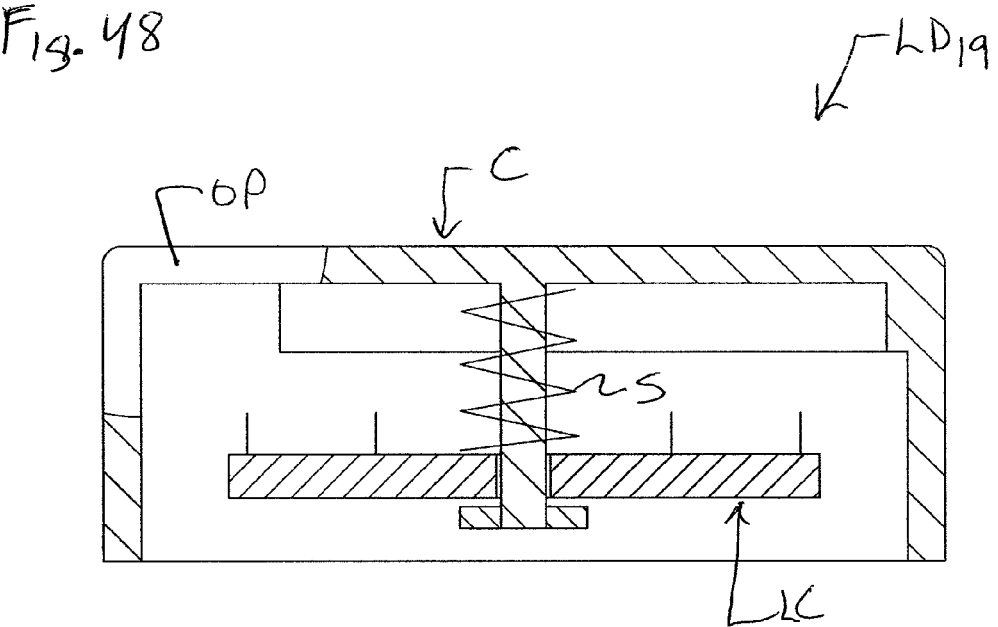
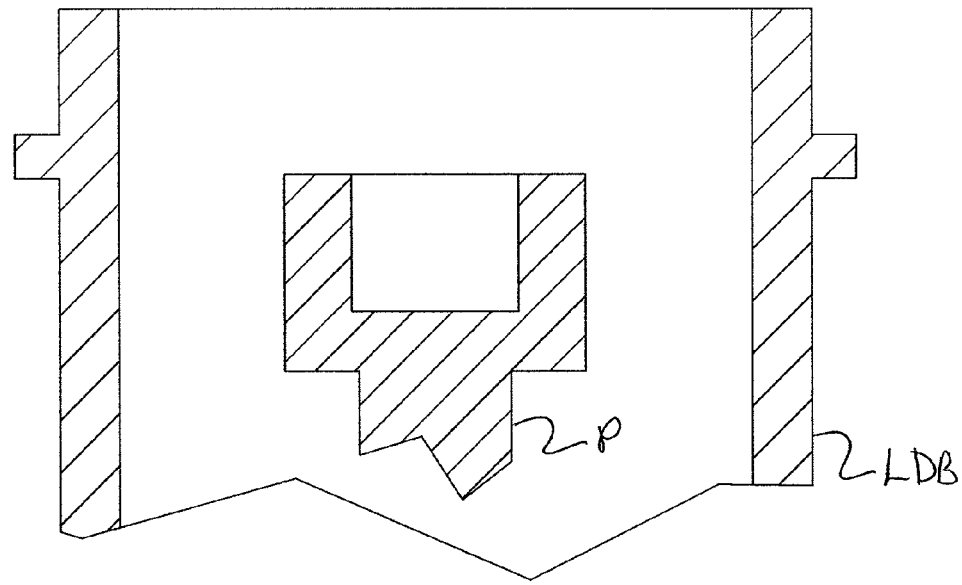

Fig. 52
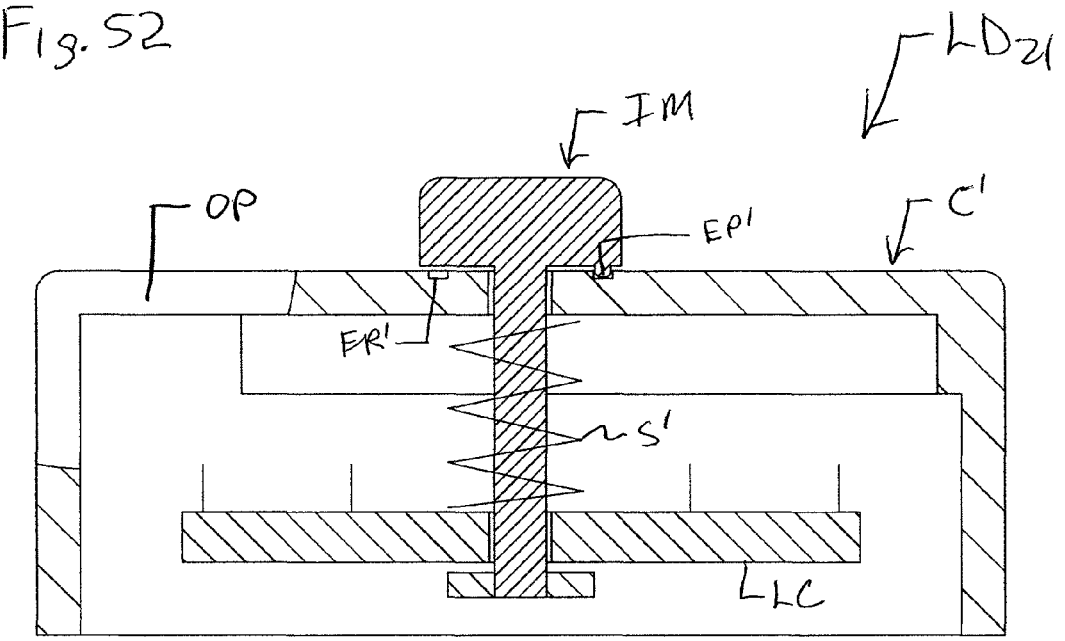
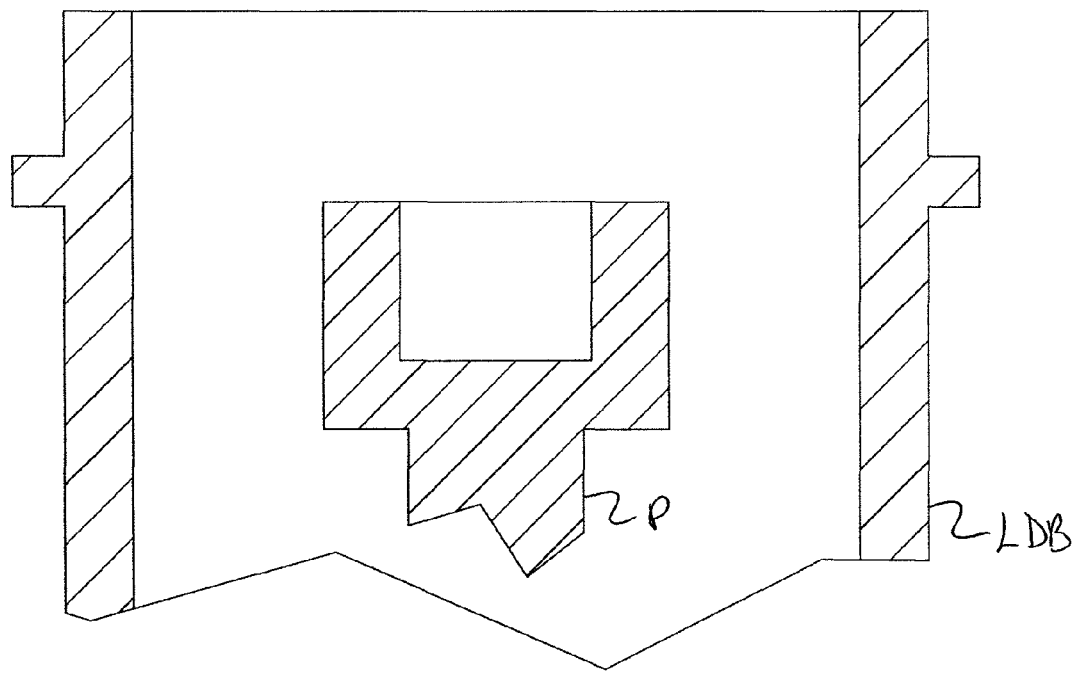

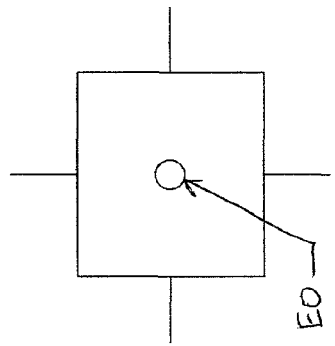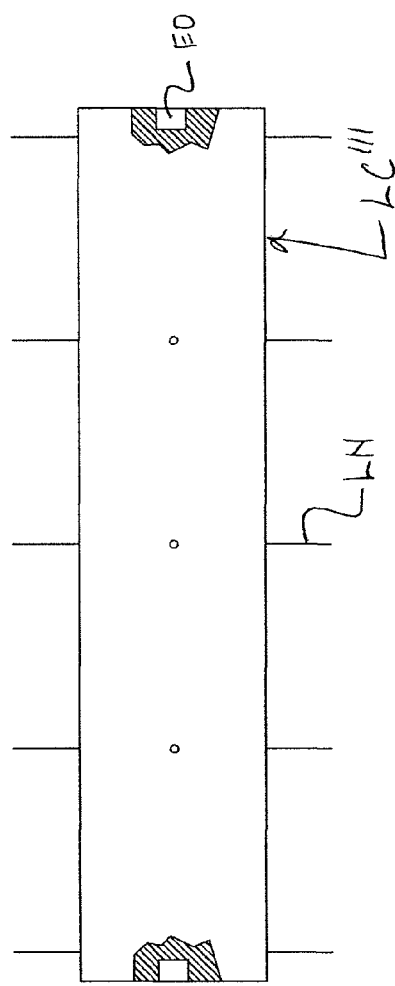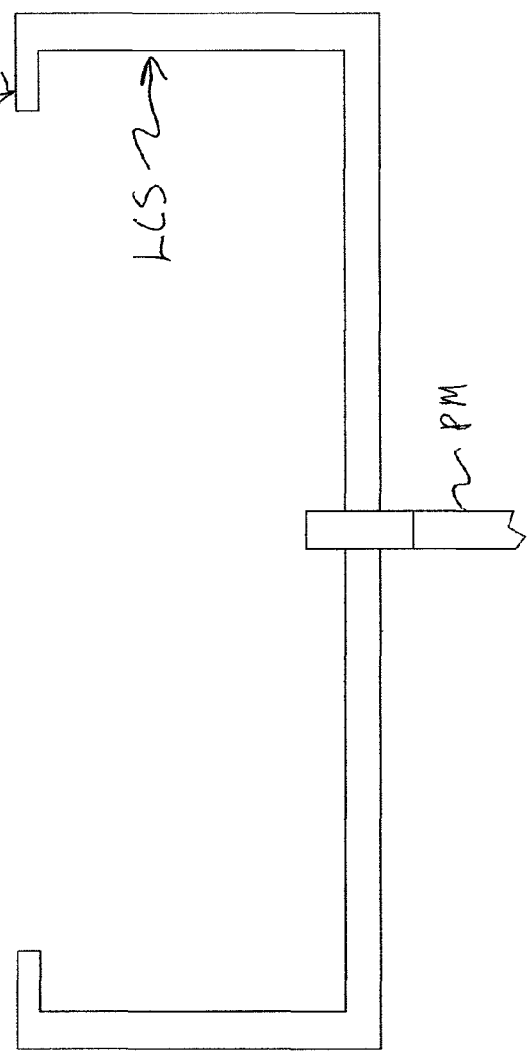

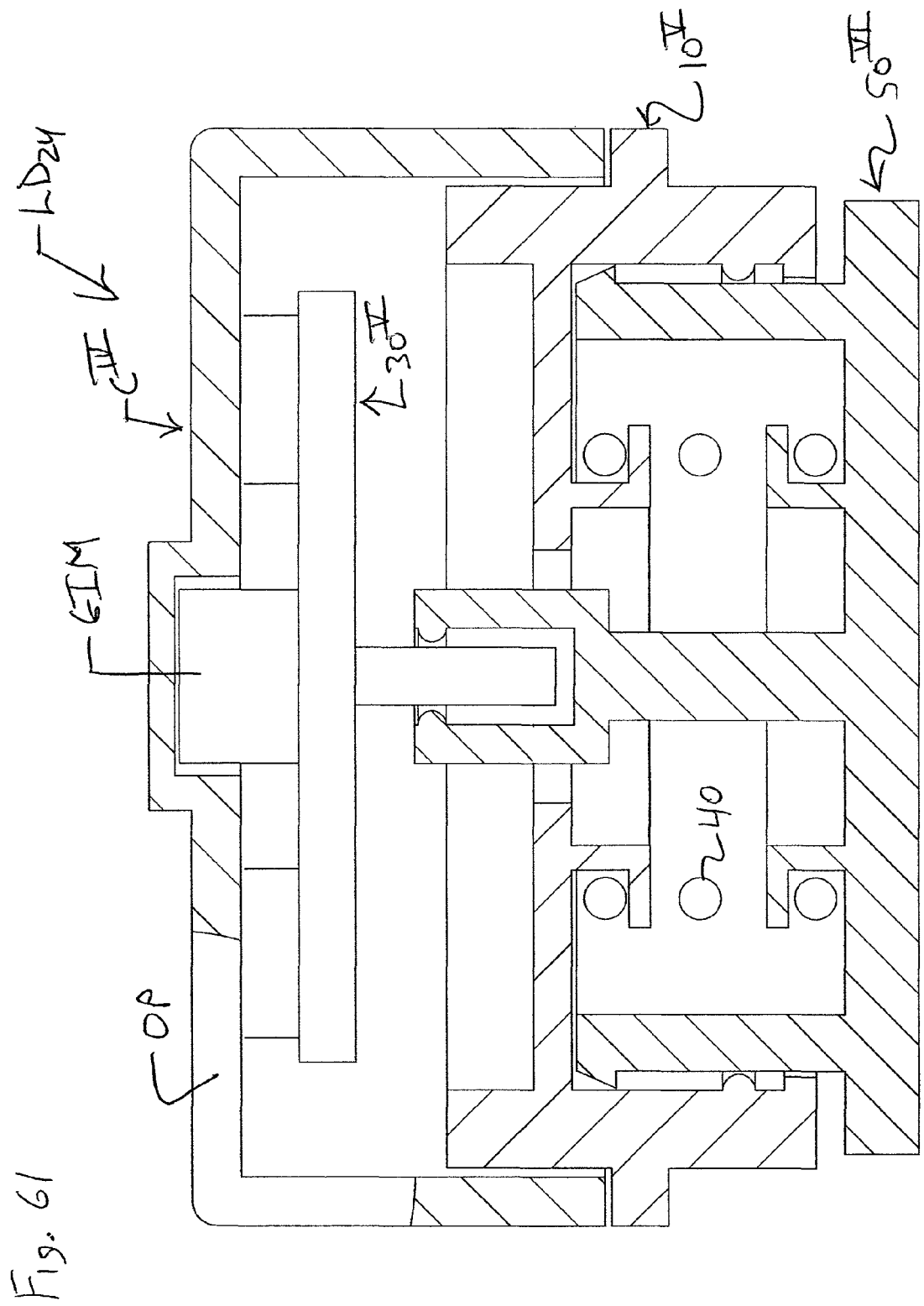

LANCET NEEDLE CARTRIDGE, CARTRIDGE LANCET DEVICE, AND METHOD OF USING AND MAKING THE SAME

BACKGROUND OF THE INVENTION

1. Field of the Invention

The invention relates to a cartridge having a plurality of needles, a device which utilizes the cartridge, and a method of using the cartridge to cause one or more punctures in a user's skin. The invention also relates to a lancet device which is easier to use and/or more economical and which is more efficient to make. The invention also relates to a lancet or testing device preferably utilizing a cap having either one lancet opening or plural lancet openings as well as a cartridge having plural lancet needles. The invention also relates to a method of using a lancet or testing device.

2. Discussion of Background Information

Lancet devices are used to penetrate and puncture the skin in order to allow the taking of a blood sample for testing. In particular, lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Moreover, controlling the depth of penetration cannot be reliably accomplished without the use of a mechanical device. Additionally, many users simply cannot perform the procedure owing to either a fear of needles or because they lack a steady hand. As a result, lancet devices have been developed which allow the user to more easily and reliably perform this procedure.

What is needed is a simpler lancet device which can be used numerous times, is easy to use, and is inexpensive to manufacture. It is further also desirable to allow the user to cock and trigger the lancet device in an easy manner. Still further, because many conventional lancet devices can possibly be cocked and/or triggered by accidentally, e.g., such as by dropping the lancet device on the floor, a need exists for a lancet device which cannot be triggered accidentally, and is so triggered, does not easily cause a puncture of a user skin.

SUMMARY OF THE INVENTION

According to one aspect of the invention there is provided an assembly for use on a device, wherein the assembly comprises a member comprising a plurality of lancet needles arranged generally parallel to each other and one of a cap comprising a single lancet opening structured and arranged to receive therein an end portion of a finger tip and a cap comprising a plurality of openings which are each sized to allow one of the lancet needles to pass therethrough.

The device may comprise at least one of a lancet device and a testing device, and a skin allergy test.

The assembly may comprise the cap comprising a single lancet opening structured and arranged to receive therein an end portion of a finger tip device, and the lancet opening may be arranged in a peripheral area of the cap.

The assembly may comprise the cap comprising a plurality of openings which are each sized to allow one of the lancet needles to pass therethrough, and the member may be movable at least from one position wherein each lancet needle does not extend out past an outer surface of the cap and another position wherein each lancet needle extends out past the outer surface of the cap.

The assembly may comprise the cap comprising a single lancet opening structured and arranged to receive therein an end portion of a finger tip device, and the lancet opening may be movable from one position which coincides with one of the lancet needles to another position which coincides with another of the lancet needles.

The assembly may comprise the cap comprising a single lancet opening structured and arranged to receive therein an end portion of a finger tip device, and the member may be movable from one position wherein the lancet opening coincides with one of the lancet needles to another position wherein the lancet opening coincides with another of the lancet needles.

The cap and member may be generally circular shaped. The cap may be generally cylindrically shaped. The cap may comprise a generally circular end surface and a generally cylindrical sidewall and wherein the lancet opening is located at a corner area between the end surface and the sidewall. The lancet opening may be located at a corner area of the cap.

The assembly may further comprise at least one spring structured and arranged to bias the member towards the cap. The assembly may further comprise at least one spring structured and arranged to bias the member away from the cap.

The member and the cap may be movable relative to each other from a retracted position to a puncturing position and one of the cap may be rotatable relative to the member and the member may be rotatable relative to the cap. The member and the cap may be axially movable relative to each other and the cap is rotatable relative to the member. The member and the cap may be axially movable relative to each other and the member is rotatable relative to the cap. The member and the cap may be movable relative to each other and at least one of the cap may be a one-piece member and the member may be a one-piece member. The member and the cap may be movable relative to each other and at least one of the cap may be a generally cylindrical member and the member may be a generally cylindrical member. The member and the cap may be movable relative to each other and at least one of the cap may be a generally cylindrical member and the member may be a generally disk-shaped member. The member and the cap may be movable relative to each other and at least one of the cap may be a rotatable between distinct angular positions which correspond to angular positions of the lancet needles and the member may be a rotatable between distinct angular positions which correspond to angular positions of the lancet needles. The member and the cap may be movable relative to each other and at least one of the cap may be rotatable between distinct angular positions which correspond to angular positions of the lancet needles and axially movably only at the distinct angular positions and the member may be rotatable between distinct angular positions which correspond to angular positions of the lancet needles and axially movably only at the distinct angular positions. The member and the cap may be movable relative to each other and at least one of the cap may be a one-piece member and the member may be a one-piece member that is capable of being mounted to a portion of the device.

The device may be structured and arranged to be disposed of after all of the lancet needles are used to puncture a user's skin. All of the lancet needles may have substantially the same axial length. All of the lancet needles may project from or extend out past a surface by substantially the same amount.

The member may be non-removably mounted to a portion of the device, whereby the device is structured and arranged to be disposed of after all of the lancet needles are used to puncture a user's skin.

The member and the cap may be movable relative to each other and at least one of the cap may comprise a member for limiting axial movement of the relative movement of the cap and the member and the member may comprise a member for limiting axial movement of the relative movement of the cap and the member.

The member may be removably mounted to a movable portion of the device. The member may be removably mounted to an axially movable portion of the device. The member may be removably mounted to an axially and rotatably movable portion of the device. The member may be mounted to an axially and rotatably movable portion of the device.

The assembly may further comprise a device for rotating the movable portion of the device between discrete rotational positions, wherein each position results in the lancet needle opening being substantially aligned with one of the lancet needles. The assembly may further comprise a device for rotating the movable portion of the device between discrete rotational positions, wherein each position results in one of the lancet needles being substantially aligned with the lancet needle opening.

The assembly may further comprise a back cap structured and arranged to move the movable portion from an initial position to a puncturing position.

The assembly may further comprise a spring structured and arranged to bias the movable portion towards the initial position. The assembly may further comprise a spring structured and arranged to bias the movable portion towards the puncturing position. The assembly may further comprise a back cap structured and arranged to move the member from an initial position to a puncturing position. The cap may be non-removably mounted. The cap may be non-movably mounted.

The member may comprise a disk-shaped portion having a surface from which the lancet needles project and rod-shaped portion extending from a side opposite the surface.

The assembly may further comprise at least one retractable protection member arranged to cover at least one of the lancet needles.

The assembly may further comprise an arrangement for ensuring that the cap rotates in only one direction. The assembly may further comprise an arrangement for ensuring that the member rotates in only one direction. The assembly may further comprise an arrangement for ensuring that the cap rotates in only one direction relative to a body of the device. The assembly may further comprise an arrangement for ensuring that the lancet opening rotates in only one direction relative to a body of the device and between a number of discrete positions corresponding to a number of the lancet needles. The assembly may further comprise an arrangement for ensuring that the lancet opening moves in only one direction relative to a body of the device and between a number of discrete positions corresponding to a number of the lancet needles. The assembly may further comprise a system for guiding a linear movement of the member relative to a body of the device at each of a number of discrete positions corresponding to a number of the lancet needles. The assembly may further comprise a system for preventing rotational movement of the cap when the cap is arranged on a body of the device.

The member may comprise a device for allowing a user to safely install the member on a portion of the device. The member may comprise a removable and/or breakable device for allowing a user to safely install the member on a portion of the device.

The assembly may further comprise a system for moving the member to at least one of an initial position and a retracted position. The assembly may further comprise a mechanism mounted to the cap for moving the member to at least one of an initial position and a retracted position. The assembly may further comprise a trigger for causing the member to move from at least one of an initial position and a retracted position to a puncturing position. The assembly may further comprise a system moving the member to at least one of an initial position and a retracted position and for causing the member to move to a puncturing position. The assembly may further comprise a mechanism coupled to a portion of the device for at least one of moving the member to at least one of an initial position and a retracted position and for causing the member to move to a puncturing position. The assembly may further comprise a first mechanism coupled to a portion of the device for moving the member to at least one of an initial position and a retracted position and a second mechanism coupled to another portion of the device for causing the member to move to a puncturing position.

The member may be movably mounted to the cap. The member may be axially movably mounted to the cap. The member may be rotatably mounted to the cap. The member may be non-removably mounted to the cap. The member may be biased away from the cap by a biasing member arranged between the member and the cap. The member may be coupled to the cap and further comprising a mechanism for rotating the member relative to the cap between discrete positions. The member may be coupled to the cap and further comprising a mechanism for temporarily retaining and/or locking the member in a plurality of discrete rotational positions relative to the cap. The member may additionally comprise at least one needle arranged generally perpendicular to the lancet needles.

The invention also provides for a method of puncturing a surface of skin using the assembly of the type described above, wherein the method comprises disposing a skin engaging end of the cap against a user's skin and manually causing the member to move towards a puncturing position.

The invention also provides for a method of puncturing a surface of skin using the assembly of the type described above, wherein the method comprises disposing a skin engaging end of the cap against a user's skin and causing the member to move towards a puncturing position.

The invention also provides for an assembly for use on a device, wherein the assembly comprises a cartridge comprising a plurality of lancet needles arranged generally parallel to each other and a cap comprising a single lancet opening structured and arranged to receive therein an end portion of a finger tip.

The invention also provides for an assembly for use on a device, wherein the assembly comprises a cartridge comprising a plurality of lancet needles arranged generally parallel to each other and a cap comprising a plurality of openings which are each sized to allow one of the lancet needles to pass therethrough.

The invention also provides for an assembly for use on a lancet or testing device, wherein the assembly comprises a cartridge comprising a plurality of lancet needles arranged generally parallel to each other and at least one other needle arranged non-parallel to the plurality of lancet needles. One, more, or all of the above-noted devices may utilize a device for adjusting a depth of penetration. Alternatively, the cartridge can comprise a plurality of radially oriented lancet needles arranged on a body having an axial length that is greater than an imaginary circle defined by free ends of the lancet needles. The cartridge can also comprise a plurality of radially oriented rows of lancet needles arranged on a body.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 5 shows a side cross-section view of a one-piece cartridge body member used in the embodiment shown in FIG. 1. This member includes a lancet needle cartridge portion arranged at a front end of a cylindrical body portion and a back cap portion arranged at a rear end of the cylindrical body portion;

FIG. 6 shows a left side view of the one-piece cartridge body member used in the embodiment shown in FIG. 1;

FIG. 7 shows a right side view of the one-piece cartridge body member used in the embodiment shown in FIG. 1;

FIG. 8 shows a front view of the one-piece cartridge body member used in the embodiment shown in FIG. 1;

FIG. 11 shows a side cross-section view of another embodiment of a cartridge lancet device. The device is shown in an initial or retracted position. The spring is not shown in cross-section. This embodiment is similar to that of FIG. 1 except that the one-piece cartridge body member used in the embodiment shown in FIG. 1 is replaced with a two-piece member, i.e., a lancet needle cartridge member coupled to a one-piece member made up of a cylindrical body portion and a back cap portion;

FIG. 12 shows a side cross-section view of another embodiment of a cartridge lancet device. The device is shown in a puncturing position. The spring is not shown in cross-section. This embodiment is similar to that of FIG. 1 except that the cap used in the embodiment shown in FIG. 1 is replaced with a cap having a centrally arranged projection;

FIG. 22 shows a rear view of the embodiment shown in FIG. 20 showing only a portion of the main body in cross-section and showing a rear view of the front cap which together illustrate how the cap can be made to rotate in only one direction;

FIG. 23 shows a side view of the cap used shown in FIG. 22;

FIG. 24 shows a side view of another embodiment of a cartridge lancet device. The device is shown in an initial or retracted position. This embodiment utilizes a front cap which is shown in cross-section, a main body, an axially and rotatably movable back cap which allows the user to position each lancet needle into alignment with the opening of the cap, as well as a spring and a cartridge assembly which are not visible;

FIG. 33 shows a side cross-section view of another embodiment of a cartridge lancet device. The device is shown in an initial or retracted position. This embodiment utilizes a rotatably indexable plunger which positions each needle into alignment with the opening of the front cap, a main body which can be that of any type of device such as a test meter, a removable front cap, and a cartridge assembly which is not shown in cross-section;

FIG. 34 shows a side cross-section view of the embodiment shown in FIG. 33 in the puncturing position;

FIG. 40 shows a side cross-section view of another embodiment of a cartridge lancet device. The device is shown in an initial or retracted position with the front cap removed. This embodiment utilizes a rotatably indexable front cap which allows the user to position the opening over each lancet needle and which includes a spring biased device for moving the back cap to the retracted position, a main body, a spring, a back cap which can be temporarily locked in the retracted position, and a cartridge assembly having a removable installation member which can be broken off the cartridge after it is installed on the plunger;

FIG. 45 shows a side cross-section view of another embodiment of a cartridge lancet device. The device is shown in an initial or retracted position. This embodiment utilizes a rotatably indexable front cap which allows the user to position the opening over each lancet needle, a main body, a spring, a back cap which can be temporarily locked in the retracted position, a spring biased device for moving the back cap to the retracted position and for triggering the device, a cartridge assembly, and a back cover;

FIG. 46 shows a side cross-section view of another embodiment of a cartridge lancet device. The device is shown in an initial or retracted position. This embodiment utilizes a rotatably indexable front cap which allows the user to position the opening over each lancet needle, a main body, a spring, a back cap which can be temporarily locked in the retracted position by a triggering system, a device for moving the back cap to the retracted position, a cartridge assembly, and a back cover;

FIG. 47 shows a side cross-section view of the embodiment of FIG. 46 after the device is triggered to cause the device to assume the puncturing position;

FIG. 48 shows a side cross-section view of another embodiment of a cartridge lancet device with the front cap removed from the body. This embodiment utilizes an axially movable plunger arranged in a main body which can be that of any type of device such as a test meter, a removable front cap having a cartridge assembly mounted thereto so as to be removable and/or replaceable with the front cap and a spring for biasing the cartridge towards a retracted position;

FIG. 52 shows a side cross-section view of another embodiment of a cartridge lancet device with the front cap removed from the body. This embodiment utilizes an axially movable plunger arranged in a main body which can be that of any type of device such as a test meter, a removable front cap having a cartridge assembly mounted thereto so as to be removable and/or replaceable with the front cap, a spring for biasing the cartridge towards a retracted position, and a device for rotatably indexing the cartridge relative to the front cap;

FIG. 55 shows a side view of another embodiment of a cartridge which can be used on a cartridge lancet device. The cartridge of this embodiment utilizes rows of lancet needles arranged on multiple sides of the cartridge and includes axial end openings shown in partial cross-section;

FIG. 56 shows an end view of the cartridge of FIG. 55;

FIG. 57 shows one non-limiting plunger mechanism for mounting the cartridge of FIG. 55 to a device;

FIG. 61 shows a side cross-section view of another embodiment of a cartridge lancet device. The device is shown in a puncturing position. This embodiment is similar to that of FIG. 40 except that the cap and cartridge are differently configured.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
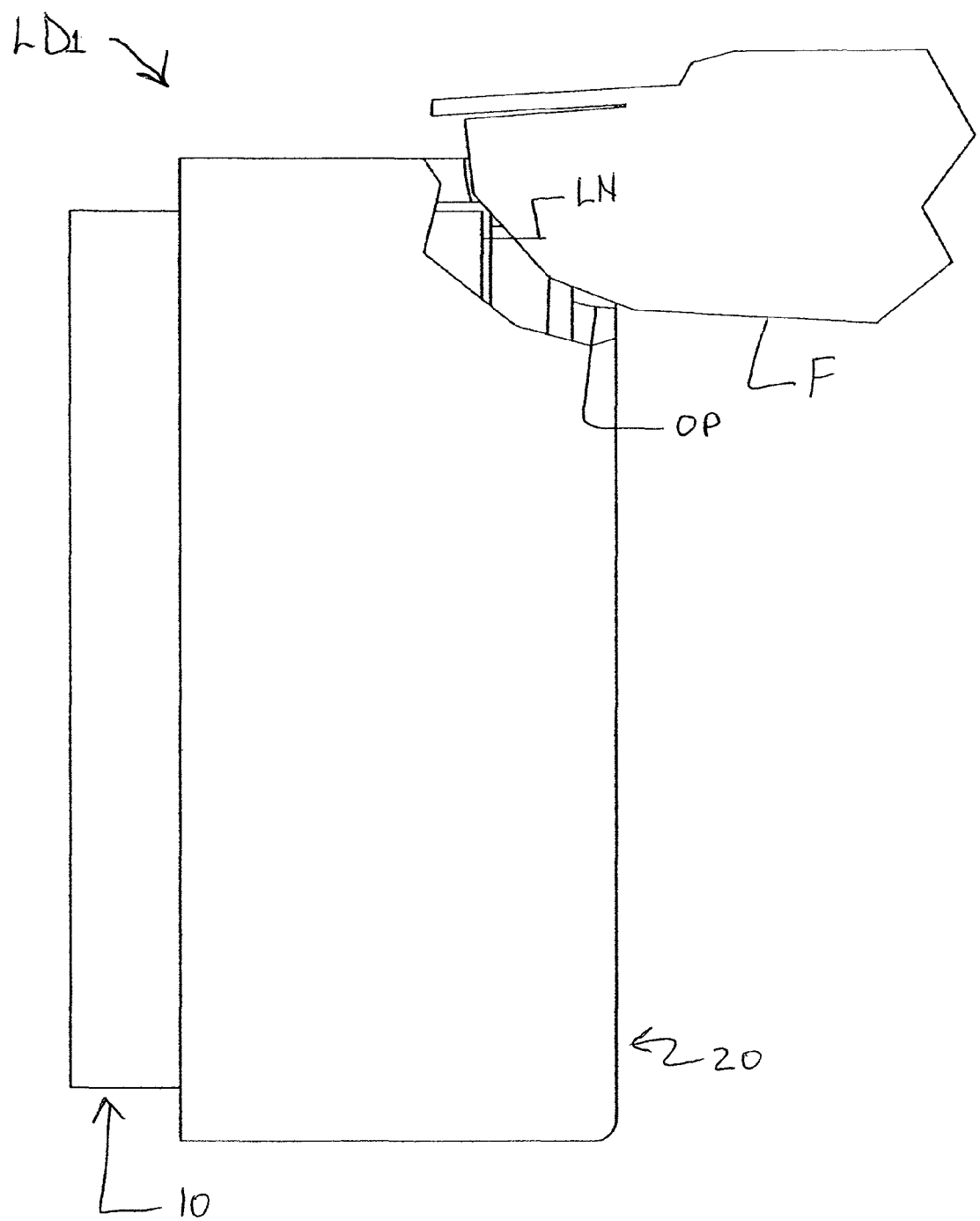
FIG. 1 shows a side view of a first embodiment of a cartridge lancet device in a puncturing position and shows the end portion of a finger of a user being punctured by one of the needles. The cap is shown in partial cross-section.
Figure 2:
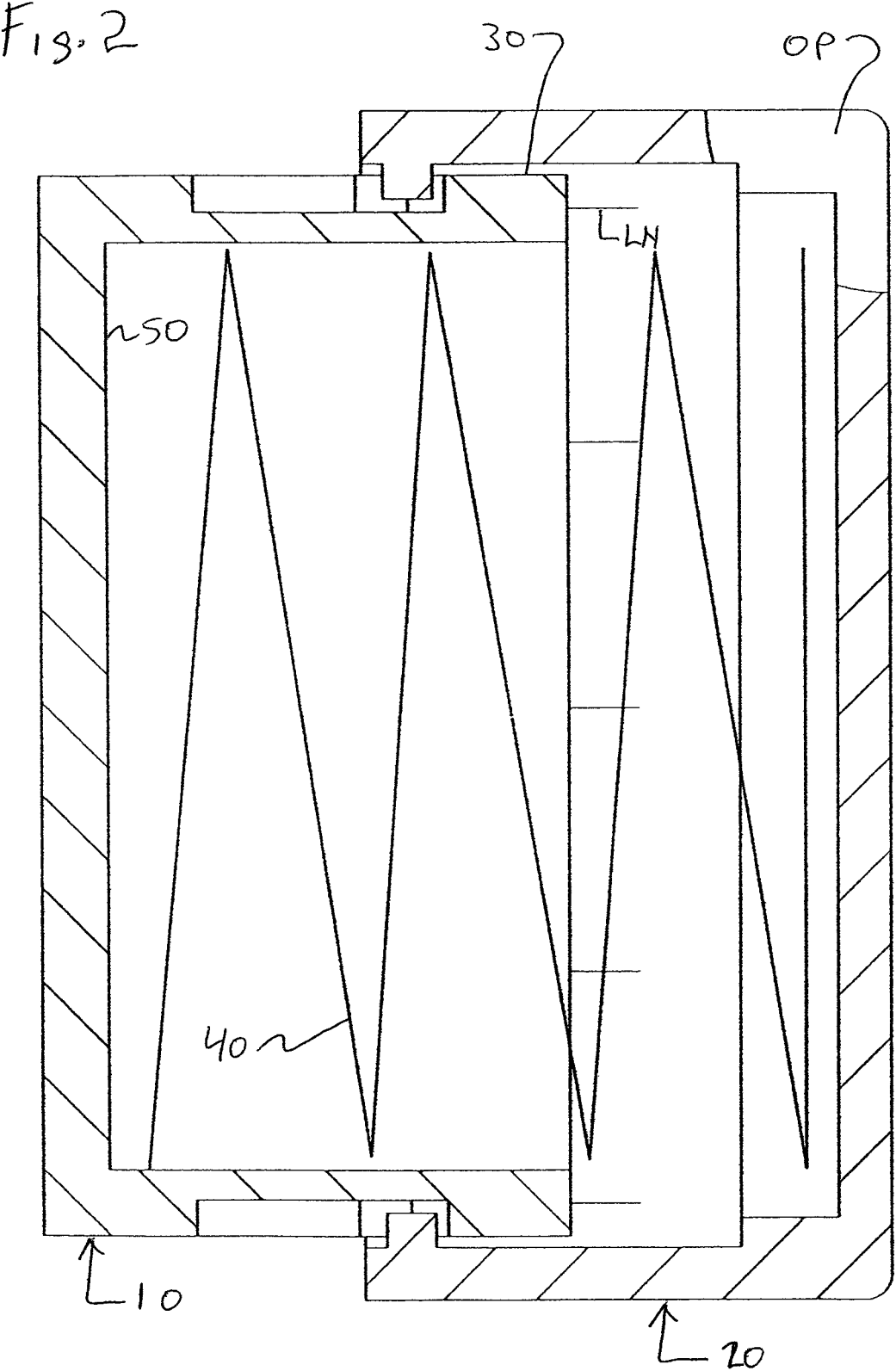
FIG. 2 shows a side cross-section view of the embodiment shown in FIG. 1 with the cartridge lancet device in an initial or retracted position. The spring is not shown in cross-section.

FIGS. 1-10 show a first non-limiting embodiment of a cartridge lancet device $LD_1$ which can be manually triggered by, e.g., a user gripping the device $LD_1$ shown in FIG. 2 between a thumb and index finger of one hand (not shown), placing an index finger F of the other hand into the opening OP (see FIG. 1), and then squeezing the device $LD_1$ with the gripping hand to cause one of the lancet needles LN aligned with the opening OP to penetrate the skin of the finger F as shown in FIG. 1. By way of non-limiting example, the overall diameter of the device can be between about 1 inch and about 4 inches and an axial width (measured in the retracted position shown in FIG. 2) of between about 0.5 inches and about 2 inches. However, it is preferred that the diameter be between about 1.5 and 2 inches and the axial width be about 1 inch.

Figure 3:
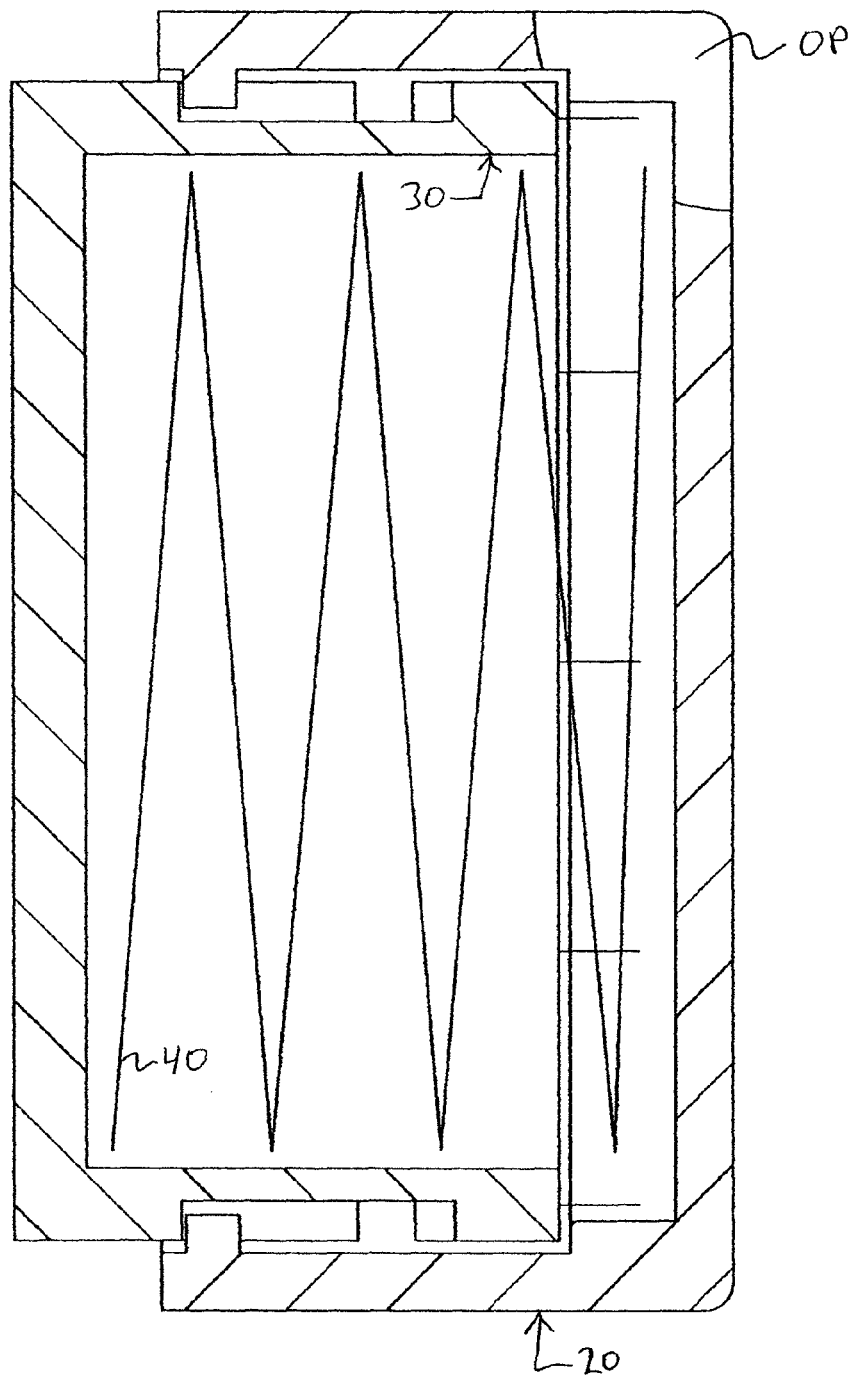
FIG. 3 shows a side cross-section view of the embodiment shown in FIG. 1 with the cartridge lancet device in the puncturing position. The spring is not shown in cross-section.
Figure 4:
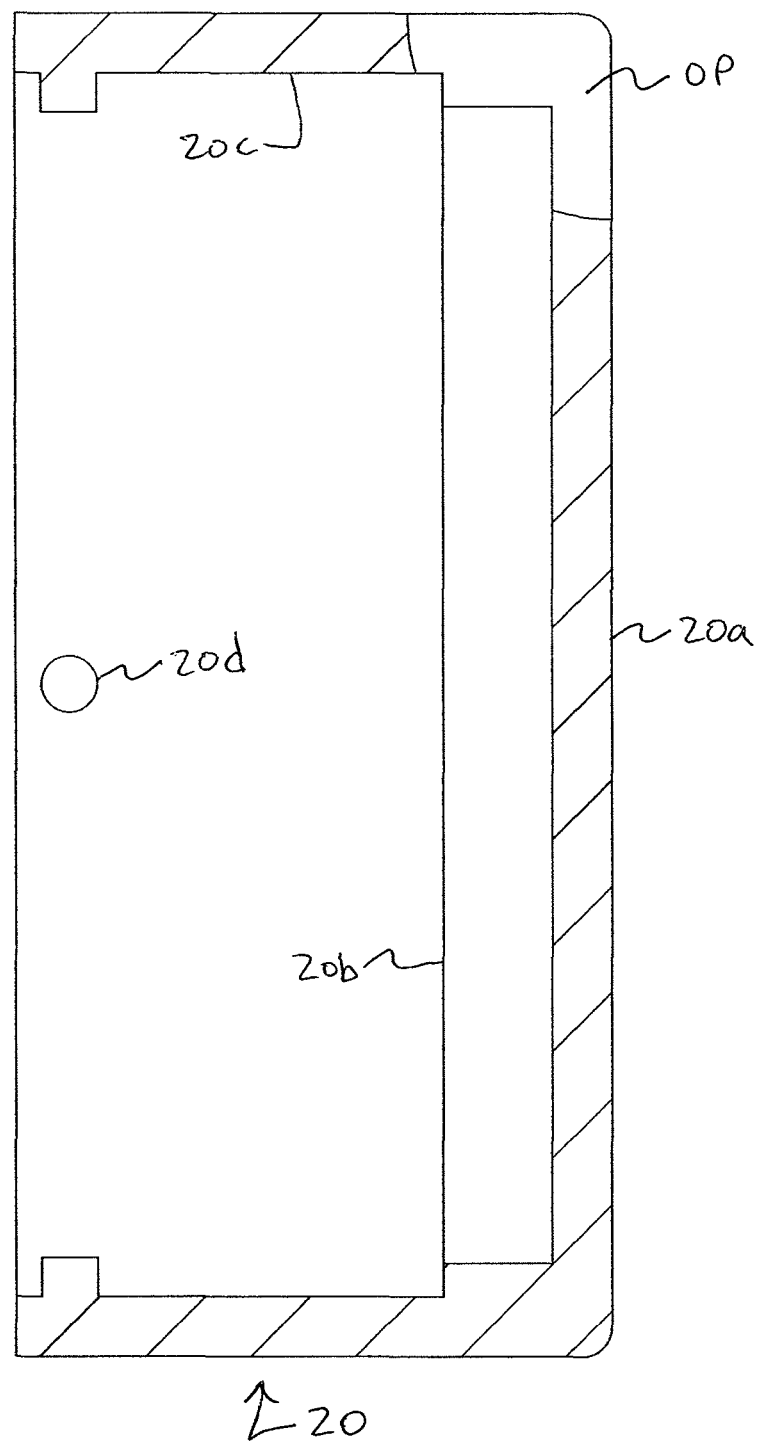
FIG. 4 shows a side cross-section view of the cap or front cap used in the embodiment shown in FIG. 1.
Figure 10:
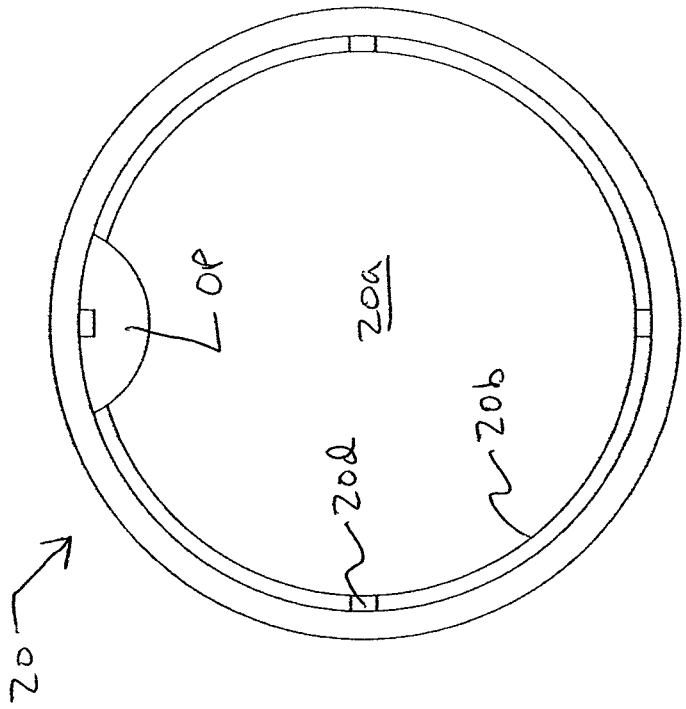
FIG. 10 shows a rear view of the cap shown in FIG. 9.
Figure 9:
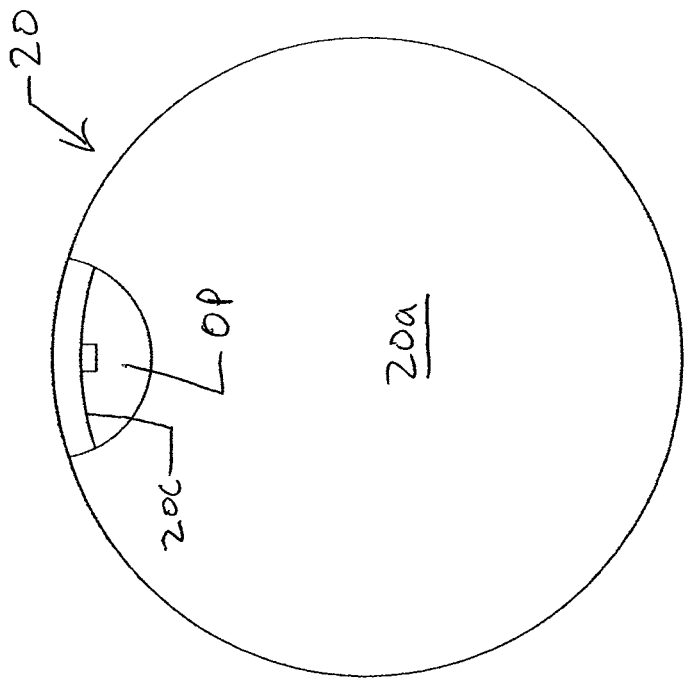
FIG. 9 shows a front view of the cap used in the embodiment shown in FIG. 1.

As is apparent from FIGS. 2 and 3, the device $LD_1$ utilizes a main body 10 and a front cap 20. The main body 10, which can be made as a one-piece synthetic resin member with the exception of the lancet needles LN which can be any metal conventionally used for lancet needles, has a lancet needle cartridge portion 30 arranged at a front end of a generally cylindrical body portion and a rear cap portion 50 arranged at a rear end the cylindrical body portion. The lancet needles LN are preferably oriented generally parallel to a center axis of the device $LD_1$. As can be seen in FIGS. 6 and 7, the cylindrical portion of the main body 10 includes a circumferential groove 10a, a plurality of linear guide grooves 10b, and a plurality of retaining grooves or recesses 10c. As is apparent from FIGS. 4, 9 and 10, the front cap 20 includes an opening OP which can be a semi-circular opening, an annular end portion 20a, a shoulder 20b, a generally cylindrical portion 20c which includes a plurality of equally angularly spaced inward facing and/or radially oriented projections 20d. A compression spring 40 (or other biasing mechanism such as, e.g., an axially compressible ring-shaped rubber member) is utilized to bias the body 10 away from the cap 20 and can be compressed by the relative axial movement of the members 10 and 20 towards each other (compare FIGS. 2 and 3).

The operation of the embodiment shown in FIGS. 1-10 will now be described. Once the cartridge lancet device $LD_1$ is assembled and assumes the initial position shown in FIG. 2, a user can, as described above, use the device $LD_1$ to cause a puncture in the use's finger F as shown in FIG. 1. Then, the user can test the blood sample in any of a variety of ways whether conventional or otherwise. If the user wishes create another puncture in the user's finger within only a few hours, the user can possibly use the device in the same way. If however more than a few hours have expired and/or if the user wishes to use a fresh needle, the user simply rotates the front cap 20 relative to the body 10 until the projections 20d line up and engage with (i.e., snap into) the next adjacent retaining recess 10c. Since the retaining grooves 10c (as well as the guide grooves 10b) are in alignment with the lancet needles LN, this partial rotational movement of the front cap 20 relative to the body 10 positions the opening OP over and/or in alignment with the next adjacent lancet needle LN. At this point, the cartridge lancet device $LD_1$ assumes another position similar to that shown in FIG. 2. The user can once again, as described above, use the device $LD_1$ to cause a puncture in the use's finger F as shown in FIG. 1. This linear axial movement of the cap 20 and body 10 between the position shown in FIG. 2 and that shown in FIGS. 1 and 3 is controlled by sliding engagement between the projections 20d and the guide grooves 10b. This movement can be limited (thereby providing a predetermined penetration depth) by contact between the bottoms of the grooves 10b and the projections 20d or alternatively by contact between the shoulder 20b and the front end of the cartridge 30. The above steps are repeated until all of the lancet needles LN are used.

Although not shown, the device can utilize a system which prevents backward rotation (i.e., a one-way rotation system) of the front cap 20 relative to the body 10 in order to prevent the user from reusing a lancet needle LN. Furthermore, to ensure that the user is made aware (i.e., visually) that the lancet needle LN (which will soon be used) is in fact a fresh needle, the device can also or alternatively utilize a coating layer applied to the bottom of each groove 10b—which layer is scraped or removed by a scraping action of one of the projections 20d. Once all of the grooves 10b show evidence of having the coating removed (or at least partially scraped away), the user will know that the device has been fully used, and no longer has any fresh or unused needles LN.

Once all of the needles LN are used for puncturing, the user can simply discard the device $LD_1$ without fear of others being accidentally punctured with contaminated needles. By providing the opening as an indented opening, by arranging the opening OP in a corner area of the front cap 20, and by biasing the front cap 20 and body 10 away from each other, it becomes difficult to cause a puncture in any user's skin by accident. Furthermore, the arrangement shown in FIGS. 1-10 results in a relatively inexpensive lancet device, especially when one considers the number of times one can use the device, i.e., at least as many times as there are needles. In this regard, the invention contemplates using as few as two lancet needles LN or as many as 20 or more with any whole number between 2 and 20 (odd or even) being specifically contemplated by the invention, i.e., 2, 3, 4, 5 . . . 20.

FIG. 11 shows another embodiment of a cartridge lancet device. The device $LD_2$ is shown in an initial or retracted position. This embodiment is similar to that of FIG. 1 except that the one-piece cartridge body member used in the embodiment shown in FIG. 1 is replaced with two-piece member, i.e., a separately formed lancet needle cartridge member 30 coupled to a one-piece body member made up of a cylindrical body portion 10 and a back cap portion 50. The lancet needle cartridge member 30 can be coupled to a front portion of the cylindrical body portion 10 via frictional engagement and/or a non-removable connection such as ultrasonic welding or adhesive bonding.

FIG. 12 shows another embodiment of a cartridge lancet device. The device $LD_3$ is shown in a puncturing position. This embodiment is similar to that of FIG. 1 except that the cap used in the embodiment shown in FIG. 1 is replaced with a cap 20' having a centrally arranged projection 20'e instead of the shoulder 20b used in the embodiment shown in FIG. 1. The projection 20'e is utilized to limit the axial movement of the cap 20' and body 10 during puncturing by virtue of the rear end of the projection 20'e contacting the wall 50. This movement can alternatively be limited (thereby providing a predetermined penetration depth) by contact between the bottoms of the grooves 10b and the projections 20'd.

Figure 13:
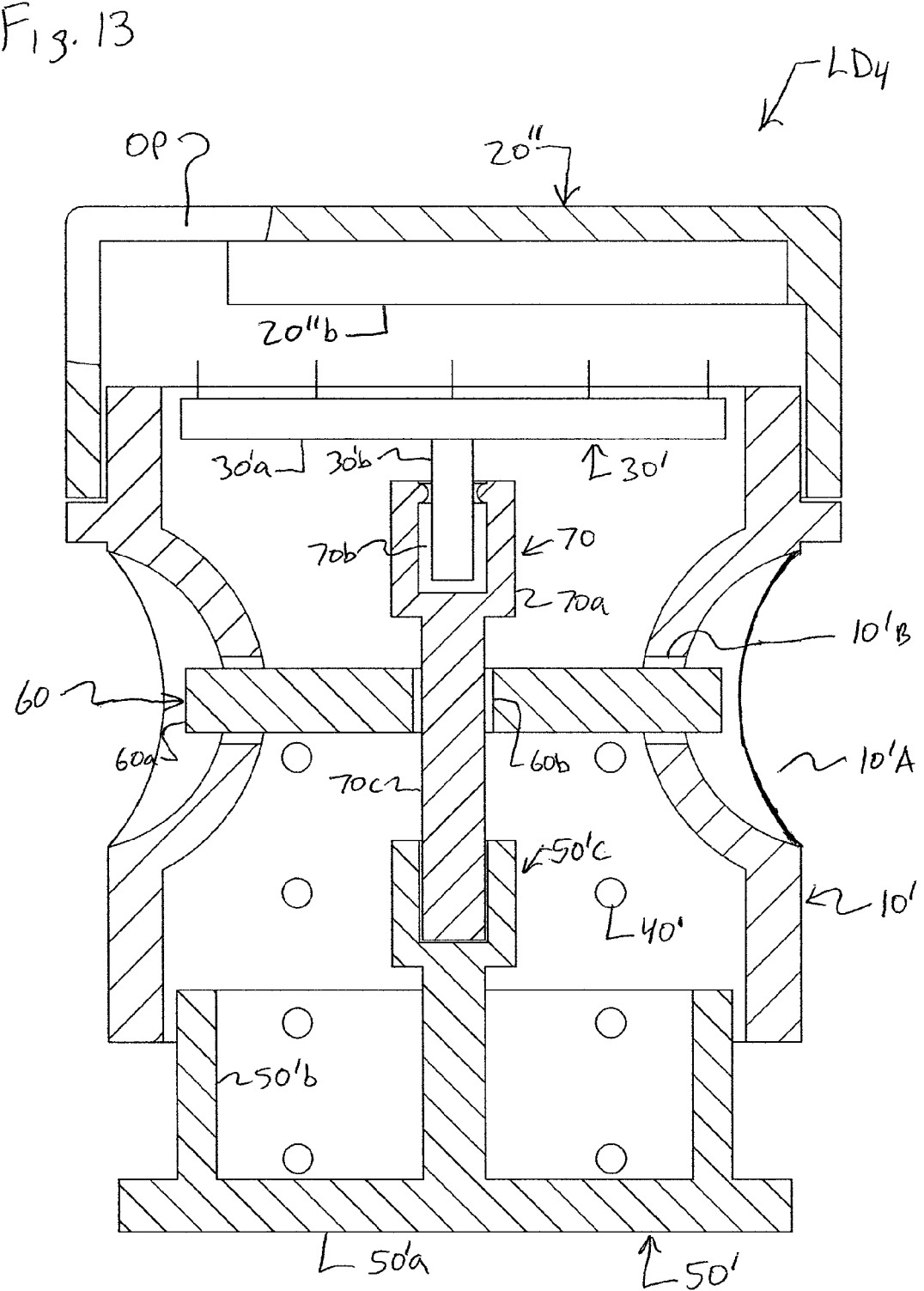
FIG. 13 shows a side cross-section view of another embodiment of a cartridge lancet device. The device is shown in an initial or retracted position. This embodiment utilizes a front cap, a main body, an axially movable back cap, a spring, a rotatable thumb wheel which allows the user to position each needle into alignment with the opening in the cap, a rotatable plunger, and a cartridge assembly which is not shown in cross-section.
Figure 14:
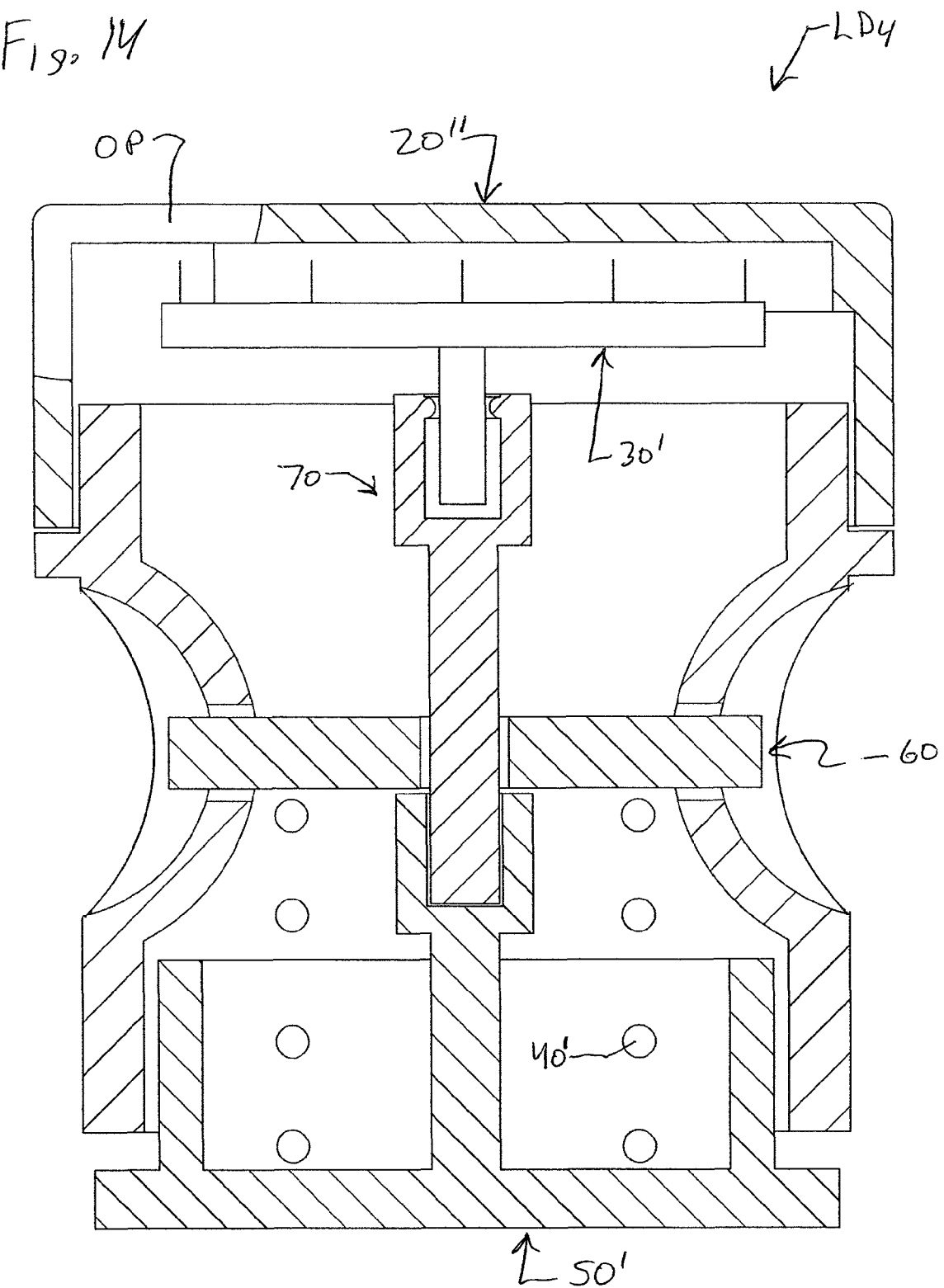
FIG. 14 shows a side cross-section view of the embodiment shown in FIG. 13 with the cartridge lancet device in a puncturing position.
Figure 15:
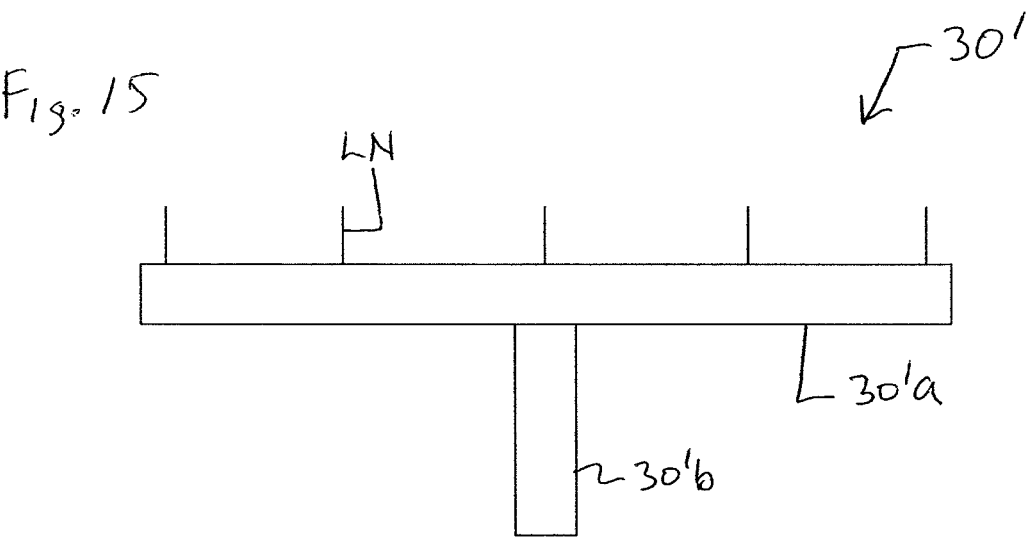
FIG. 15 shows a side view of the cartridge assembly used on the embodiment shown in FIG. 13.
Figure 16:
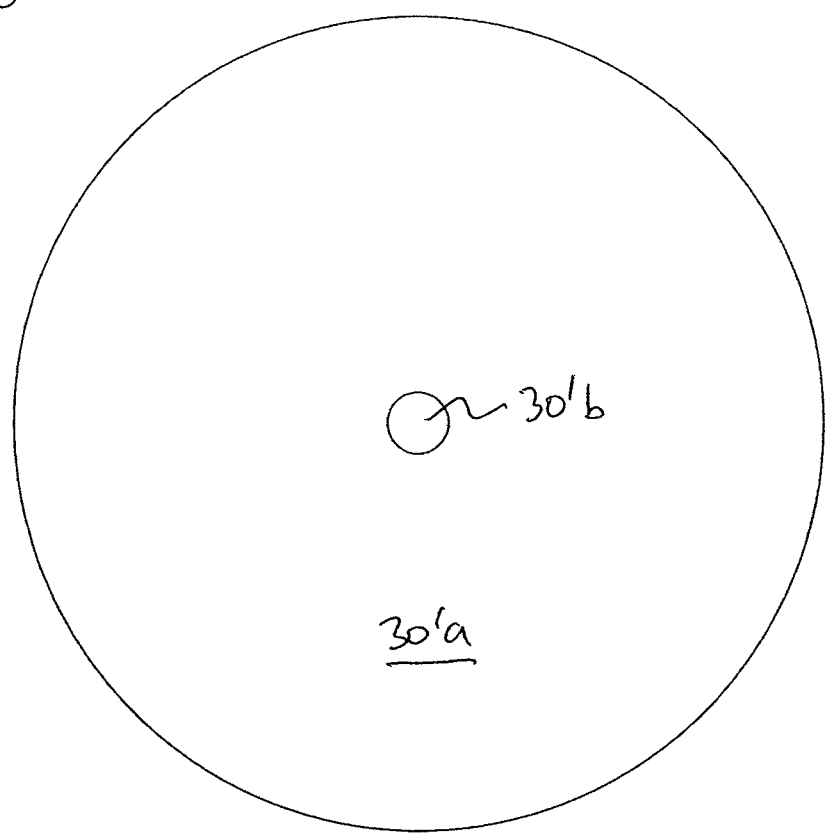
FIG. 16 shows a bottom view of the cartridge assembly shown in FIG. 15.

FIGS. 13-16 show another embodiment of a cartridge lancet device. FIG. 13 shows the device $LD_4$ in an initial or retracted position and FIG. 14 shows the device $LD_4$ in a puncturing position. This embodiment utilizes a front cap 20", a main body 10', an axially movable back cap 50', a compression spring 40', a rotatable thumb wheel 60 which allows the user to position each needle LN into alignment with the opening OP in the cap 20", a rotatable plunger 70, and a cartridge assembly 30'.

The body 10' has a generally cylindrical shape and includes oppositely arranged indentations 10'A which allow the user to access an outer circumference 60a (which can include a high-friction surface such, e.g., as a knurl) of the thumb wheel 60 with the user's fingers thereby allowing the user to rotate the thumb wheel 60 in either a clockwise or counterclockwise direction. The indentations 10'A include slots 10'B which allow portions of the thumb wheel 60 to extend into the indentations 10'A and which also function to limit axial movement (and/or axially retain) of the thumb wheel 60. Such movement of the thumb wheel 60 allows the user to position a fresh needle LN into alignment with the opening OP. The thumb wheel 60 also includes a central arranged opening which is sized to allow axial movement of the plunger 70, i.e., the opening 60b has a shape, e.g., square-shaped, which corresponds to the shape of portion 70c of the plunger 70. Thus, rotation of the thumb wheel 60 causes rotation of the plunger 70. The plunger 70 also includes a front portion 70a which has an opening 70b sized to receive therein (and frictionally engage with) a mounting portion 30'b of the cartridge 30' and a rear end which frictionally engages with (and/or which can be non-removably connected with) a projecting portion 50'c of the back cap 50'. The back cap 50' is biased away from the axially retained thumb wheel 60 using a compression spring 40'. The cartridge 30' has a generally circular-shaped and/or disk-shaped body 30'a having one side from which a plurality of lancet needles LN project, e.g., 8 needles LN, and another opposite facing side from which a generally centrally arranged mounting portion 30'b projects. The needles LN are preferably arranged like a circular bolt hole pattern and/or like numbers on a clock face, i.e., they are arranged at the same radial distance from a center axis of the cartridge 30' and are circumferentially spaced apart by equal angles and/or distances. For example, in a cartridge 30' having eight needles, each needle would be angularly spaced by an angle equal to 360 degrees divided by 8 (the number of needles), i.e., 45 degrees.

The operation of the embodiment shown in FIGS. 13-16 will now be described. Once the cartridge lancet device $LD_4$ is assembled and assumes the initial position shown in FIG. 13, a user can use the device $LD_4$ to cause a puncture in the use's finger in a manner similar to that shown in FIG. 1. If the cartridge 30' requires replacement, the user can first begin by removing the cap 20" and then the cartridge 30' and then installing a new cartridge 30' onto the plunger 70. Removal of the cartridge 30' can optionally take place (after removal of the cap 20") by depressing the back cap 50' and then gripping the side of the cartridge 30', and pulling it off of the plunger 70. Then, the user can test the blood sample in any of a variety of ways whether conventional or otherwise. The lancet device $LD_4$ can be manually triggered by, e.g., a user gripping the device $LD_4$ shown in FIG. 13 in the palm of one hand (not shown), placing an index finger of the other hand into the opening OP, and then pressing down on the back cap 50' with the thumb of the gripping hand to cause one of the lancet needles LN aligned with the opening OP to penetrate the skin of the finger. By way of non-limiting example, the overall diameter of the device can be between about 1 inch and about 2 inches and an axial width (measured in the retracted position shown in FIG. 13) of between about 1.5 inches and about 4 inches. However, it is preferred that the diameter be between about 1.5 inches and the axial width be about 2 inches. If the user wishes create another puncture in the user's finger within only a few hours, the user can possibly use the device in the same way. If however more than a few hours have expired and/or if the user wishes to use a fresh needle, the user simply rotates the thumb wheel 60 relative to the body 10' to another rotational pre-set position. Although not shown, this indexing movement can be provided using the configuration shown in FIG. 38. At this point, the cartridge lancet device $LD_4$ assumes another position similar to that shown in FIG. 13. The user can once again, as described above, use the device $LD_4$ to cause a puncture in the use's finger. This linear axial movement of the back cap 50' and body 10' between the position shown in FIG. 13 and that shown in FIG. 14 can be limited (thereby providing a predetermined penetration depth) by contact between the portion 50'c and the thumb wheel 60 or alternatively by contact between the shoulder 20"b and the front end of the cartridge 30'. The above steps are repeated until all of the lancet needles LN are used.

Figure 17:
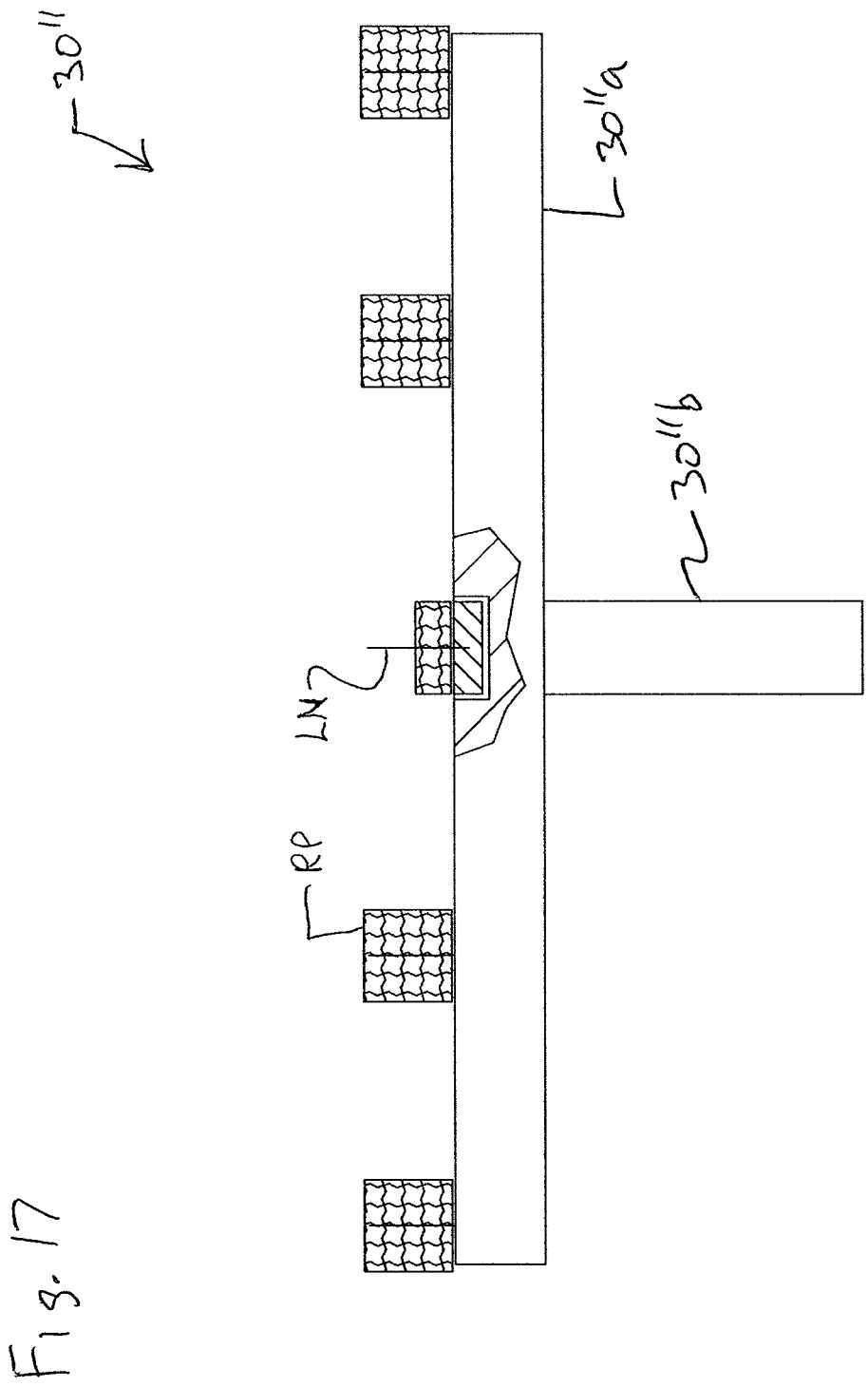
FIG. 17 shows a side view of another embodiment of a cartridge assembly which can be used on embodiments of the type shown in FIG. 13. This embodiment utilizes a cartridge body, a plurality of lancet needle members mounted in blind openings in the body and a plurality of retractable protection members which protect the needles from contamination prior to use.

FIG. 17 shows another embodiment of a cartridge or cartridge assembly 30" which can be used on embodiments of the type shown in FIG. 13. This embodiment utilizes a cartridge body 30"a, a plurality of lancet needle members having body portions and lancet needles LN and which are mounted in blind openings in the body 30"a. The cartridge 30" also includes a plurality of retractable protection members RP which protect the needles LN from contamination prior to use. Non-limiting materials for the protection members RP include silicone or rubber type materials which are typically used in medical devices such as, e.g., lancet devices, syringes, etc., provided they are able to keep the needles LN in substantially sterile condition while in an expanded state. In FIG. 17, one of the lancet needles has its member RP compressed to illustrate how the needle LN is exposed (by contact with a user's finger) when the needle LN is in a puncturing position.

Figure 18:
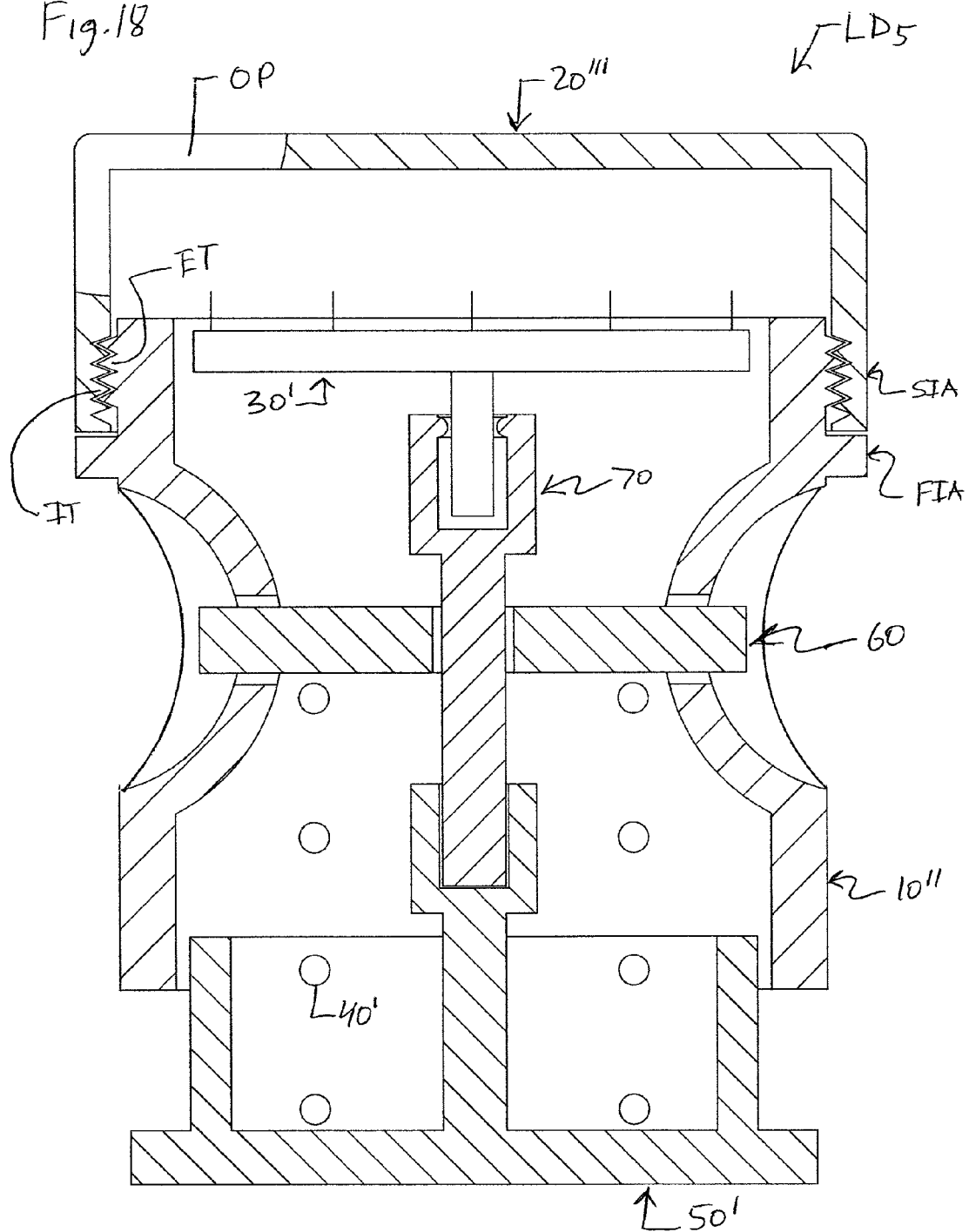
FIG. 18 shows a side cross-section view of another embodiment of a cartridge lancet device. The device is shown in an initial or retracted position. This embodiment is similar to that of FIG. 13 except that it utilizes a removable thread-on front cap which can also provide depth of penetration adjustment.
Figure 19:
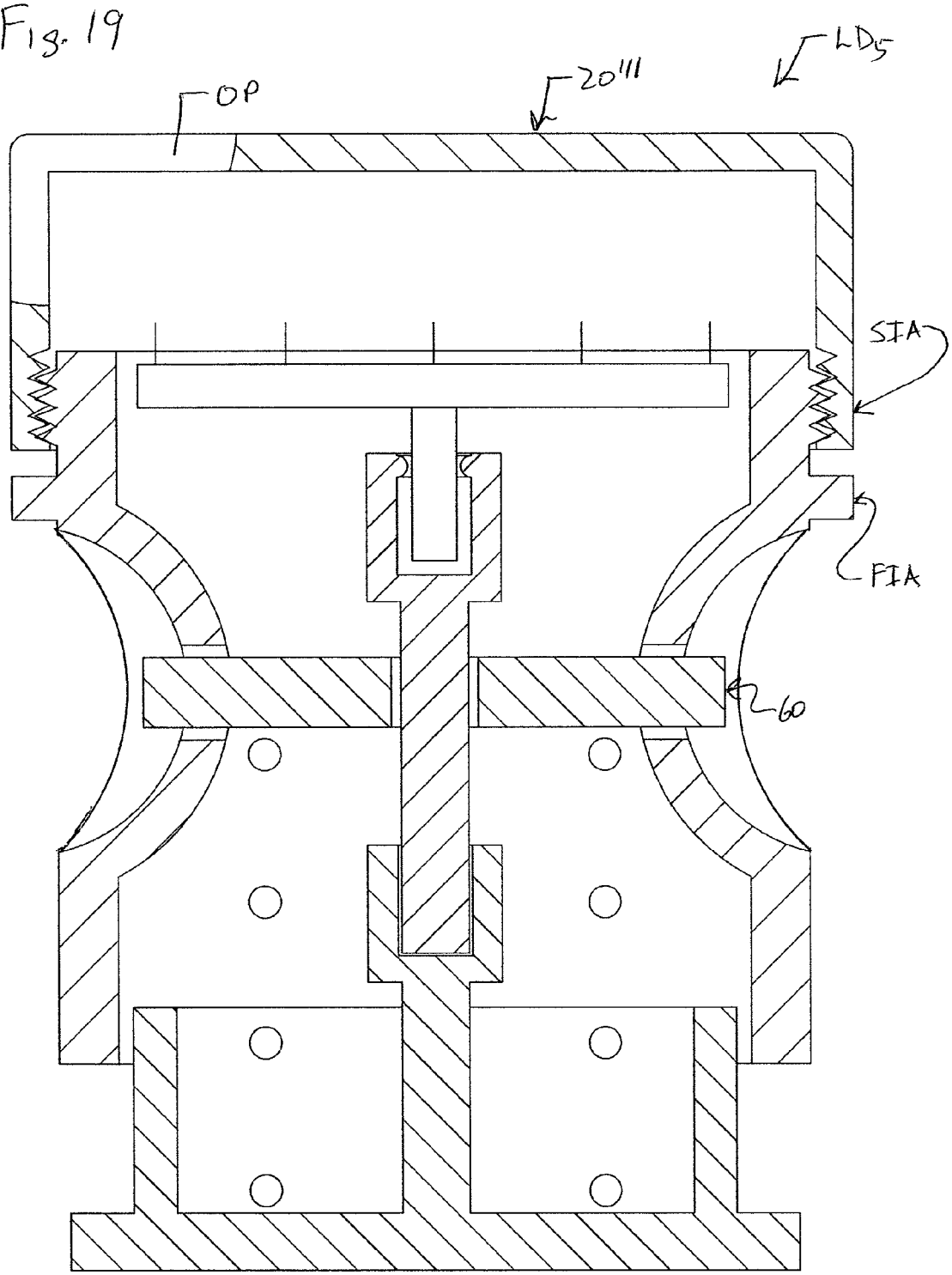
FIG. 19 shows a side cross-section view of the embodiment shown in FIG. 18 with the cap being positioned in a different or shallower depth of penetration adjustment position.

FIGS. 18 and 19 show another embodiment of a cartridge lancet device. In FIG. 18, the device $LD_5$ is shown in an initial or retracted position but with the cap 20''' in one of plural axial positions. In FIG. 19, the device $LD_5$ is shown in an initial or retracted position but with the cap 20''' in another of plural axial positions. This embodiment is similar to that of FIG. 13 except that it utilizes a removable thread-on front cap 20''' which has internal threads IT that engage with external threads ET of the body 10'' and which can also provide depth of penetration adjustment. A first indicia area FIA is arranged on the body 10'' and a second indicia area SIA is arranged on the cap 20'''. These indicia can be in the form of a single indicator (e.g., projection, recess, number, letter, symbol, etc.) in area FIA and a plurality of indicia in area SIA which provide an indication to the user of the depth of penetration. Once a desired depth setting is reached, the user can use the device $LD_5$ in the same way as was described with regard to the embodiment shown in FIG. 13. Preferably, for this embodiment, the user should not attempt to again adjust the device $LD_5$ until the cartridge 30' is replaced with another new one. FIG. 19 shows the embodiment shown in FIG. 18 with the cap 20''' being positioned in a shallower depth of penetration adjustment position.

Figure 20:
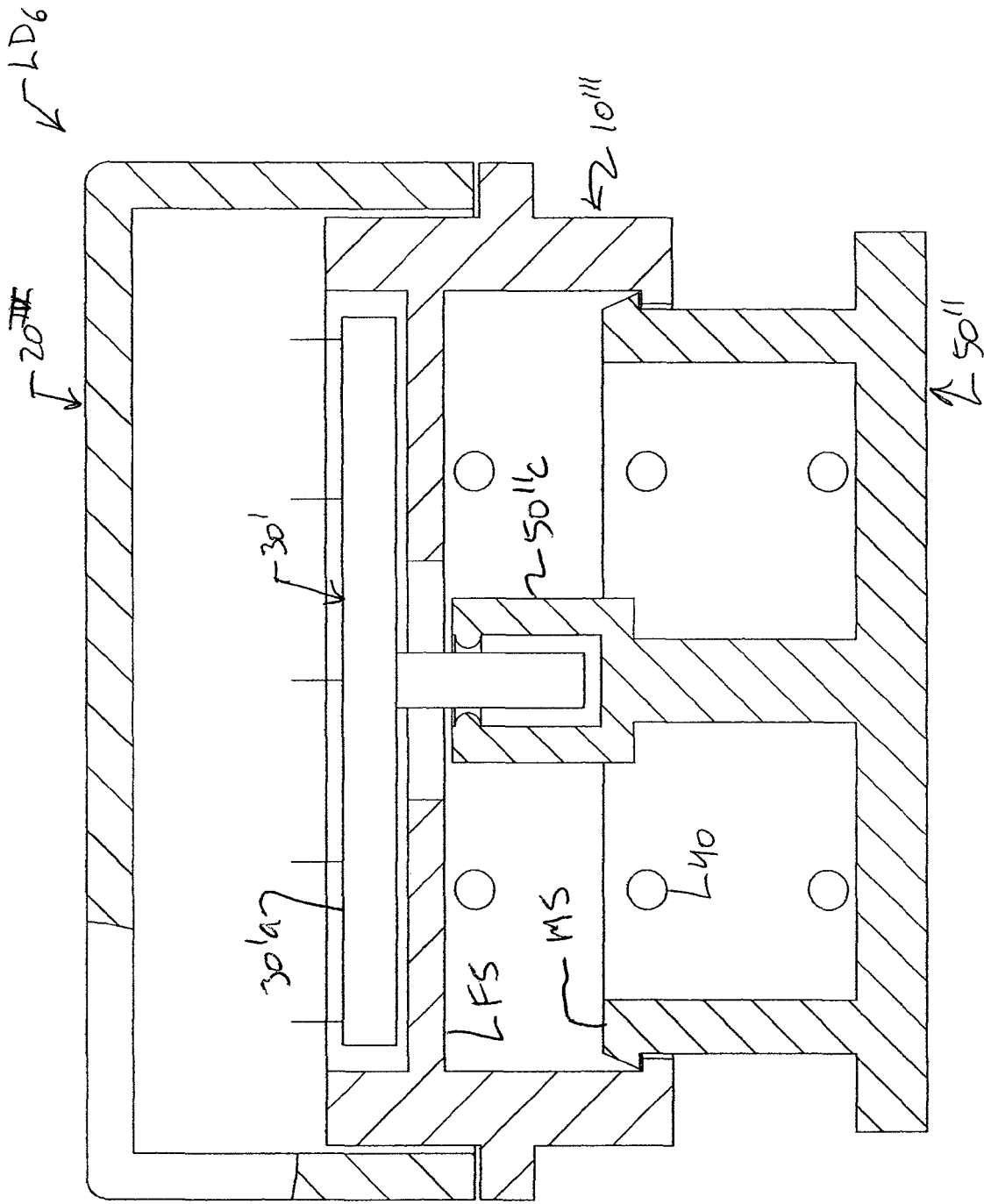
FIG. 20 shows a side cross-section view of another embodiment of a cartridge lancet device. The device is shown in an initial or retracted position. This embodiment utilizes a front cap which allows the user to position the opening into alignment with each lancet needle, a main body, an axially movable back cap, a spring, and a cartridge assembly which is not shown in cross-section.
Figure 21:
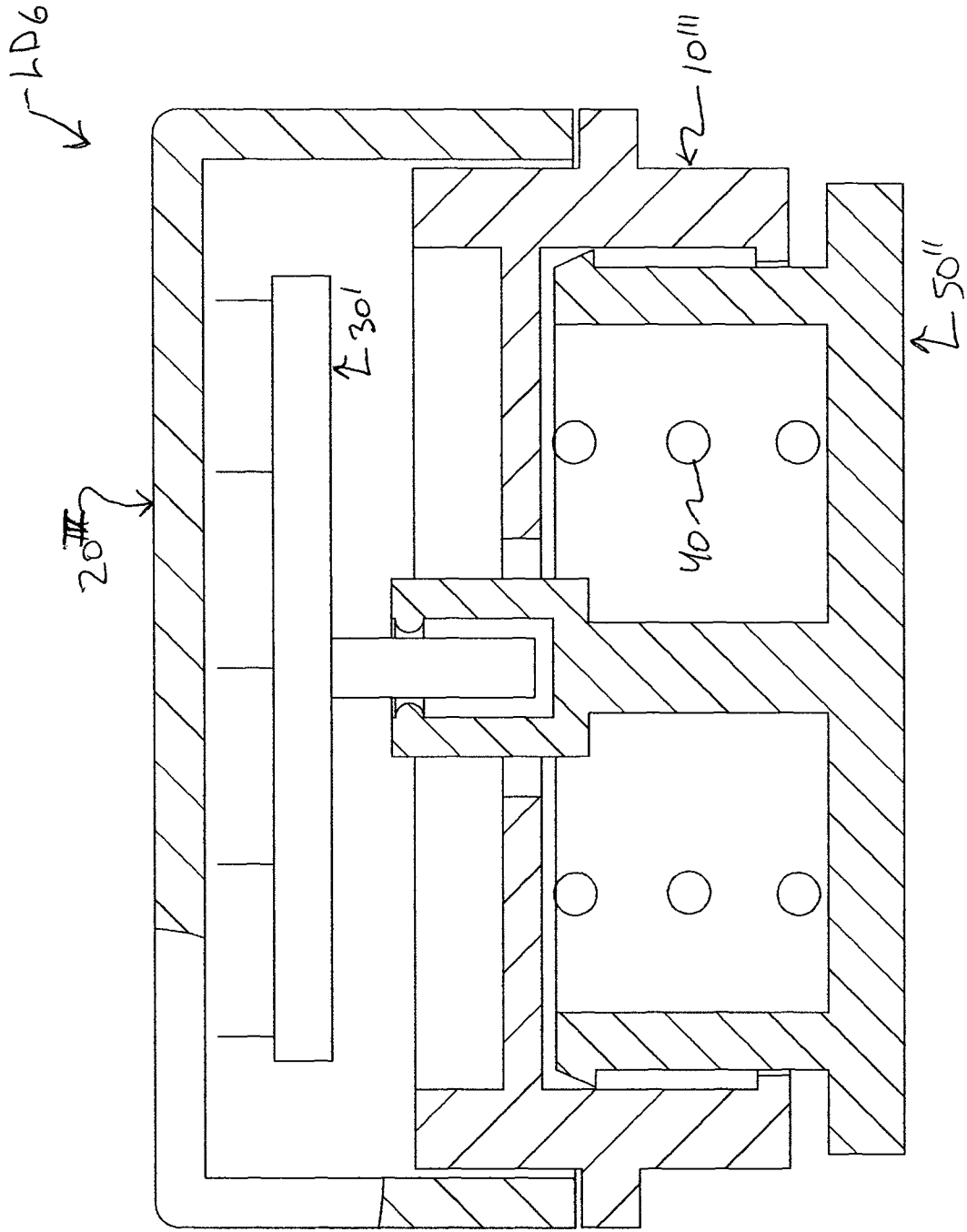
FIG. 21 shows a side cross-section view of the embodiment shown in FIG. 20 with the cartridge lancet device in the puncturing position.

FIGS. 20-23 show another embodiment of a cartridge lancet device. In FIG. 20, the device $LD_6$ is shown in an initial or retracted position and in FIG. 21, the device $LD_6$ is shown in a puncturing position. This embodiment utilizes a front cap $20^{IV}$ which allows the user to position the opening OP into alignment with each lancet needle LN by rotating the front cap $20^{IV}$ relative to a main body 10''', an axially movable back cap 50'', a compression spring 40 similar or identical to that used in the embodiment of FIG. 1, and a cartridge assembly 30' of the type described above.

The operation of the embodiment shown in FIGS. 20-23 will now be described. Once the cartridge lancet device $LD_6$ is assembled and assumes the initial position shown in FIG. 20, a user can use the device $LD_6$ to cause a puncture in the use's finger. If the cartridge 30' requires replacement, the user can first begin by removing the cap $20^{IV}$ and then the cartridge 30', and then installing a new cartridge 30' onto the pushing portion 50''c. Removal of the cartridge 30' can optionally take place (after removal of the cap $20^{IV}$) by depressing the back cap 50'' and then gripping the side of the cartridge 30', and pulling it off of the portion 50''c. Then, the user can test the blood sample in any of a variety of ways whether conventional or otherwise. The lancet device $LD_6$ can be manually triggered in substantially the same way as that shown in FIG. 1. If the user wishes create another puncture in the user's finger within only a few hours, the user can possibly use the device in the same way. If however more than a few hours have expired and/or if the user wishes to use a fresh needle, the user simply rotates the cap $20^{IV}$ relative to the body 10''' to another rotational pre-set position. This indexing movement and one-way rotation movement can be provided and/or ensured using the configuration shown in FIGS. 22 and 23, i.e., utilizing deflectable projections DP on the cap $20^{IV}$ and ratchet teeth RT on the body 10'''. At this point, the cartridge lancet device $LD_6$ assumes another position similar to that shown in FIG. 20. The user can once again, as described above, use the device $LD_6$ to cause a puncture in the use's finger. The linear axial movement of the back cap 50'' relative to the body 10''' between the position shown in FIG. 20 and that shown in FIG. 21 can be limited (thereby providing a predetermined penetration depth) by contact between the forward end of the portion 50'c and the thumb wheel 60 or alternatively by contact between a movable surface MS and a fixed surface FS. The above steps are repeated until all of the lancet needles LN are used. Embodiments such as this one can utilize cartridges 30' which have different body 30'a thicknesses in order to provide different depth of penetrations. For example, a cartridges 30' having a body 30'a thickness of 1/16 inches (with all other dimensions being the same) would produce a shallower puncture than one having a body 30'a thickness of 1/8 inches.

FIG. 24 shows another embodiment of a cartridge lancet device. The device $LD_7$ is shown in an initial or retracted position. This embodiment utilizes a front cap $20^{IV}$ which can be non-removably connected (via locking projections LP and a locking recess LR) to a body $10^{IV}$, as well as an axially and rotatably movable back cap 50''' which allows the user to position each lancet needle LN into alignment with the opening OP of the cap $20^{IV}$, as well as a spring 40 and a cartridge 30' which are not visible. The device also utilizes a locating projection LPR which engages with a number of guide recesses similar to the embodiment shown in FIGS. 25-27 which be described further below.

Figure 25:
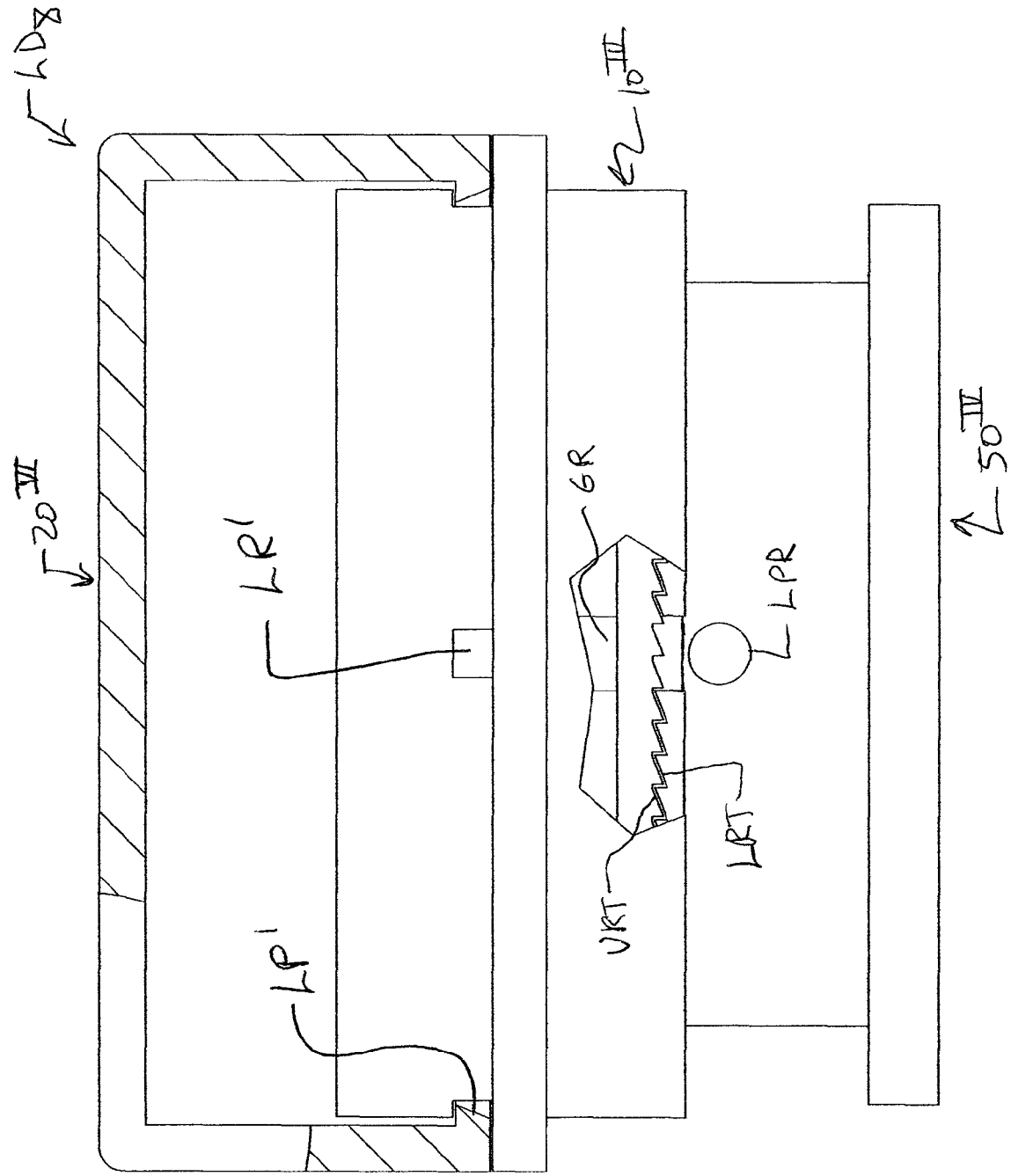
FIG. 25 shows a side view of another embodiment of a cartridge lancet device. The device is shown in an initial or retracted position. This embodiment is similar to that of FIG. 24 except that it utilizes a cap which is non-rotatably mounted to the main body.
Figure 26:
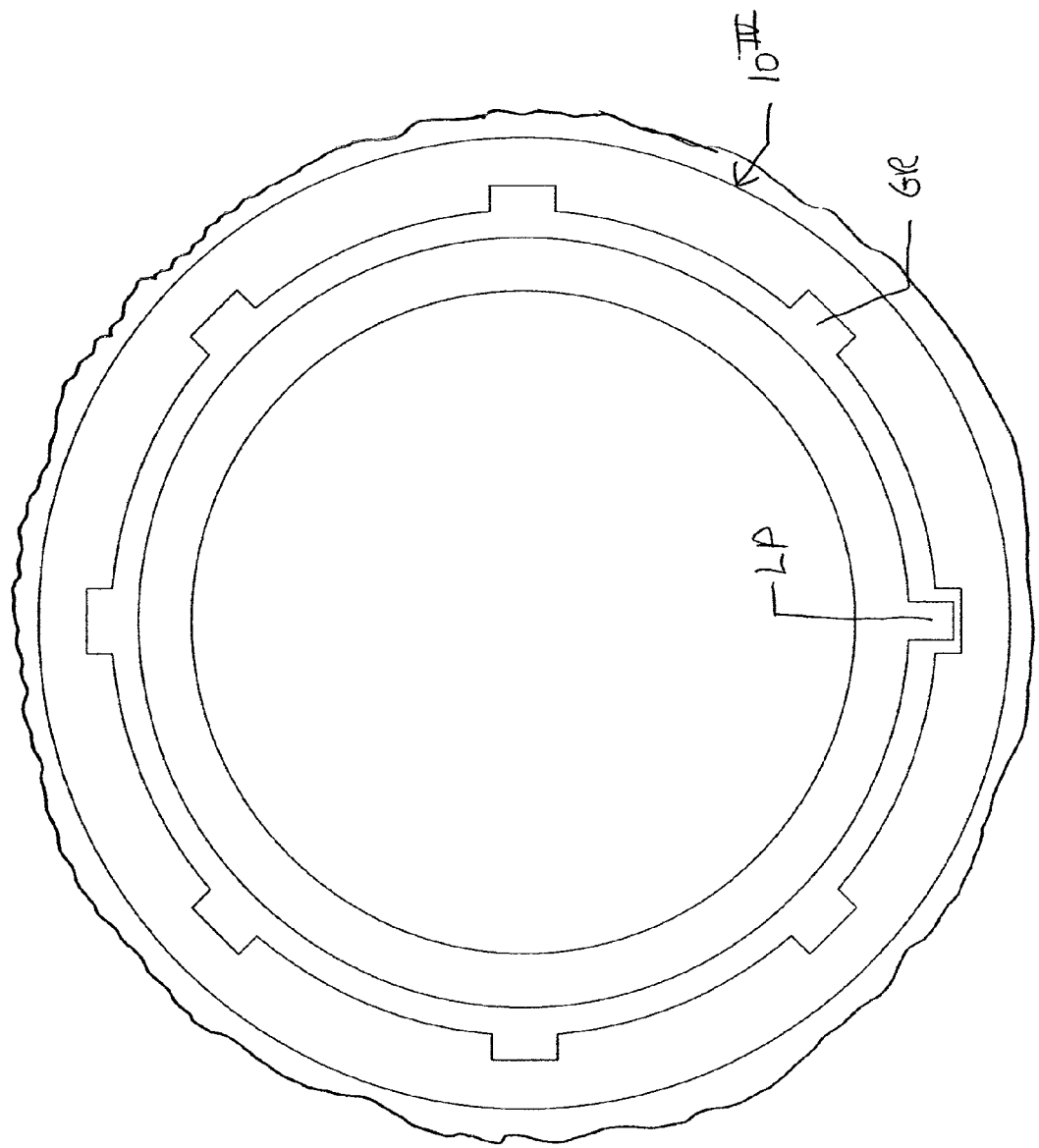
FIG. 26 shows a front view of portions of the body and back cap of the embodiment shown in FIG. 25 and illustrates the mechanisms which ensure that the back cap can only move axially towards the puncturing position when back cap is rotated to predetermined positions which correspond to positions wherein a lancet needle is aligned with the opening in the front cap.
Figure 27:
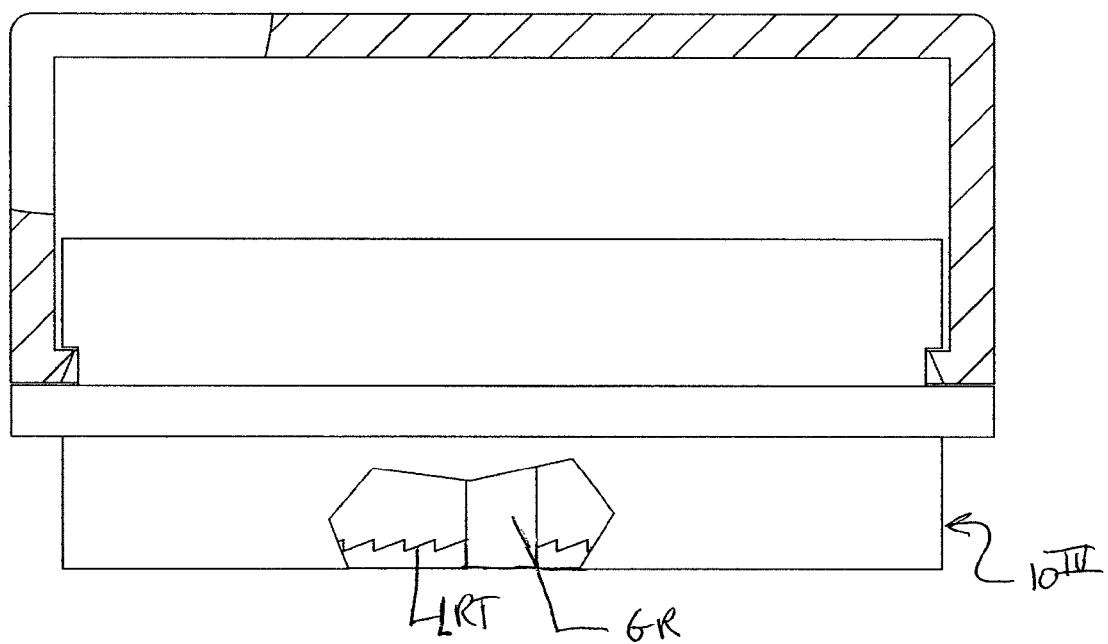
FIG. 27 shows a side view of the body and front cap (which is shown in cross-section) of the embodiment shown in FIG. 25 positions wherein a lancet needle is aligned with the opening in the front cap.
Figure 28:
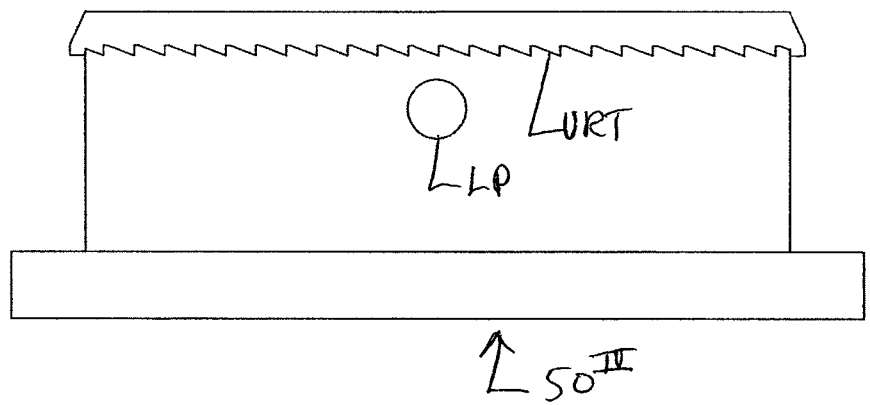
FIG. 28 shows a side view of the back cap and spring used in the embodiment shown in FIG. 25.

FIGS. 25-28 show another embodiment of a cartridge lancet device. In FIG. 25, the device $LD_8$ is shown in an initial or retracted position. This embodiment is similar to that of FIG. 24 except that it utilizes a cap $20^{IV}$ which is non-rotatably and non-rotatably mounted to the main body $10^{IV}$ via locking projections LP' and locking recesses LR'. An axially and rotatably movable back cap $50^{IV}$ is utilized which allows the user to position each lancet needle LN into alignment with the opening OP of the cap $20^{VI}$, as well as a spring 40 and a cartridge 30' (not shown). The device also utilizes a locating projection LPR which engages with a number of guide recesses GR (i.e., one for each lancet needle LN). This ensures that the back cap $50^{IV}$ moves axially into the body $10^{IV}$ only when the projection LPR is aligned with one of the recesses GR. A one-way rotation system is provided to ensure that the back cap $50^{IV}$ rotates relative to the body $10^{IV}$ in only one direction. This system includes upper ratchet teeth URT and lower ratchet teeth LRT. The spring 40 ensures that these teeth URT and LRT engage each other when the back cap $50^{IV}$ is in the position shown in FIG. 25.

Figure 29:
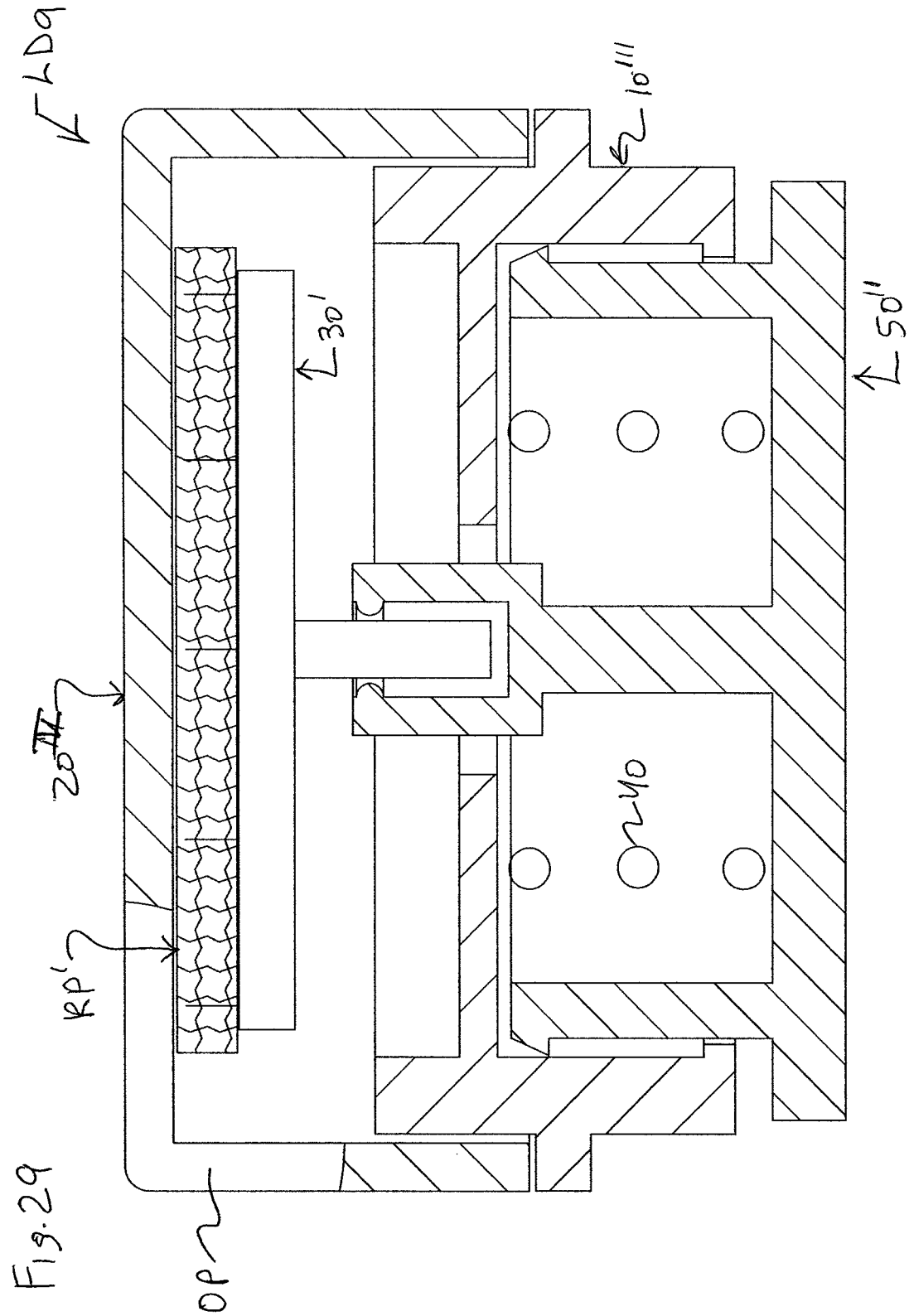
FIG. 29 shows a side cross-section view of another embodiment of a cartridge lancet device. The device is shown in a puncturing position. This embodiment utilizes a rotatably indexable front cap which allows the user to position the opening over each lancet needle, a main body, an axially movable back cap, a spring, and a cartridge assembly having a retractable protection member.

FIG. 29 shows another embodiment of a cartridge lancet device. In FIG. 29, the device $LD_9$ is shown in a puncturing position. This embodiment is similar to the embodiment shown in FIG. 20 except that it utilizes a disk-shaped retractable protection member RP' protecting all of the lancet needles LN. The member RP' can be made of the same material as was described above with regard to the protection member RP. Of course, the member RP' can be used on any of the other herein disclosed device embodiments which utilize a disk-shaped cartridge similar to that shown in FIGS. 15-17.

Figure 30:
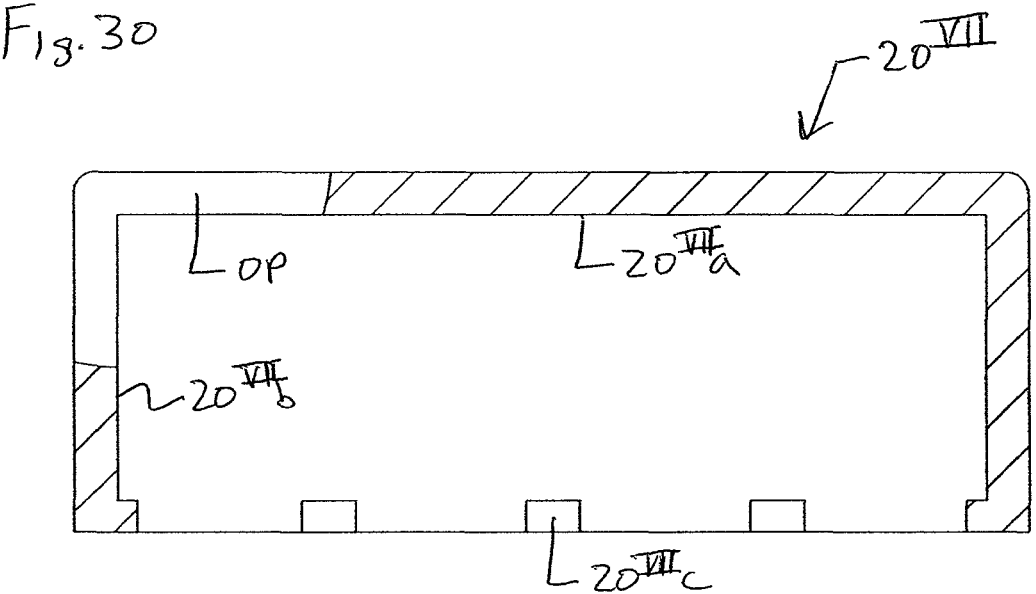
FIG. 30 shows a side cross-section view of a front cap which can be used in another embodiment of a cartridge lancet device whose other components are shown in FIG. 31.
Figure 31:
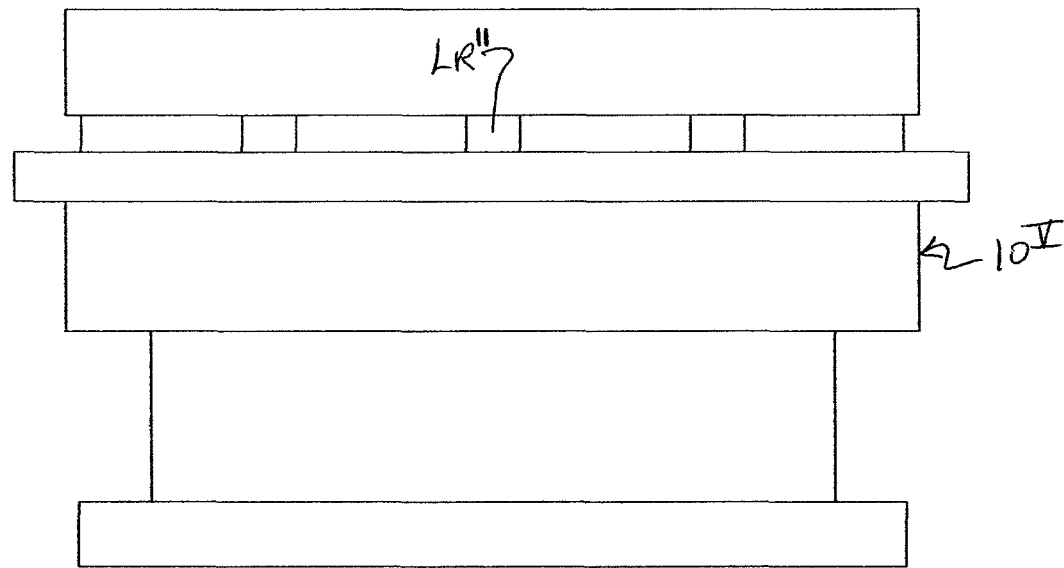
FIG. 31 shows a side view of the main body and back cap used in an embodiment of a cartridge lancet device that utilizes the front cap of FIG. 30.
Figure 32:
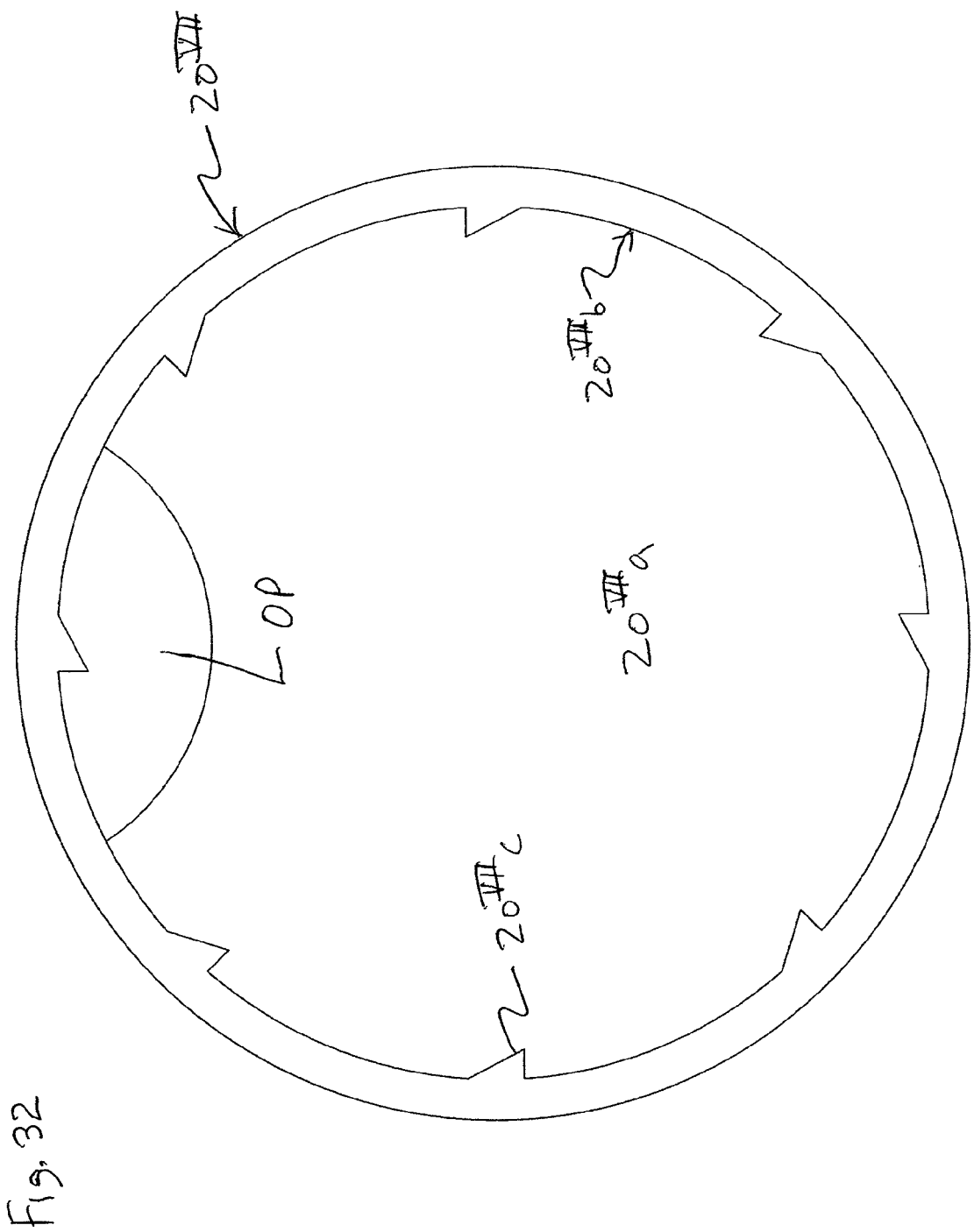
FIG. 32 shows a read view of a front cap shown in FIG. 30.

FIGS. 30-32 show another embodiment of a cartridge lancet device $LD_{10}$. The body $10^V$ can be similar to the body 10''' shown in FIG. 20 except that it includes locking recesses LR'' arranged in a circumferential groove which are engaged by a plurality of tapered locking projections $20^{VII}c$ of the cap $20^{VII}$. As is evident in FIG. 32, the interaction of the locking recesses LR'' and the locking projections $20^{VII}c$ ensure that the cap $20^{VII}$ can rotate relative to the body $10^V$ in only one direction and ensure that the cap $20^{VII}$ is retained in a plurality of rotational positions which correspond to an alignment of the opening OP with each of the lancet needles LN. The cap $20^{VII}$ also includes an annular skin engaging portion $20^{VII}a$, a generally cylindrical section $20^{VII}b$, and an opening OP. The back cap 50'' can be similar to the back cap shown in FIG. 20. The cylindrical section $20^{VII}b$ of the cap $20^{VII}$ can also utilize axially oriented slots between the projections $20^{VII}c$ to ensure that the projections $20^{VII}c$ deflect more easily when the cap $20^{VII}$ is rotated.

FIGS. 33 and 34 show another embodiment of a cartridge lancet device. In FIG. 33, the device $LD_{11}$ is shown in an initial or retracted position. In FIG. 34, the device $LD_{11}$ is shown in a puncturing or extended position. This embodiment utilizes a rotatably indexable plunger 700 which positions each needle into alignment with the opening OP of the front cap 200, a main body 100 which can be that of any type of device such as, e.g., a test meter. The cartridge 300 can be of the same type shown in FIGS. 15 and 16.

The operation of the embodiment shown in FIGS. 33 and 34 will now be described. Once the cartridge lancet device LD is assembled and assumes the initial position shown in FIG. 33, a user can use the device $LD_{11}$ to cause a puncture in the use's finger by causing the device $LD_{11}$ to assume the position shown in FIG. 34. If the cartridge 300 requires replacement, the user can first begin by removing the cap 200 and then the cartridge 300, and then installing a new cartridge 300 onto the plunger portion 700. Although not shown, the mounting portion of the cartridge 300 can be shaped to correspond to the mounting opening of the plunger 700 in order to ensure that the cartridge 300 is properly rotationally aligned upon installation, i.e., one of the lancet needles LN is properly aligned with the opening OP. Removal of the cartridge 300 can optionally take place (after removal of the cap 200) by depressing or activating a system (not shown) which moves the plunger 700 to the position shown in FIG. 34 and then gripping the side of the cartridge 300, and pulling it off of the plunger 700. After one of the lancet needles LN is used to puncture a user's finger, the user can test the blood sample in any of a variety of ways whether conventional or otherwise. The lancet device $LD_{11}$ can be triggered again. The device can function in the following non-limiting ways; one option is for the device to cause (via an electrical or electronic system and a motor) the plunger 700 to first rotate to the next rotational position which aligns the next adjacent lancet needle LN with the opening OP and then move axially to the position shown in FIG. 34. Another option is for the user to grip and rotate the cap 200 to the next rotational position and then cause a triggering of the device. This indexing movement and one-way rotation movement can be provided and/or ensured using a configuration similar to that shown in FIGS. 22 and 23, i.e., utilizing deflectable projections on the cap and ratchet teeth on the body. It is also possible for this embodiment to utilize penetration depth adjustment by using an electronic system which regulates the axial movement of the plunger 700. The above steps are repeated until all of the lancet needles LN are used. Embodiments such as this one can also utilize cartridges 300 which have different body thicknesses in order to provide different depth of penetrations.

Figure 35:
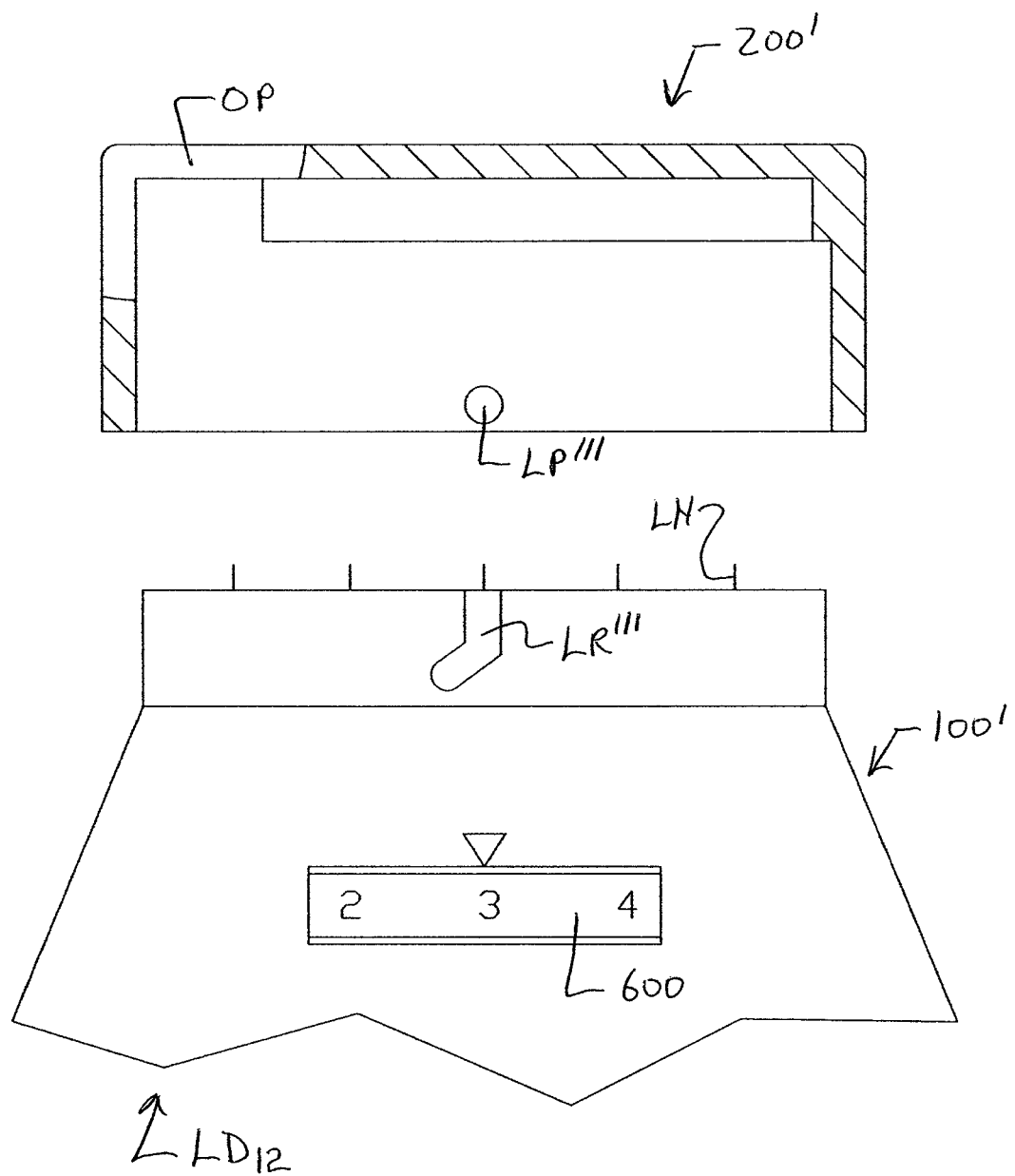
FIG. 35 shows a side view of another embodiment of a cartridge lancet device. This embodiment is similar to that of FIG. 33 except that it utilizes a rotatably indexable thumb wheel to rotate the plunger and position each needle into alignment with the opening of the front cap (which is shown in cross-section) and arrangement for locking the front cap onto the body in a predetermined position.

FIG. 35 shows another embodiment of a cartridge lancet device $LD_{12}$. This embodiment is similar to that of FIG. 33 except that it utilizes a rotatably indexable thumb wheel 600 to manually rotate the plunger 700 (similar to the system shown in FIGS. 36-38) and position each needle LN into alignment with the opening OP of the front cap 200' and arrangement for locking the front cap 200' onto the body 100' in a predetermined position. This arrangement utilizes one or more locking projections LP''' and one or more locking recesses LR'''.

Figure 36:
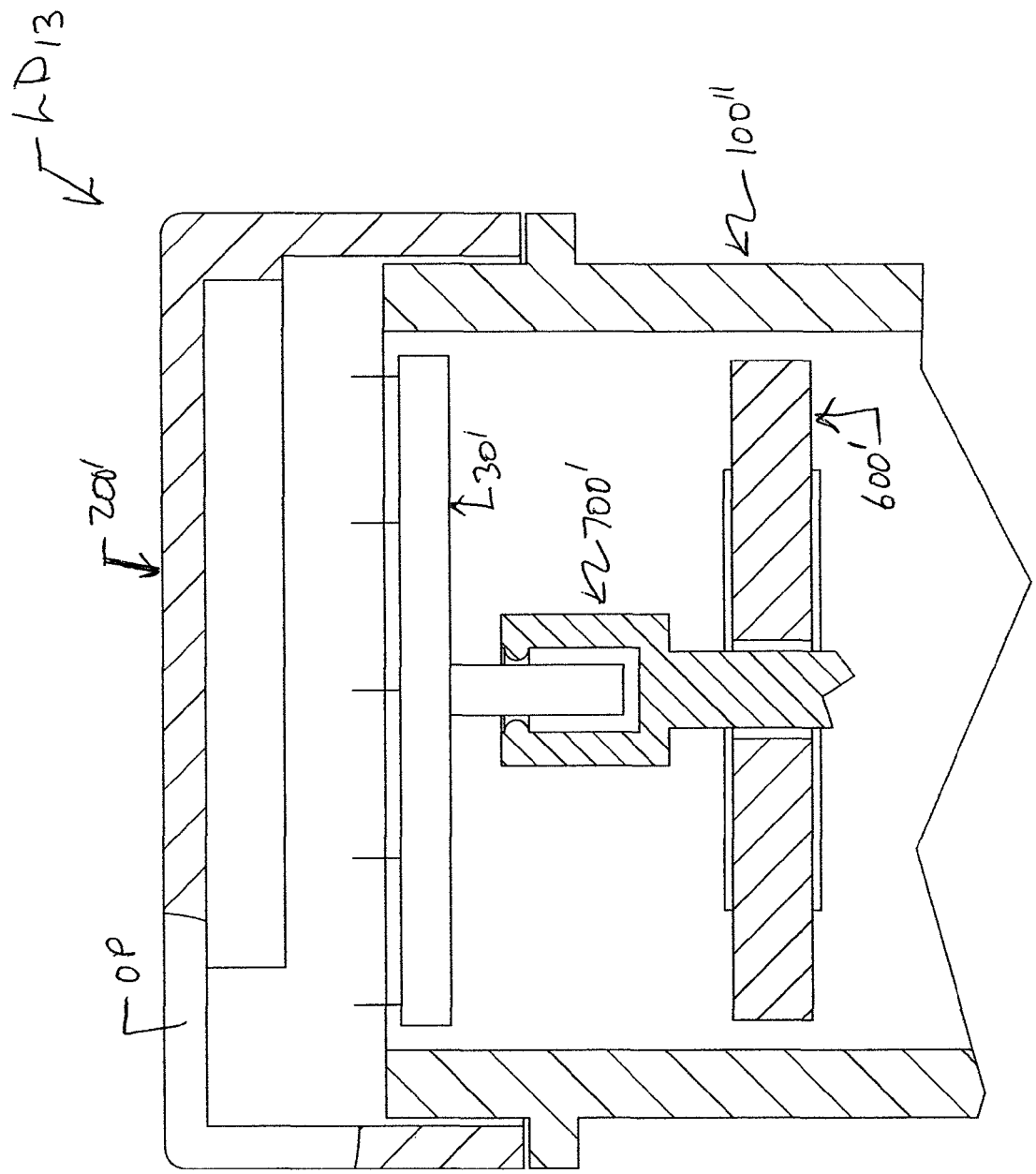
FIG. 36 shows a side cross-section view of another embodiment of a cartridge lancet device. The device is shown in an initial or retracted position. This embodiment utilizes a rotatably indexable thumb wheel to rotate the plunger and position each needle into alignment with the opening of the front cap (which is shown in cross-section), a main body which can be that of any type of device such as a conventional lancet device, a removable front cap, and a cartridge assembly which is not shown in cross-section.
Figure 37:
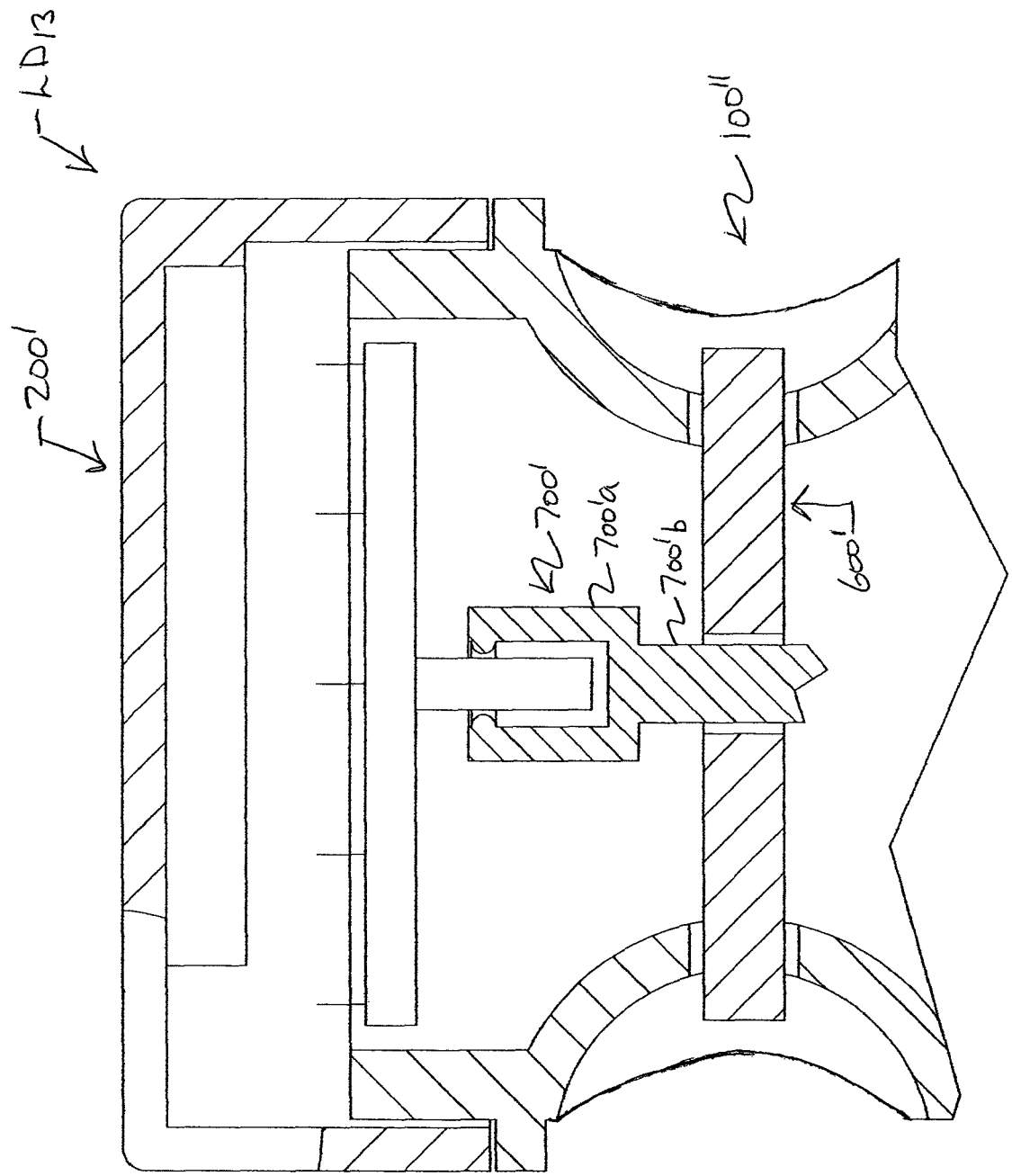
FIG. 37 shows another side cross-section view of the embodiment shown in FIG. 36 with the device rotated 90 degrees.
Figure 38:
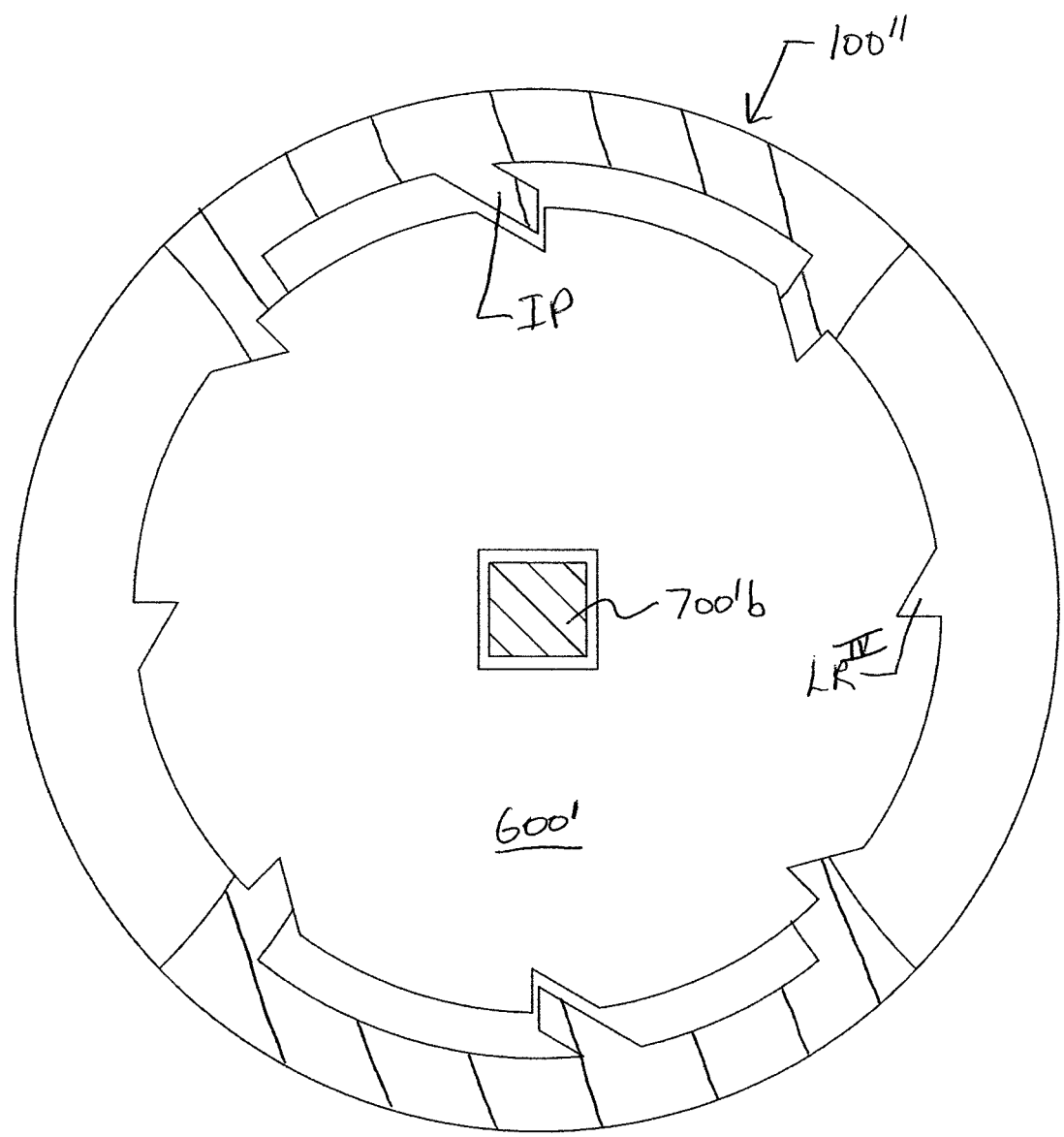
FIG. 38 shows a top cross-section view of the embodiment shown in FIG. 36 and shows how the thumb wheel can be retained in various predetermined positions and allowed to rotate in only one direction, as well as how portions of the thumb wheel project into recesses of the body to allow a user to rotate the thumb wheel.

FIGS. 36-38 show another embodiment of a cartridge lancet device. In FIG. 36, the device $LD_{13}$ is shown in an initial or retracted position. This embodiment utilizes a rotatably indexable thumb wheel 600' to rotate the plunger 700' and position each needle LN into alignment with the opening OP of the front cap 200'. The main body 100'' can be that of any type of device such as a conventional lancet device. The cartridge 30' can preferably be of the type shown in FIGS. 15 and 16. As is shown in FIG. 37, the body 100'' can utilize side indentations having slots similar to those used in the embodiment of shown in FIG. 13 in order to allow a user to access the thumb wheel 600'. FIG. 38 shows one non-limiting way in which the thumb wheel 600' can be retained in various predetermined rotational positions, via engagement between deflectable indexing projections IP and locking recesses $LR^{IV}$, and allowed to rotate in only one direction, as well as how portions of the thumb wheel 600' project into the recesses of the body 100'' to allow a user to rotate the thumb wheel 600'.

Figure 39:
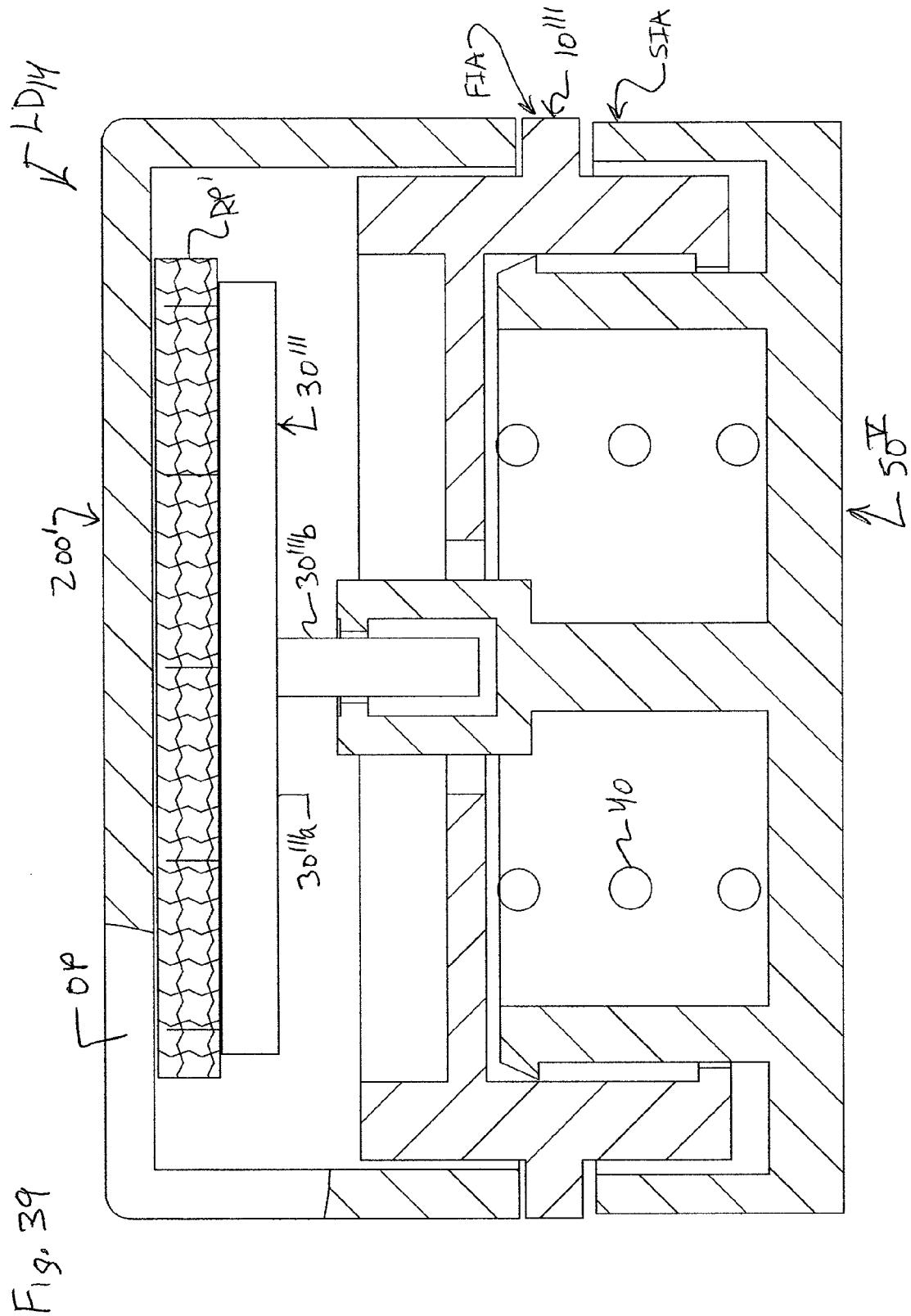
FIG. 39 shows a side cross-section view of another embodiment of a cartridge lancet device. The device is shown in a puncturing position. This embodiment utilizes a rotatably indexable and axially movable back cap which allows the user to position each lancet needle into alignment with the opening in the front cap, a main body, a front cap, a spring, and a cartridge assembly having a retractable protection member.

FIG. 39 shows another embodiment of a cartridge lancet device. The device $LD_{13}$ is shown in a puncturing position. This embodiment utilizes a rotatably indexable and axially movable back cap $50^V$ which allows the user to position each lancet needle LN into alignment with the opening OP in the front cap 200', a main body 10''', a spring 40, and a cartridge assembly 30''' having a retractable protection member RP' which is generally disk-shaped. A first indicia area FIA is arranged on the body 10''' and a second indicia area SIA is arranged on the back cap $50^V$. These indicia can be in the form of a single indicator (e.g., projection, recess, number, letter, symbol, etc.) in area FIA and a plurality of indicia in area SIA which provide an indication to the user of the depth of penetration. Once a desired depth setting is reached, the user can use the device $LD_{14}$ in the same way as was described with regard to the embodiment shown in FIG. 29. The front cap 200' can be mounted to the body 10''' so that it cannot be removed and/or rotated in order to make the device usable only a limited number of times, i.e., until all of the lancet needles LN are used up, or can be removable to as to allow the user to remove and replace the cartridge 30''' with a new cartridge after all of the lancet needle have been utilized.

Figure 41:
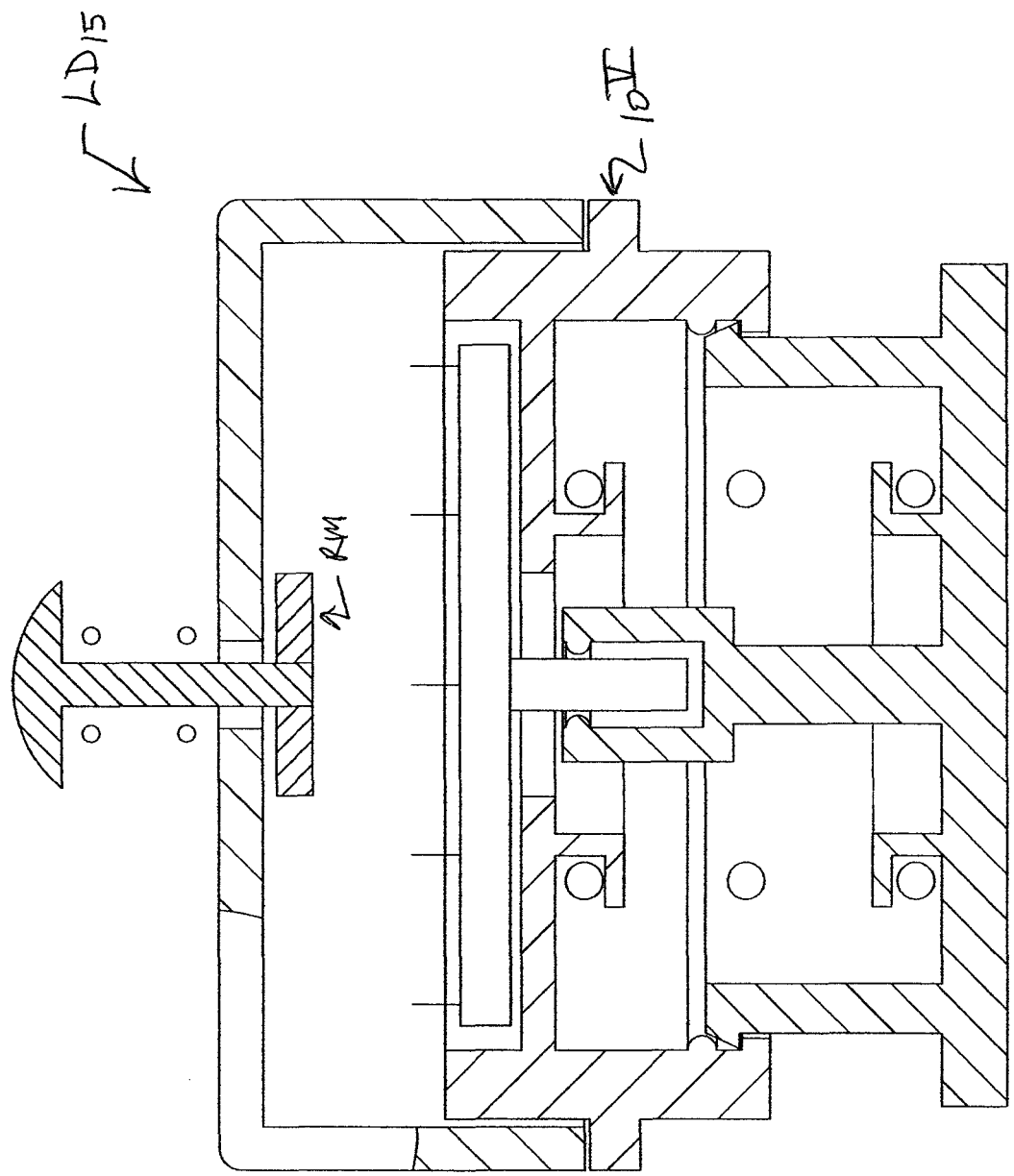
FIG. 41 shows a side cross-section view of the embodiment of FIG. 40 in an assembled state.
Figure 42:
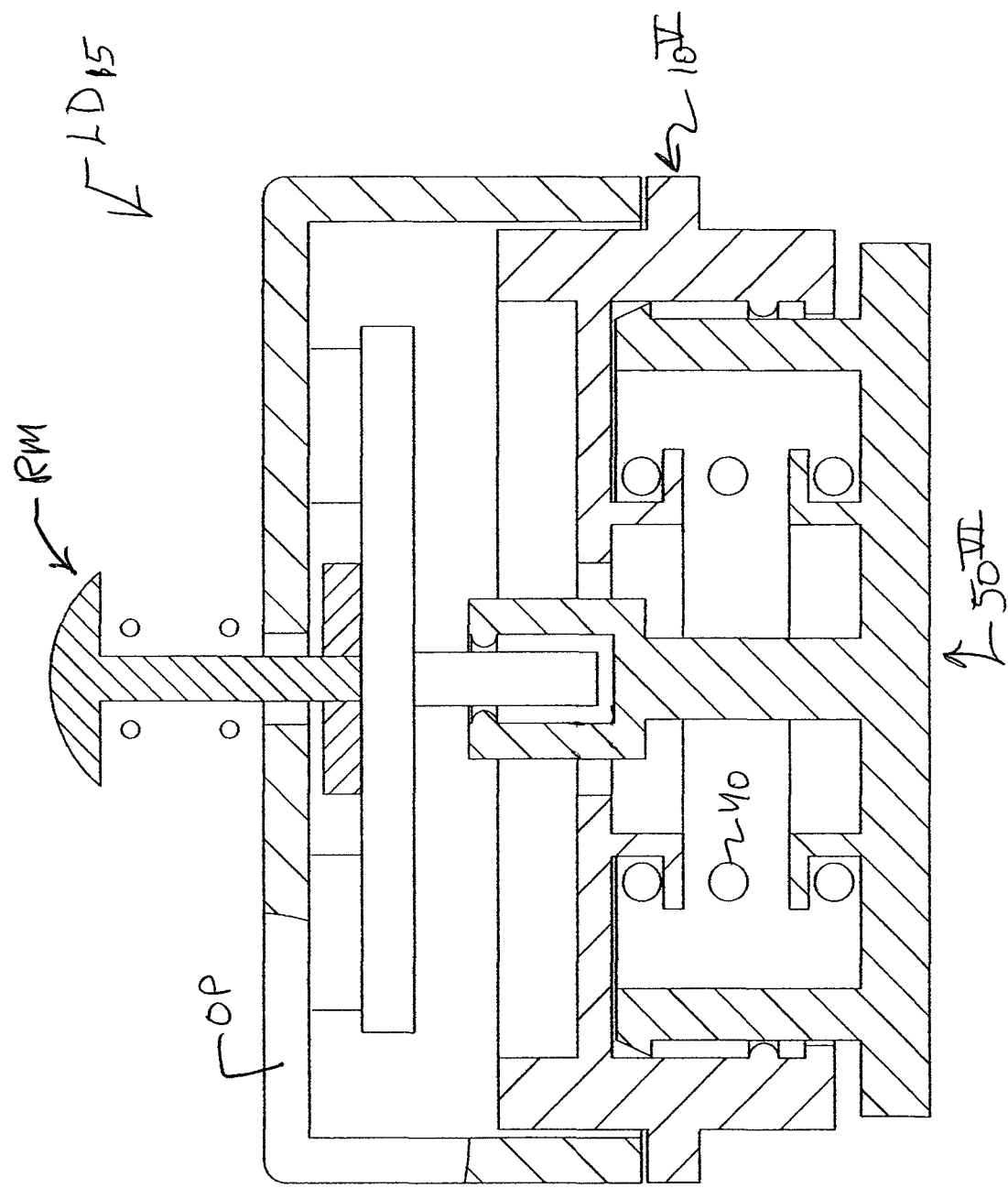
FIG. 42 shows a side cross-section view of the embodiment of FIG. 41 in a triggered state or a puncturing position.
Figure 43:
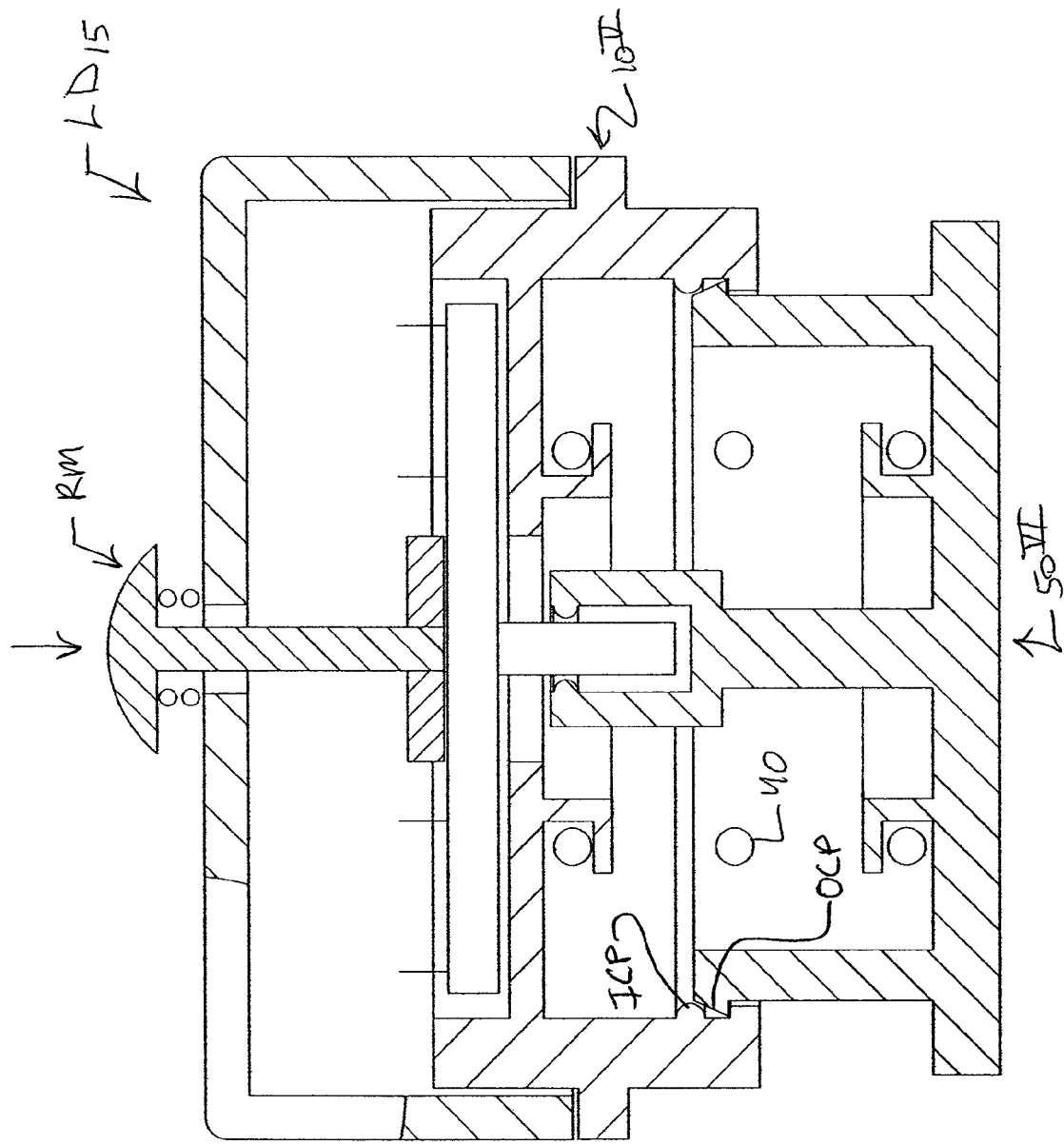
FIG. 43 shows a side cross-section view of the embodiment of FIG. 41 after the device moves the back cap back from the position shown in FIG. 42 to the position shown in FIG. 41.

FIGS. 40-43 show another embodiment of a cartridge lancet device. In FIG. 40, the device $LD_{15}$ is shown in an initial or retracted position with the front cap 200'' removed. This embodiment utilizes a rotatably indexable front cap 200'' which allows the user to position the opening OP over each lancet needle LN. A spring S1 is utilized to bias a device RM for moving the back cap $50^{VI}$ to the retracted position. A main body $10^V$ has an internal circumferential projection which temporarily retains the back cap $50^{VI}$ in a retracted position. A spring 40 has one end connected to a lower retaining flange LRF of the back cap $50^{VI}$ and another end connected to an upper retaining flange URF of the body $10^V$ so as to bias the back cap $50^{VI}$ towards the extended or puncturing position. The back cap $50^{VI}$ can be temporarily locked in the retracted position by virtue of engagement between an outer circumferential projection OCP and the projection ICP. A cartridge assembly $30^{IV}$ has a removable installation member RIM which can be broken off at a breakable joint BJ after the cartridge $30^{IV}$ is installed on the plunger portion of the back cap $50^{VI}$. FIG. 41 shows the embodiment of FIG. 40 in an assembled state. FIG. 42 shows the embodiment of FIG. 41 in a triggered state or a puncturing position. FIG. 43 shows a side cross-section view of the embodiment of FIG. 41 after the device RM moves the back cap $50^{VI}$ back from the position shown in FIG. 42 to the position shown in FIG. 41. This movement can occur by the user depressing on the button portion of the device RM.

Figure 44:
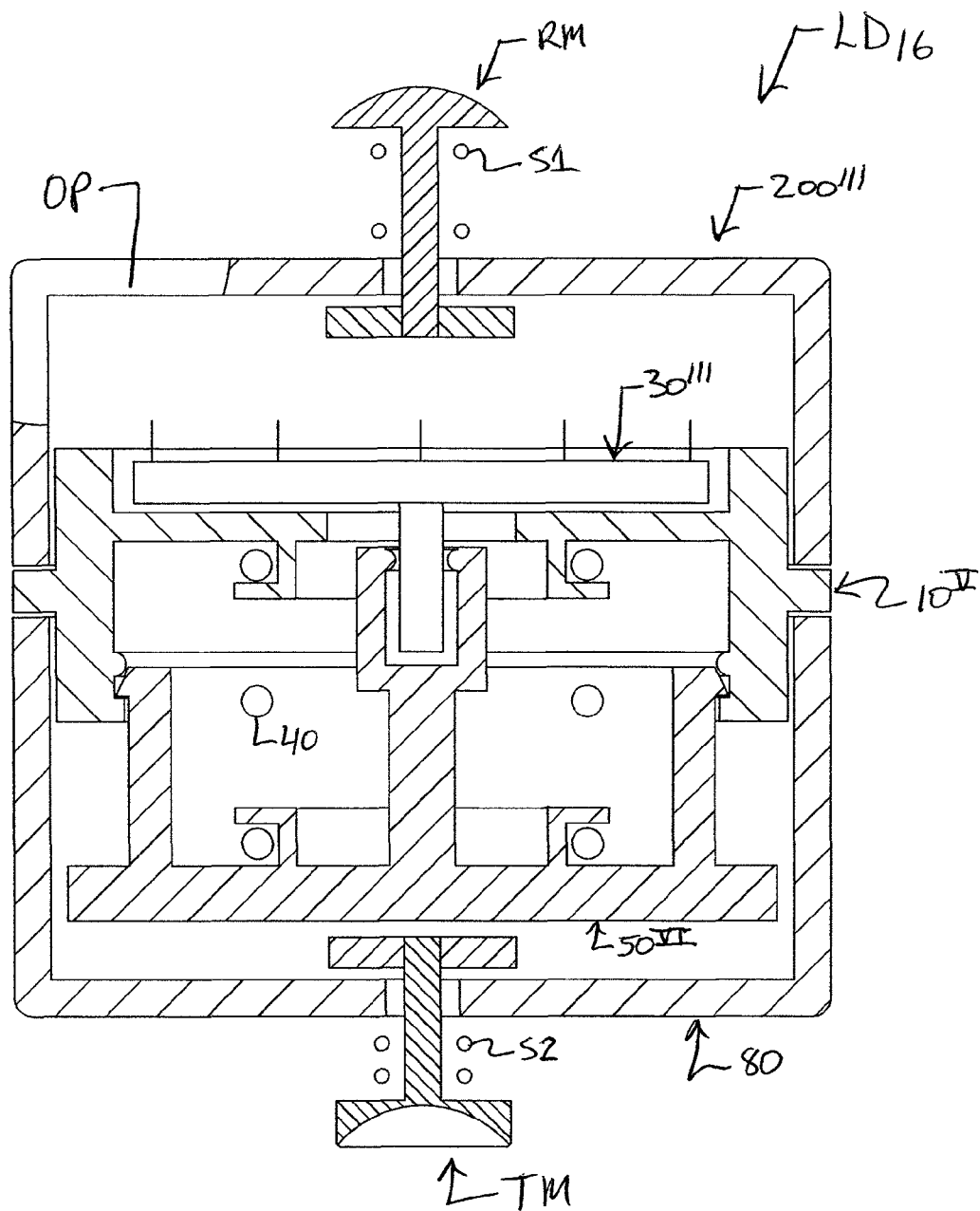
FIG. 44 shows a side cross-section view of another embodiment of a cartridge lancet device. The device is shown in an initial or retracted position. This embodiment utilizes a rotatably indexable front cap which allows the user to position the opening over each lancet needle and which includes a spring biased device for moving the back cap to the retracted position, a main body, a spring, a back cap which can be temporarily locked in the retracted position, a cartridge assembly, and a back cover which includes a spring biased trigger member.
Figure 95:
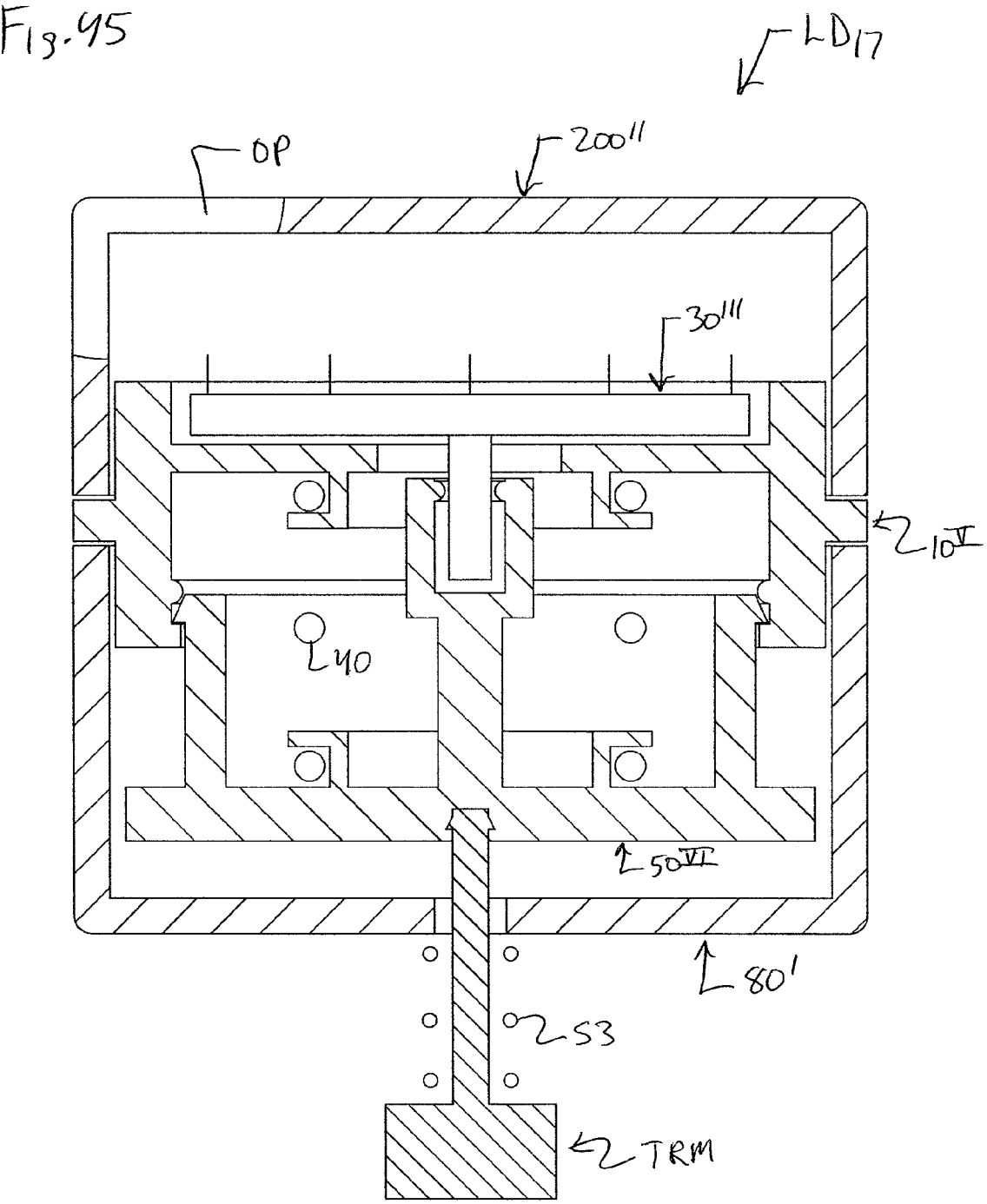

FIG. 44 shows another embodiment of a cartridge lancet device. The device $LD_{16}$ is shown in an initial or retracted position. This embodiment utilizes a rotatably indexable front cap 200''' which allows the user to position the opening OP over each lancet needle LN and which includes a spring S1 biased device RM for moving the back cap $50^{VI}$ to the retracted position. The device also includes a main body $10^V$ and a spring 40. The back cap 50$^{VI}$ can be temporarily locked in the retracted position as in the previous embodiment. The cartridge assembly 30''' is similar to that of previous embodiments. A back cover 80 is fixed to the body 10$^V$ and includes a spring S2 biased trigger member TM. Triggering occurs when the user depresses the trigger TM. After triggering, the user can rotate the front cap 200''' to place the opening OP over the next lancet needle LN and then depress the device RM to move the back cap 50$^{VI}$ back to the retracted position. The spring 40 has one end connected to a lower retaining flange of the back cap 50$^{VI}$ and another end connected to an upper retaining flange of the body 10$^V$ so as to bias the back cap 50$^{VI}$ towards the extended or puncturing position. The system for allowing the front cap 200''' to be rotated in only one direction and also temporarily retained so that the opening OP is arranged over each of the lancet needles LN can utilize any of the configurations disclosed herein.

FIG. 45 shows another embodiment of a cartridge lancet device. The device $LD_{17}$ is shown in an initial or retracted position. This embodiment utilizes a rotatably indexable front cap 200'' which allows the user to position the opening OP over each lancet needle LN. The device also includes a main body 10$^V$ and a spring 40. The back cap 50$^{VI}$ can be temporarily locked in the retracted position as in the previous embodiments. The cartridge assembly 30''' is similar to that of previous embodiments. A back cover 80' is fixed to the body 10$^V$. A spring S3 biases a trigger and resetting member TRM. Triggering occurs when the user depresses the member TRM. After triggering, the user can rotate the front cap 200'' to place the opening OP over the next lancet needle LN and then pull out on the member TRM to move the back cap 50$^{VI}$ back to the retracted position. The spring 40 has one end connected to a lower retaining flange of the back cap 50 and another end connected to an upper retaining flange of the body 10$^V$ so as to bias the back cap 50$^{VI}$ towards the extended or puncturing position. The system for allowing the front cap 200'' to be rotated in only one direction and also temporarily retained so that the opening OP is arranged over each of the lancet needles LN can utilize any of the configurations disclosed herein.

FIGS. 46 and 47 show another embodiment of a cartridge lancet device. In FIG. 46, the device $LD_{18}$ is shown in an initial or retracted position. In FIG. 47, the device $LD_{18}$ is shown in the puncturing or extended position. This embodiment utilizes a rotatably indexable front cap 200'' which allows the user to position the opening OP over each lancet needle LN. The device also includes a main body 10$^{VI}$ and a spring 40. The back cap 50$^{VII}$ can be temporarily locked in the retracted position when a rear flange portion thereof is engaged by two oppositely arranged pivotally mounted (i.e., pivotally mounted to the back cover 80'') trigger members TM'. The cartridge assembly 30''' is similar to that of previous embodiments. A back cover 80'' is fixed to the body 10$^{VI}$. A biasing member BM, which can be in the form of a compressible ring, biases the trigger members TM' towards an initial position. Triggering occurs when the user depresses or squeezes together the members TM'. After triggering, the user can rotate the front cap 200'' to place the opening OP over the next lancet needle LN and then pull out on the member RM' to move the back cap 50$^{VII}$ back to the retracted position. The system for allowing the front cap 200'' to be rotated in only one direction and also temporarily retained so that the opening OP is arranged over each of the lancet needles LN can utilize any of the configurations disclosed herein.

Figure 50:
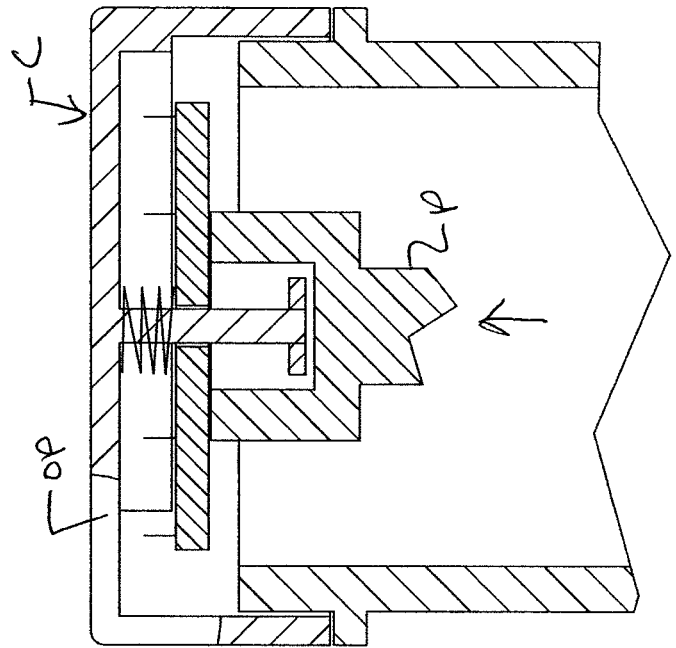
FIG. 50 shows a side cross-section view of the embodiment of FIG. 49 in a triggered or puncturing position.
Figure 49:
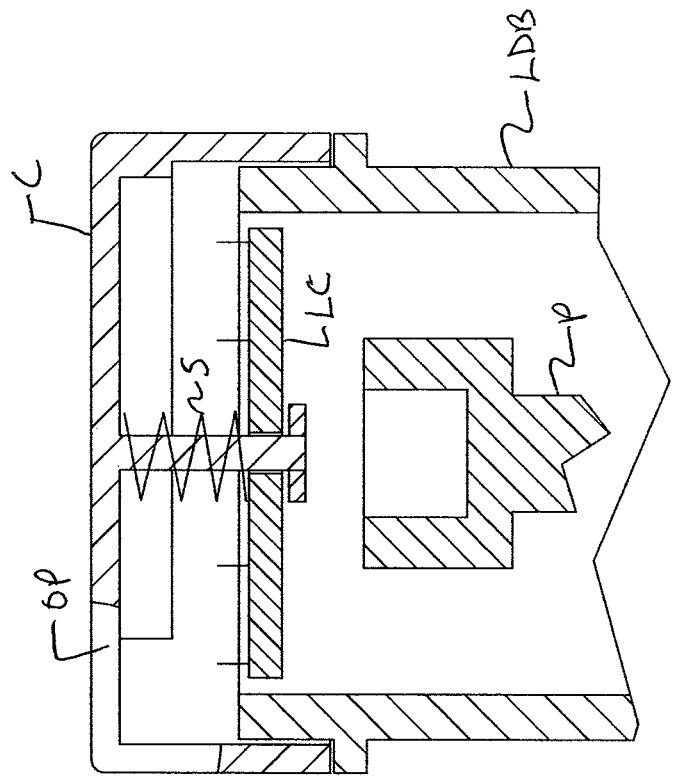
FIG. 49 shows a side cross-section view of the embodiment of FIG. 48 in an assembled and pre-triggered position.

FIGS. 48-50 show another embodiment of a cartridge lancet device. This embodiment $LD_{19}$ utilizes an axially movable plunger P arranged in a lancet device body LDB which can be of any type such as a test meter or lancet device. A removable front cap C has an opening OP and a cartridge assembly LC mounted to a hub portion of the cap C so as to be removable and/or replaceable with the front cap C, and a spring S for biasing the cartridge LC towards a retracted position. FIG. 49 shows the embodiment of FIG. 48 in an assembled and pre-triggered position. FIG. 50 shows the embodiment of FIG. 49 in a triggered or puncturing position. The system for allowing the front cap C to be rotated in only one direction and also temporarily retained so that the opening OP is arranged over each of the lancet needles LN can utilize any of the configurations disclosed herein. By way of non-limiting example, the plunger P can be caused to move axially by a mechanism system such as a spring or via an electrical/mechanical system such as a solenoid.

Figure 51:
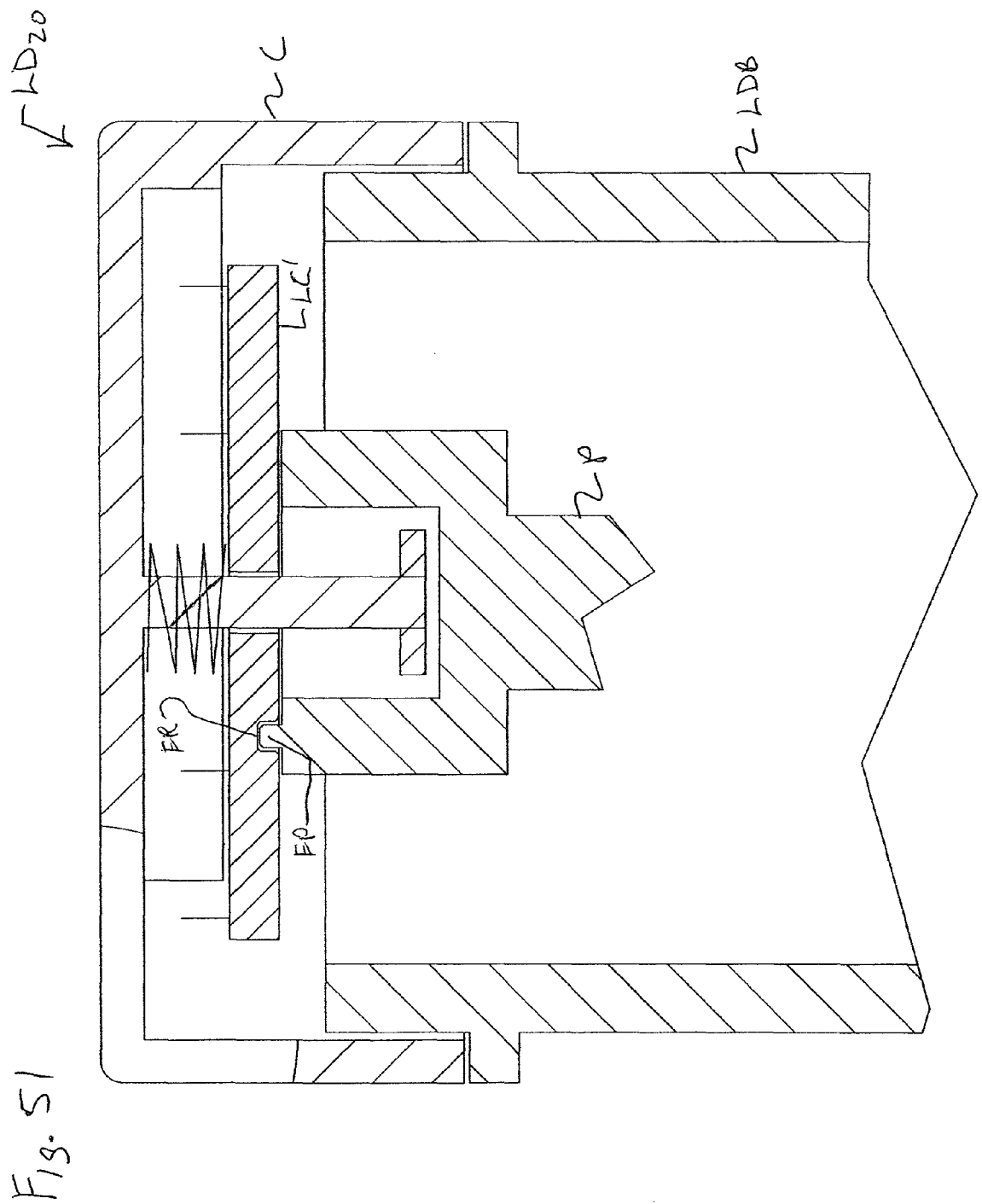
FIG. 51 shows one non-limiting way in which the embodiment of FIG. 49 can utilize a system for aligning the plunger with the cartridge in order to allow the plunger to rotate the cartridge to another puncturing position.

FIG. 51 shows another lancet device embodiment $LD_{20}$ similar to that of FIGS. 48-50 and illustrates one non-limiting way in which the embodiment of FIGS. 48-50 can utilize a system for aligning the plunger P with the cartridge LC in order to allow the plunger P to rotate the cartridge LC to another puncturing position. In this variation, the front cap C would be mounted to the body LDB so as to be prevented from rotating. The system for aligning the plunger P with the cartridge LC can utilize one or more engaging projections EP which can extend into one or more engaging recesses ER of the cartridge LC so as to cause the cartridge to rotate with the plunger P.

FIG. 52 shows another embodiment of a cartridge lancet device. This embodiment $LD_{21}$ utilizes an axially movable plunger P arranged in a lancet device body LDB which can be of any type such as a test meter or lancet device. A removable front cap C' has an opening OP and a cartridge assembly LC mounted to a hub portion of the cap C' so as to be removable and/or replaceable with the front cap C, and a spring S' for biasing the cartridge LC towards a retracted position. The hub portion of the cap C' has an upper indexing mechanism IM which can be gripped by the user so as to allow the user to rotate the cartridge LC through various positions which place one of the lancet needles LN into alignment with the opening OP. The mechanism IM can be retained in a number of rotational positions by engagement (i.e., a temporarily locking engagement) between the engaging projection EP' and one of a plurality of engaging recesses ER' (i.e., one for each lancet needle LN) formed in the cap C'. In order to ensure that the cartridge LC does not rotate relative to the hub portion (but allows for the cartridge LC to slide axially relate to the hub portion) of the mechanism IM, the opening in the cartridge LC and the hub portion can have a non-circular shape, e.g., square-shape. This embodiment preferably utilizes a front cap C' which is mounted to the body LDB in only one rotational position so as to place the opening OP in a predetermined position. By way of non-limiting example, the plunger P can be caused to move axially by a mechanism system such as a spring or via an electrical/mechanical system such as a solenoid.

Figure 53:
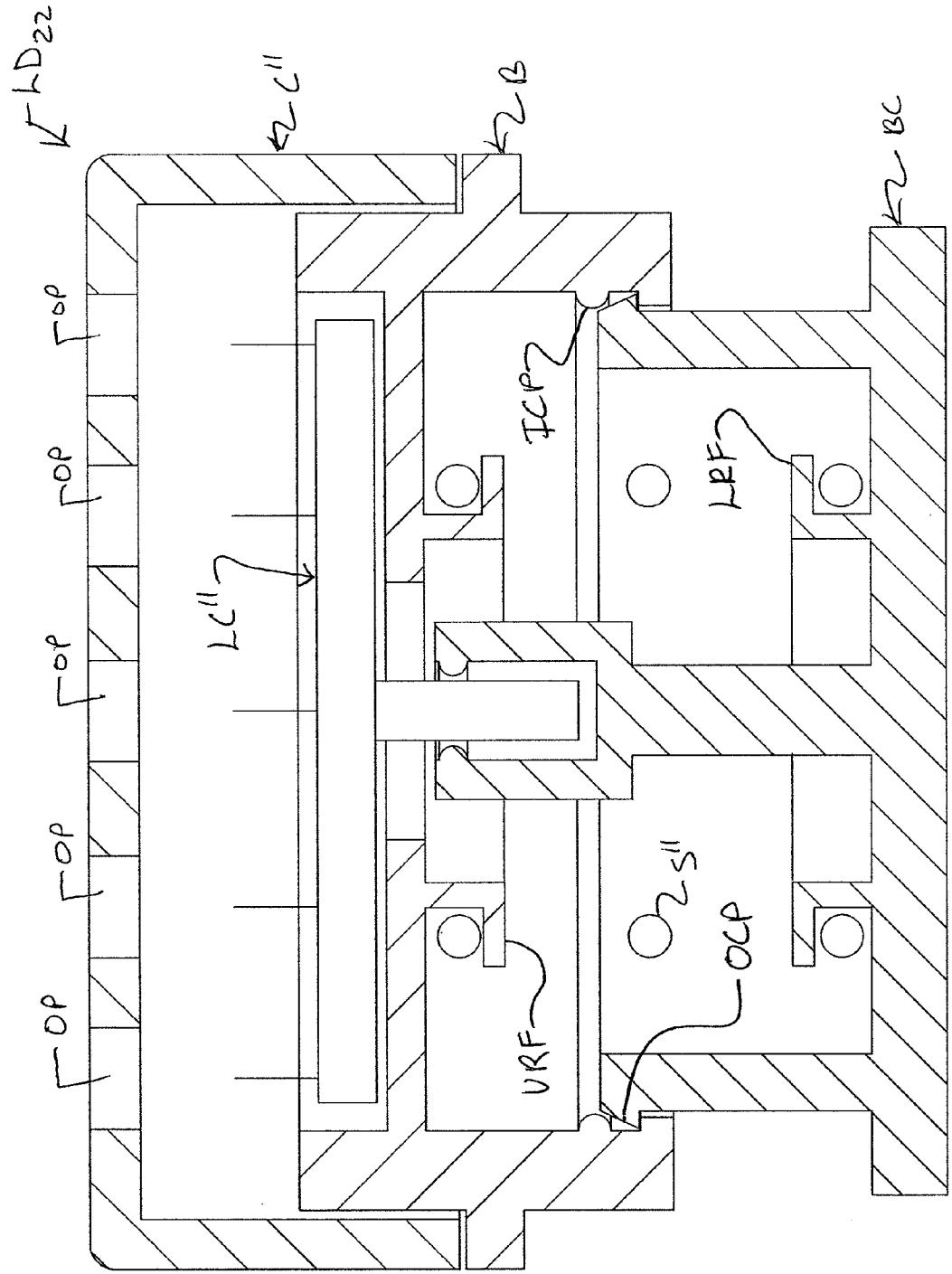
FIG. 53 shows a side cross-section view of another embodiment of a cartridge lancet device. This embodiment utilizes multiple openings in the front cap in order to function as a skin allergy testing device. The front cap is cross-sectioned through the openings rather than the center of the cap.
Figure 54:
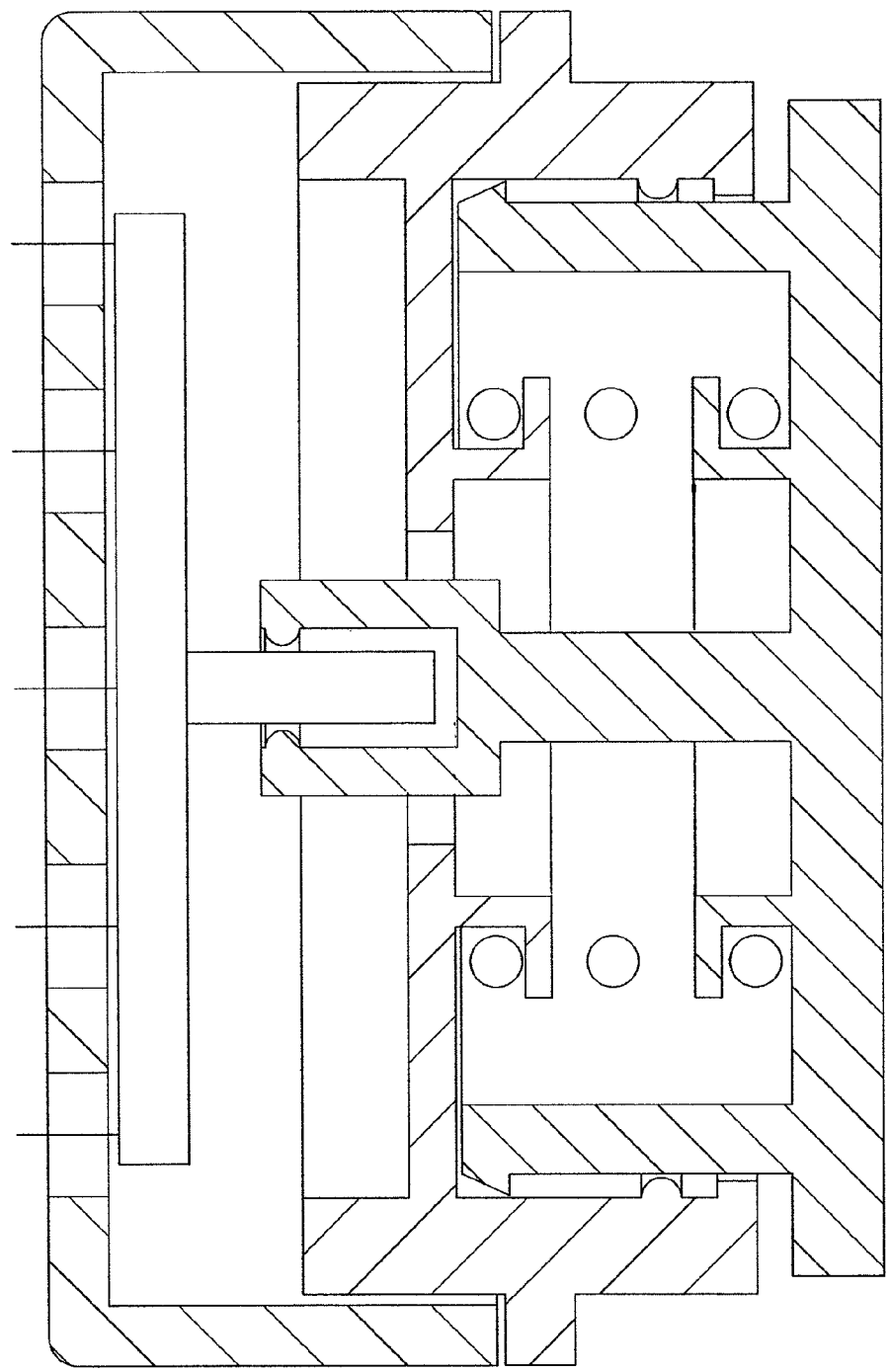
FIG. 54 shows a side cross-section view of the embodiment of FIG. 53 in the puncturing position.

FIGS. 53 and 54 show another embodiment of a cartridge lancet device. This embodiment $LD_{22}$ utilizes multiple openings OP (arranged in the form of a bolt-hole pattern and/or in a position like the numbers of a clock face), i.e., one opening OP aligned with each lancet needle LN, in the front cap C''. As such, this embodiment can function as a skin allergy testing device because it can cause a plurality of punctures in a user's skin. A main body B has an internal circumferential projection which temporarily retains the back cap BC in a retracted position. A spring S'' has one end connected to a lower retaining flange LRF of the back cap BC and another end connected to an upper retaining flange URF of the body B so as to bias the back cap BC towards the extended or puncturing position. The back cap BC can be temporarily locked in the retracted position by virtue of engagement between an outer circumferential projection OCP and the projection ICP. The cartridge LC" is installed on the plunger portion of the back cap BC. FIG. 53 shows an assembled and armed state. FIG. 52 shows this embodiment in a triggered state or a puncturing position. This triggering movement can occur by the user squeezing together the from cap C" and the back cap BC as in many of the previous embodiments.

Figure 58:
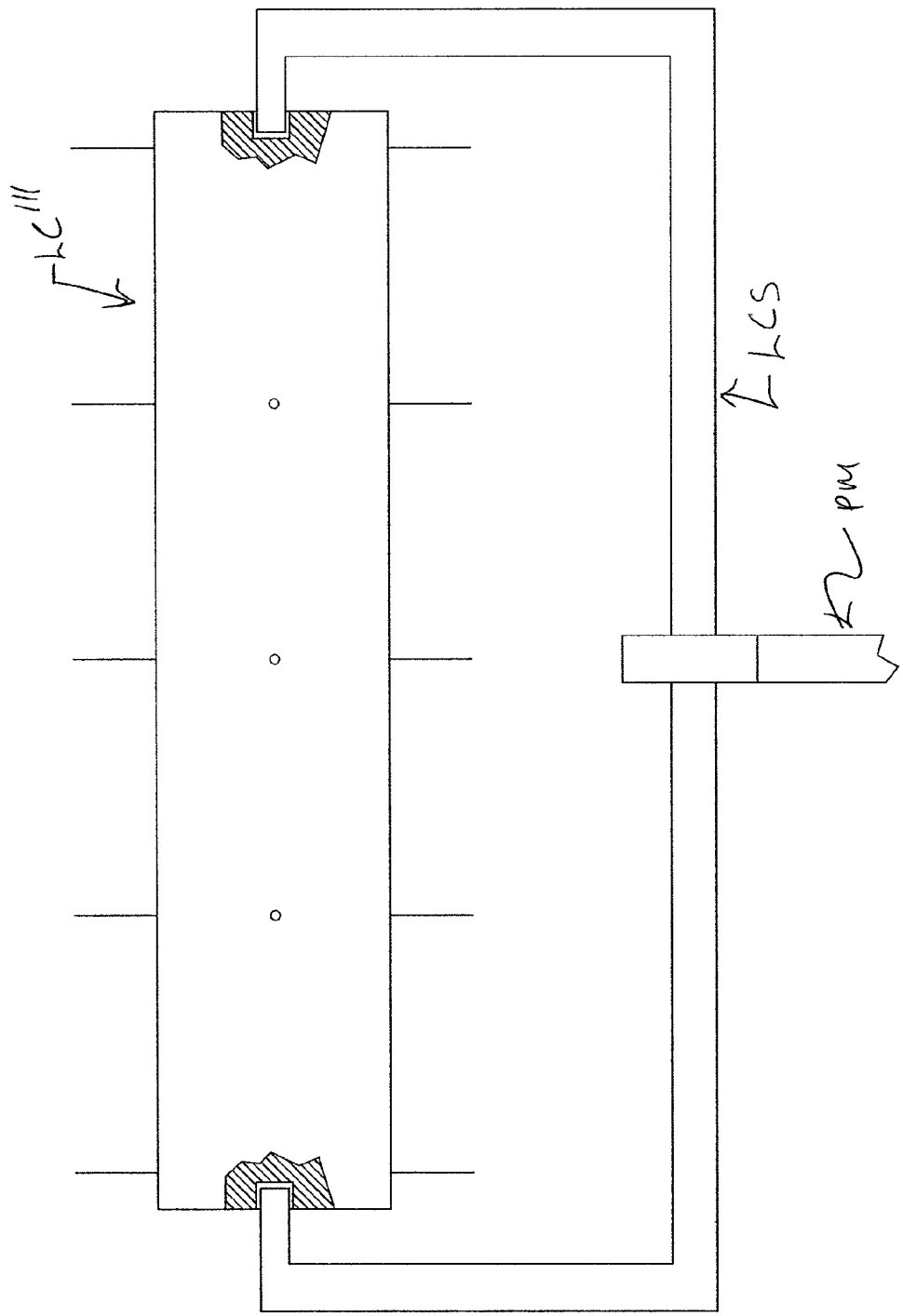
FIG. 58 shows the cartridge of FIG. 55 mounted to the mechanism of FIG. 57.
Figure 59:
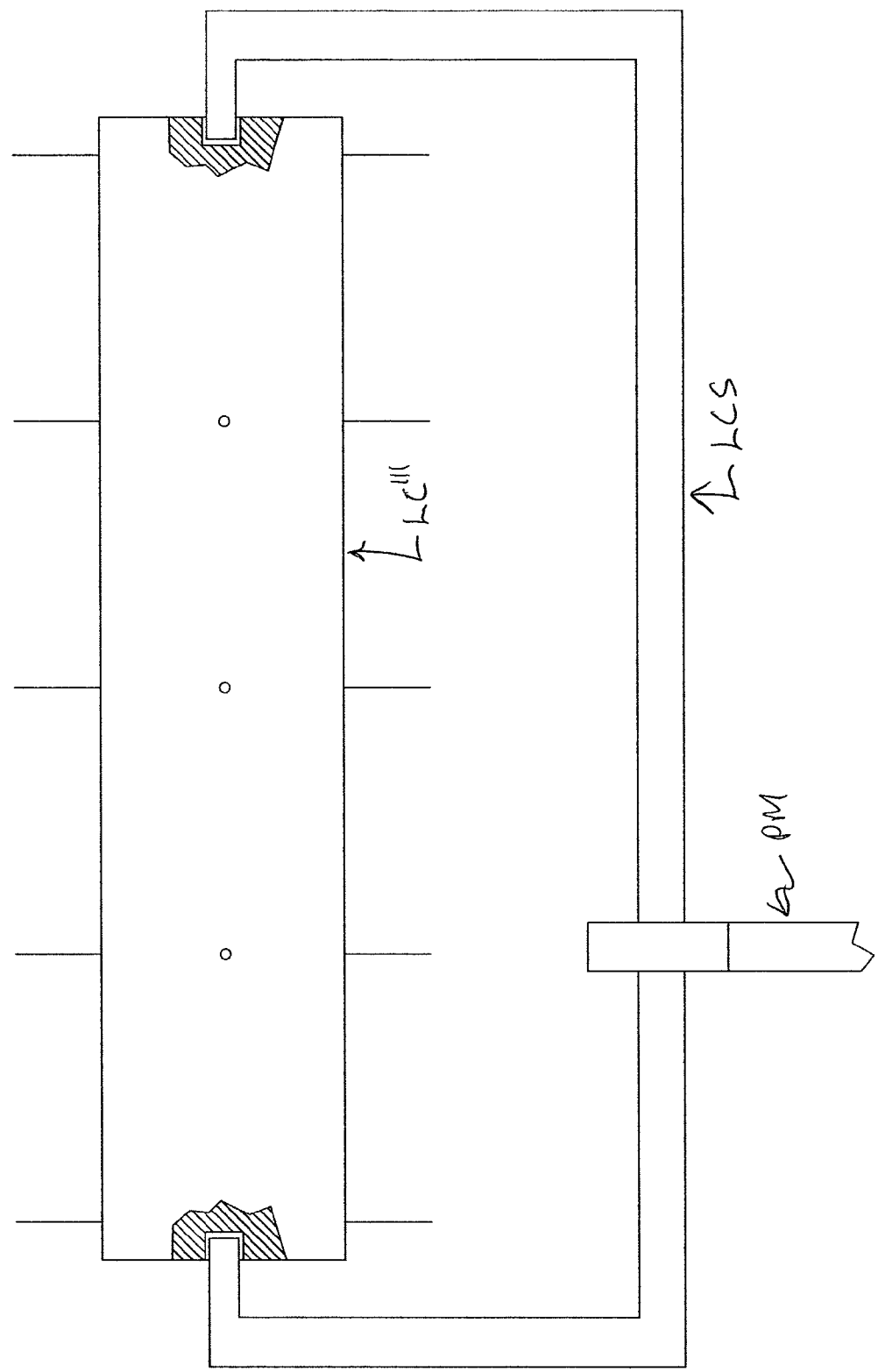
FIG. 59 shows the arrangement of FIG. 58 after the cartridge has been moved to another puncturing position.

FIGS. 55-59 show another embodiment of a cartridge LC''' which can be used on a cartridge lancet device having a moveable plunger PM. The cartridge LC''' of this embodiment (unlike previous embodiments which utilized dish-shaped or ring-shaped cartridges) utilizes a polygonal shaped body having one or more rows of lancet needles LN arranged on multiple sides of the cartridge body and includes axial end openings EO. FIG. 57 shows one non-limiting plunger mechanism PM having a lancet cartridge support LCS for mounting the cartridge of FIG. 55 to a device. The support LCS utilizes support arms SA configured to extend into the openings EO. FIG. 58 shows the cartridge of FIG. 55 mounted to the mechanism of FIG. 57. FIG. 59 shows the arrangement of FIG. 58 after the cartridge has been moved or slid sideways to another puncturing position. This embodiment can function in a number of possible ways. For example, the cartridge LC''' can be moved sideways, relative to a cap having an opening (not shown), until all of the lancet needles LN are used up. Then, the cartridge LC''' can be rotated to position another side having fresh lancet needles LN facing upwards. This can continue until all of the lancet needles LN are used up. The cartridge LC''' can also be rotated to the next adjacent side after each use, relative to a cap having an opening (not shown), until all of the lancet needles LN are used up. Then, the cartridge LC''' can slid sideways to position the next circumferential row of fresh lancet needles LN into alignment with the opening in the cap. This can continue until all of the lancet needles LN are used up. Of course, the cartridge LC''' is not limited to square-shaped cross-sections as shown in FIG. 56, and can also be circular, oval, triangular, as well as multi-sided, e.g., 5-sided, 6-sided, etc.

Figure 60:
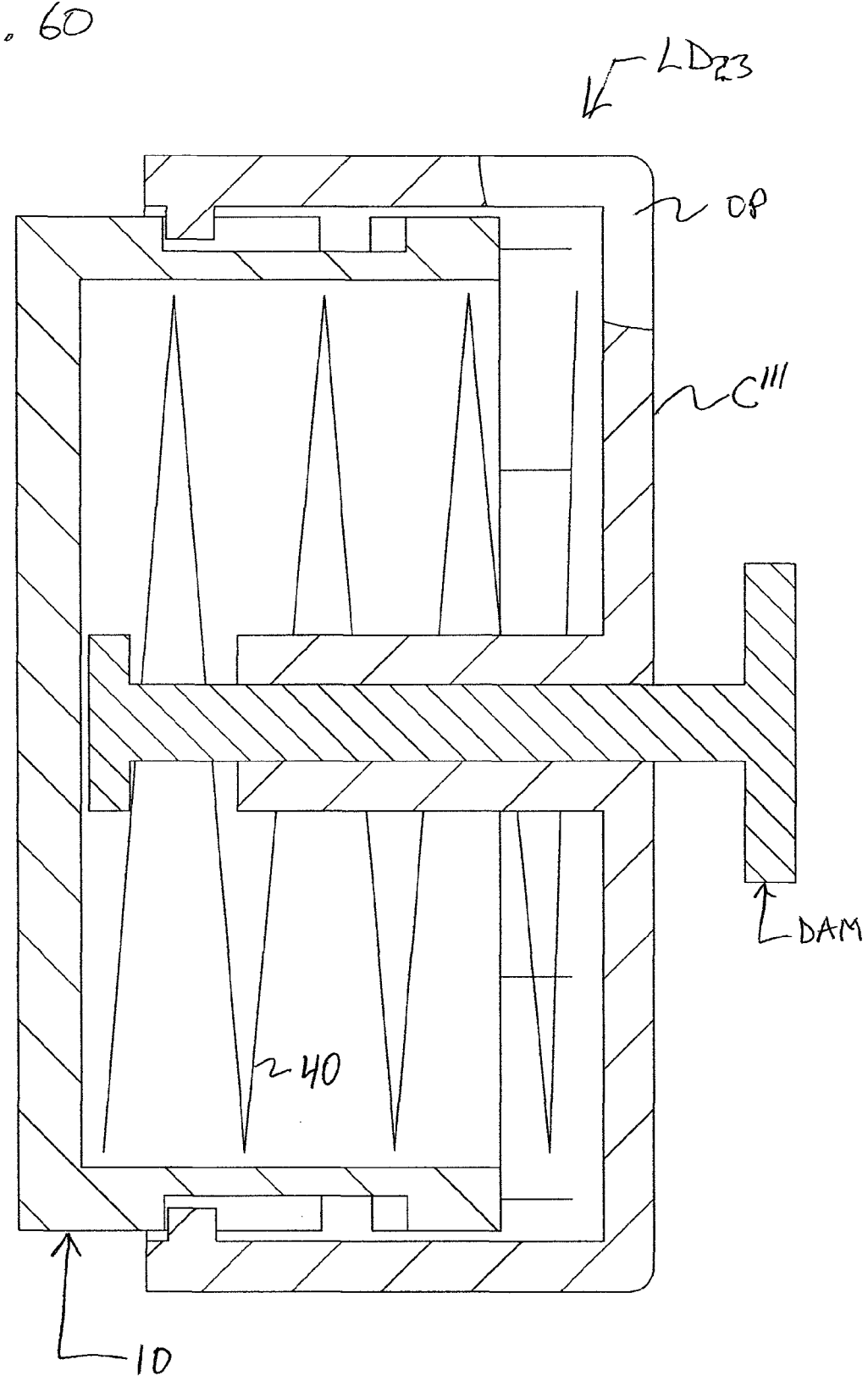
FIG. 60 shows a side cross-section view of another embodiment of a cartridge lancet device. The device is shown in a puncturing position. The spring is not shown in cross-section. This embodiment is similar to that of FIG. 12 except that the cap used in the embodiment shown in FIG. 12 includes a depth adjustment device.

FIG. 60 shows another embodiment of a cartridge lancet device. The device $LD_{23}$ is shown in a puncturing position. This embodiment is similar to that of FIG. 12 except that the cap C''' includes a depth adjustment device DAM. The depth adjustment occurs by the user rotating a gripping portion of the device DAM relative to the cap C''' which causes external threads (not shown) of the member DAM to engage with internal threads (not shown) of the central projecting portion of the cap C'''. This changes the axial position of the stopping portion of the member DAM relative to the cap C'''.

FIG. 61 shows another embodiment of a cartridge lancet device. The device $LD_{24}$ is shown in a puncturing position. This embodiment is similar to that of FIG. 40 except that the cap and cartridge are differently configured. This embodiment utilizes a rotatably indexable front cap $C^{IV}$ which allows the user to position the opening OP over each lancet needle LN. A main body $10^V$ has an internal circumferential projection which temporarily retains the back cap $50^{VI}$ in a retracted position. A spring 40 has one end connected to a lower retaining flange of the back cap $50^{VI}$ and another end connected to an upper retaining flange of the body $10^V$ so as to bias the back cap $50^{VI}$ towards the extended or puncturing position. The back cap $50^{VI}$ can be temporarily locked in the retracted position by virtue of engagement between an outer circumferential projection and the projection. The cartridge assembly $30^V$ has a grip-able installation member GIM which allows the user to more safely grip the cartridge $30^V$ during installation and removal. As with previous embodiments, the triggering of the device occurs by the user squeezing together the front cap $C^{IV}$ and the back cap $50^{IV}$. The device can be placed back into a trigger-set position by the user gripping the front cap $C^{IV}$ and the back cap $50^{VI}$ and pulling them away from each other until the back cap $50^{VI}$ is temporarily locked in the retracted position by virtue of engagement between an outer circumferential projection and the inner circumferential projection.

Of course, the invention contemplates embodiments wherein the body and front cover have a non-circular shapes similar to that of U.S. Pat. No. 5,464,418 to SCHRAGA, the disclosure of which is hereby expressly incorporated by reference herein it its entirety.

The various parts, with the exception of the springs, can preferably be made as one-piece structures by e.g., injection molding. In this regard, they are preferably made of a plastic or synthetic resin such as, e.g., ABS plastic. The body and can also be made of ABS—Metallic Silver and have a finish designated as SPI-A2. The front cover and back-cap may also be made of ABS—Light Blue and have a finish designated as SPI-A2. The cartridge can be made of such materials and can also be made of Delrin—Natural and have a finish designated as SPI-C1. Of course, other materials and/or finishes may be utilized, without leaving the scope of the invention. Moreover, each part may even be made of a plurality of sections of parts which are joined together to form the complete parts, without leaving the scope of the invention. Thus, all the parts of the lancet device, with the exception of the springs (which can be made of spring steel) and with the exception of the lancet needles (which can be a conventional metal needle mounted to a plastic cartridge body), may be made from plastic materials and can be formed using conventional injection molding techniques or other known manufacturing methods. The front cap and/or body, for example, can be integrally formed with grooves and/or projections and with the indicating marks. However, when practical, other materials and manufacturing processes may also be utilized. Examples of desirable plastics include polypropylene (PP), polyvinyl chloride (PVC), acrylonitrile butadiene styrene (ABS), nylon, linear polyoxymethylene-type acetal resin, e.g., "DELRIN", and polycarbonate (PC), e.g., "LEXAN". The invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. An assembly for use on a device, the assembly comprising:
   a member comprising a plurality of lancet needles arranged generally parallel to each other; and
   one of:
      a cap comprising a single lancet opening structured and arranged to receive therein an end portion of a finger tip; and
      a cap comprising a plurality of openings which are each sized to allow one of the lancet needles to pass therethrough,
   wherein the assembly is structured and arranged to assume a first position and a second position, and, in the second position, a distance between an outer surface of the cap and ends of the plurality of lancet needles is less than in the first position.

2. The assembly of claim 1, wherein the device comprises at least one of a lancet device, a testing device, and a skin allergy test.

3. The assembly of claim 1, wherein the assembly comprises the cap comprising a single lancet opening structured and arranged to receive therein an end portion of a finger tip device, and wherein the lancet opening is arranged in a peripheral area of the cap.

4. The assembly of claim 1, wherein the assembly comprises the cap comprising a plurality of openings which are each sized to allow one of the lancet needles to pass therethrough, and wherein the member is movable at least from one position wherein each lancet needle does not extend out past an outer surface of the cap and another position wherein each lancet needle extends out past the outer surface of the cap.

5. The assembly of claim 1, wherein the assembly comprises the cap comprising a single lancet opening structured and arranged to receive therein an end portion of a finger tip device, and wherein the lancet opening movable from one position which coincides with one of the lancet needles to another position which coincides with another of the lancet needles.

6. The assembly of claim 1, wherein the assembly comprises the cap comprising a single lancet opening structured and arranged to receive therein an end portion of a finger tip device, and wherein the member is movable from one position wherein the lancet opening coincides with one of the lancet needles to another position wherein the lancet opening coincides with another of the lancet needles.

7. The assembly of claim 1, wherein the cap and member are generally circular shaped.

8. The assembly of claim 1, wherein the cap is generally cylindrically shaped.

9. The assembly of claim 1, wherein the cap comprises a generally circular end surface and a generally cylindrical sidewall and wherein the lancet opening is located at a corner area between the end surface and the sidewall.

10. The assembly of claim 1, wherein the lancet opening is located at a corner area of the cap.

11. The assembly of claim 1, further comprising at least one spring structured and arranged to bias the member towards the cap.

12. The assembly of claim 1, further comprising at least one spring structured and arranged to bias the member away from the cap.

13. The assembly of claim 1, wherein the member and the cap are movable relative to each other from a retracted position to a puncturing position and one of:
   the cap is rotatable relative to the member; and
   the member is rotatable relative to the cap.

14. The assembly of claim 1, wherein the member and the cap are axially movable relative to each other and the cap is rotatable relative to the member.

15. The assembly of claim 1, wherein the member and the cap are axially movable relative to each other and the member is rotatable relative to the cap.

16. The assembly of claim 1, wherein the member and the cap are movable relative to each other and at least one of:
   the cap is a one-piece member; and
   the member is a one-piece member.

17. The assembly of claim 1, wherein the member and the cap are movable relative to each other and at least one of:
   the cap is a generally cylindrical member; and
   the member is a generally cylindrical member.

18. The assembly of claim 1, wherein the member and the cap are movable relative to each other and at least one of:
   the cap is a generally cylindrical member; and
   the member is a generally disk-shaped member.

19. The assembly of claim 1, wherein the member and the cap are movable relative to each other and at least one of:
   the cap is a rotatable between distinct angular positions which correspond to angular positions of the lancet needles; and
   the member is a rotatable between distinct angular positions which correspond to angular positions of the lancet needles.

20. The assembly of claim 1, wherein the member and the cap are movable relative to each other and at least one of:
   the cap is rotatable between distinct angular positions which correspond to angular positions of the lancet needles and axially movably only at the distinct angular positions; and
   the member is rotatable between distinct angular positions which correspond to angular positions of the lancet needles and axially movably only at the distinct angular positions.

21. The assembly of claim 1, wherein the member and the cap are movable relative to each other and at least one of:
   the cap is a one-piece member; and
   the member is a one-piece member that is capable of being mounted to a portion of the device.

22. The assembly of claim 1, wherein the device is structured and arranged to be disposed of after all of the lancet needles are used to puncture a user's skin.

23. The assembly of claim 1, wherein the member is non-removably mounted to a portion of the device, whereby the device is structured and arranged to be disposed of after all of the lancet needles are used to puncture a user's skin.

24. The assembly of claim 1, wherein the member and the cap are movable relative to each other and at least one of: the cap comprises a member for limiting axial movement of the relative movement of the cap and the member; and the member comprises a member for limiting axial movement of the relative movement of the cap and the member.

25. The assembly of claim 1, wherein the member is removably mounted to a movable portion of the device.

26. The assembly of claim 1, wherein at least one of:
   the member is removably mounted to an axially movable portion of the device; and
   the member is removably mounted to an axially and rotatably movable portion of the device.

27. The assembly of claim 1, wherein the member is mounted to an axially and rotatably movable portion of the device.

28. The assembly of claim 27, further comprising a device for rotating the movable portion of the device between discrete rotational positions, wherein each position results in the lancet needle opening being substantially aligned with one of the lancet needles.

29. The assembly of claim 27, further comprising a device for rotating the movable portion of the device between discrete rotational positions, wherein each position results in one of the lancet needles being substantially aligned with the lancet needle opening.

30. The assembly of claim 29, further comprising a back cap structured and arranged to move the movable portion from an initial position to a puncturing position.

31. The assembly of claim 30, further comprising a spring structured and arranged to bias the movable portion towards the initial position.

32. The assembly of claim 30, further comprising a spring structured and arranged to bias the movable portion towards the puncturing position.

33. The assembly of claim 1, further comprising a back cap structured and arranged to move the member from an initial position to a puncturing position.

34. The assembly of claim 1, wherein the cap is non-removably mounted.

35. The assembly of claim 1, wherein the cap is non-movably mounted.

36. The assembly of claim 1, wherein the member comprises a disk-shaped portion having a surface from which the lancet needles project and rod-shaped portion extending from a side opposite the surface.

37. The assembly of claim 1, further comprising at least one retractable protection member arranged to cover at least one of the lancet needles.

38. The assembly of claim 1, further comprising an arrangement for ensuring that the cap rotates in only one direction.

39. The assembly of claim 1, further comprising an arrangement for ensuring that the member rotates in only one direction.

40. The assembly of claim 1, further comprising an arrangement for ensuring that the cap rotates in only one direction relative to a body of the device.

41. The assembly of claim 1, further comprising an arrangement for ensuring that the lancet opening rotates in only one direction relative to a body of the device and between a number of discrete positions corresponding to a number of the lancet needles.

42. The assembly of claim 1, further comprising an arrangement for ensuring that the lancet opening moves in only one direction relative to a body of the device and between a number of discrete positions corresponding to a number of the lancet needles.

43. The assembly of claim 1, further comprising a system for guiding a linear movement of the member relative to a body of the device at each of a number of discrete positions corresponding to a number of the lancet needles.

44. The assembly of claim 1, further comprising a system for preventing rotational movement of the cap when the cap is arranged on a body of the device.

45. The assembly of claim 1, wherein the member comprises a device for allowing a user to safely install the member on a portion of the device.

46. The assembly of claim 1, wherein the member comprises a removable and/or breakable device for allowing a user to safely install the member on a portion of the device.

47. The assembly of claim 1, further comprising a system for moving the member to at least one of an initial position and a retracted position.

48. The assembly of claim 1, further comprising a mechanism mounted to the cap for moving the member to at least one of an initial position and a retracted position.

49. The assembly of claim 1, further comprising a trigger for causing the member to move from at least one of an initial position and a retracted position to a puncturing position.

50. The assembly of claim 1, further comprising a system moving the member to at least one of an initial position and a retracted position and for causing the member to move to a puncturing position.

51. The assembly of claim 1, further comprising a mechanism coupled to a portion of the device for at least one of:
moving the member to at least one of an initial position and a retracted position; and
for causing the member to move to a puncturing position.

52. The assembly of claim 1, further comprising a first mechanism coupled to a portion of the device for moving the member to at least one of an initial position and a retracted position and a second mechanism coupled to another portion of the device for causing the member to move to a puncturing position.

53. The assembly of claim 1, wherein the member is movably mounted to the cap.

54. The assembly of claim 1, wherein the member is axially movably mounted to the cap.

55. The assembly of claim 1, wherein the member is rotatably mounted to the cap.

56. The assembly of claim 1, wherein the member is non-removably mounted to the cap.

57. The assembly of claim 1, wherein the member is biased away from the cap by a biasing member arranged between the member and the cap.

58. The assembly of claim 1, wherein at least one of: the member is coupled to the cap and further comprise a mechanism for rotating the member relative to the cap between discrete positions; and the member is coupled to the cap and further comprise a mechanism for temporarily retaining and/or locking the member in a plurality of discrete rotational positions relative to the cap.

59. The assembly of claim 1, wherein the member additionally comprises at least one needle arranged generally perpendicular to the lancet needles.

60. A method of puncturing a surface of skin using the assembly of claim 1, the method comprising: disposing a skin engaging end of the cap against a user's skin; and manually causing the member to move towards a puncturing position.

61. A method of puncturing a surface of skin using the assembly of claim 1, the method comprising: adjusting a depth of penetration; and disposing a skin engaging end of the cap against a user's skin; and causing the member to move towards a puncturing position.

62. An assembly for use on a device, the assembly comprising:
a cartridge comprising a plurality of lancet needles arranged generally parallel to each other; and
a cap comprising a single lancet opening structured and arranged to receive therein an end portion of a finger tip,
wherein a distance between an outer surface of the cap and ends of the plurality of lancet needles is changeable between an initial position of the assembly and a puncturing position of the assembly.

63. The assembly of claim 62, further comprising a device for adjusting a depth of penetration into the finger tip.

* * * * *